United States Patent
Seifried et al.

(10) Patent No.: US 9,963,492 B2
(45) Date of Patent: May 8, 2018

(54) HIGH MOLECULAR WEIGHT, POST-TRANSLATIONALLY MODIFIED PROTEIN BRUSHES

(71) Applicants: Brian M. Seifried, Cambridge, MA (US); Bradley D. Olsen, Arlington, MA (US)

(72) Inventors: Brian M. Seifried, Cambridge, MA (US); Bradley D. Olsen, Arlington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days. days.

(21) Appl. No.: 15/155,933

(22) Filed: May 16, 2016

(65) Prior Publication Data

US 2017/0029478 A1 Feb. 2, 2017

Related U.S. Application Data

(60) Provisional application No. 62/161,334, filed on May 14, 2015.

(51) Int. Cl.
| | |
|---|---|
| *A61K 38/00* | (2006.01) |
| *C07K 14/47* | (2006.01) |
| *C07K 1/107* | (2006.01) |
| *C07K 1/113* | (2006.01) |

(52) U.S. Cl.
CPC .......... *C07K 14/4727* (2013.01); *C07K 1/107* (2013.01); *C07K 1/113* (2013.01); *C07K 14/47* (2013.01); *A61K 38/00* (2013.01)

(58) Field of Classification Search
None
See application file for complete search history.

(56) References Cited

U.S. PATENT DOCUMENTS

| | | |
|---|---|---|
| 2006/0150262 A1 | 7/2006 | Bienkowska et al. |
| 2011/0229510 A1 | 9/2011 | Danishefsky et al. |
| 2012/0253008 A1 | 10/2012 | Revets et al. |
| 2013/0096050 A1 | 4/2013 | Shandler |
| 2013/0196926 A1* | 8/2013 | MacKay ............... A61K 38/18 514/18.2 |

FOREIGN PATENT DOCUMENTS

AU 2014/271331 A1 1/2015

OTHER PUBLICATIONS

French and Robson, What is a conservative substitution? Journal of Molecular Evolution, Mar. 1983, vol. 19, Issue 2, pp. 171-175.*
Phillips et al., "High Efficiency Coupling of Diazonium Ions to Proteins and Amino Acids," J Biol Chem, 240(2): 699-704 Feb. 1965.
International Search Report and Written Opinion for International Application No. PCT/US16/32757 dated Sep. 30, 2016.

* cited by examiner

*Primary Examiner* — Thomas S Heard
(74) *Attorney, Agent, or Firm* — Dana M. Gordon; Foley Hoag LLP

(57) ABSTRACT

Disclosed are protein brushes that mimic mucin in physical and functional characteristics. The protein brushes have a variable number of tandem repeats similar to natural mucin and are modified at a number of their tyrosine residues to introduce brush substituents that mimic the hydrogel nature of mucin.

20 Claims, 41 Drawing Sheets

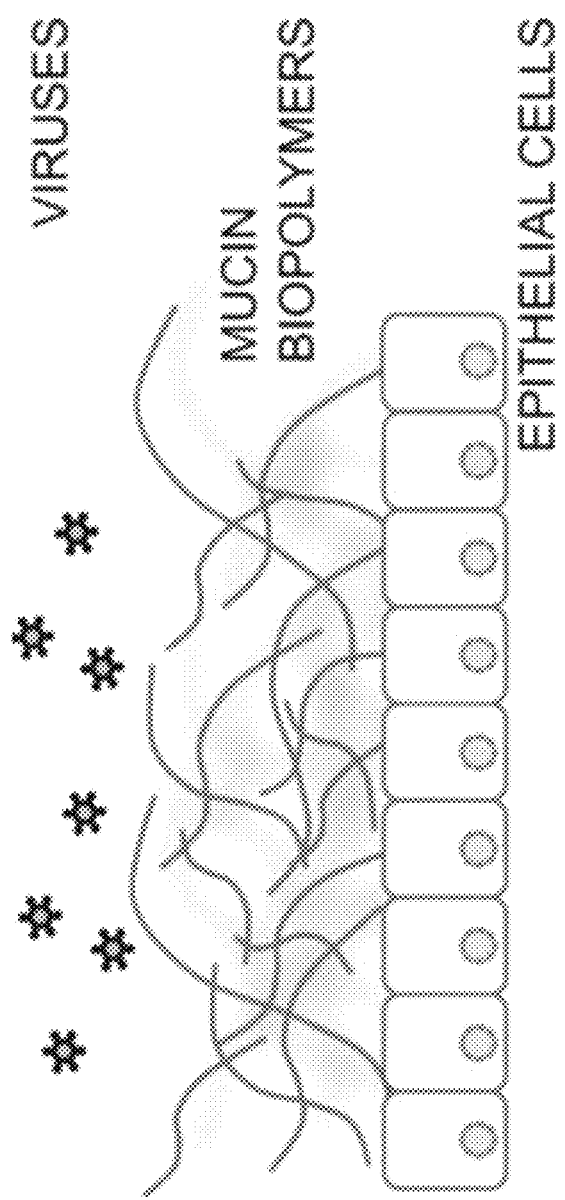

FIG. 2B
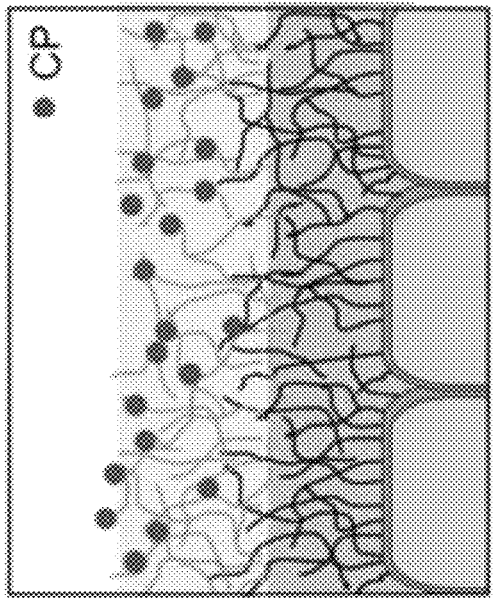
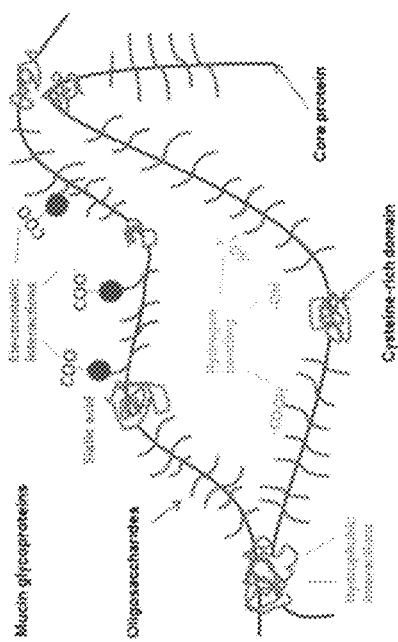
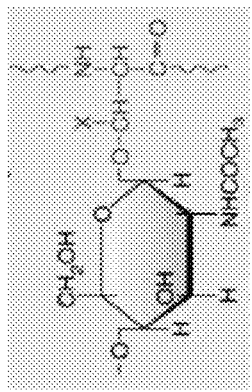
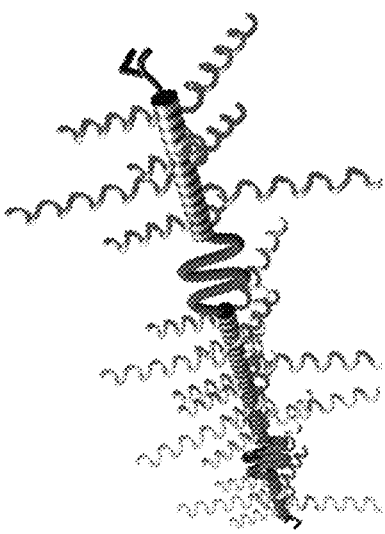
Pathogen Inhibition
Clearance and Lubrication
Functionality
Charge
Size and Structure

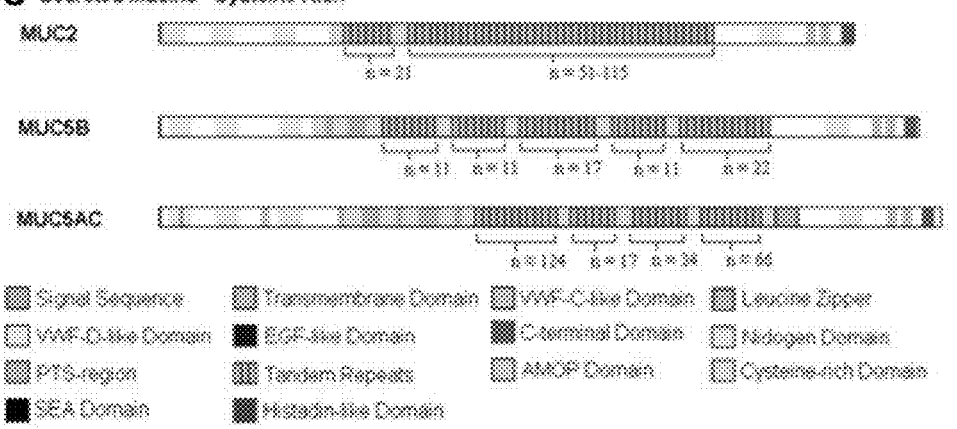

FIG. 4

| Protein Name | Sequence | Vector |
|---|---|---|
| MUC5ACL | CAS(YTSTYSAP)$_{46}$TSC | pET15b |
| MUC5ACH | CAS(TYSTTYAP)$_{46}$TSC | pET15b |
| MUC5BL | CAS(HYPYVLYTTATYYAATGSYAYPSSTPGTY)$_{12}$TSC | pET15b |
| MUC5BH | CAS(HTPTVLTYYAYTAAPYYTPGYD)$_{12}$TSC | pET15b |
| MUC5ACL-S | CAS(YTSTYSAP)$_{30}$TSC | pET21a |
| MUC5ACL-LT | CAS(TTSTYSAP)$_{46}$TSC | pET21a |
| MUC5ACL+D | CAS(YTSTYSAPD)$_{46}$TSC | pET21a |

FIG. 5A

| T (74%) | T (81%) | S (82%) | T (76%) | T (69%) | A (54%) | P (75%) |
|---|---|---|---|---|---|---|
| G (12%) | S (10%) | T (13%) | P (11%) | S (15%) | V (14%) | S (12%) |
| Q (8%) | A (6%) | P (1%) | I (5%) | I (11%) | G (13%) | A (3%) |

FIG. 5B

| H | T | P | T | V | L | T | T | A | T | G | S | T | P | S | S | T | P | G | T | T |
|---|---|---|---|---|---|---|---|---|---|---|---|---|---|---|---|---|---|---|---|---|
| (35) | (53) | (40) | (60) | (53) | (78) | (75) | (85) | (88) | (100) | (55) | (28) | (75) | (100) | (60) | (88) | (78) | (68) | (83) | (68) | (100) | (60) |
| W | I | L | P | E | P | S | S | A | T | V | P | T | S | S | P | V | T | N | A | T | A |
| (33) | (40) | (35) | (38) | (25) | (20) | (13) | (5) | (8) | | (8) | (18) | (25) | (13) | (33) | (5) | (13) | (13) | (13) | (8) | (10) | (20) | (35) |
| P | P | S | K | S | O | N | A | K | | | K | I | G | T | N | M | V | I | L | S | Q | E | S |
| (13) | (3) | (20) | (3) | (13) | (10) | (3) | (5) | (5) | | | (5) | (13) | (18) | (3) | (3) | (8) | (10) | (8) | (3) | (8) | (8) | (5) | (5) |

AA analysis

FIG. 15

| Protein Name | Sequence | Vector |
|---|---|---|
| MUC5ACLS-15 pCoil-MUC5ACL-S | CAS(YTSTYSAP)$_{30}$TSC pCoilcoil-mini intein – CAS(YTSTYSAP)$_{30}$TSC | pET15b pET21a |
| pCoil-MUC5ACL-LT | pCoilcoil-mini intein – CAS(TTSTYSAP)$_{46}$TSC | pET21a |
| pCoil-MUC5ACL+D | pCoilcoil-mini intein – CAS(YTSTYSAPD)$_{46}$TSC | pET21a |

| Protein Name | Sequence | Vector |
|---|---|---|
| MUC5ACL-S-Cold | CAS(YTSTYSAP)₃₀TSC | pColdI |
| GST-MUC5ACL-S | GST-mini intein – CAS(YTSTYSAP)₃₀TSC-Histag | pGEX-4T1 |
| MBP-MUC5ACL-S | MBP-mini intein – CAS(YTSTYSAP)₃₀TSC-Histag | pMAL-c5E |

FIG. 20
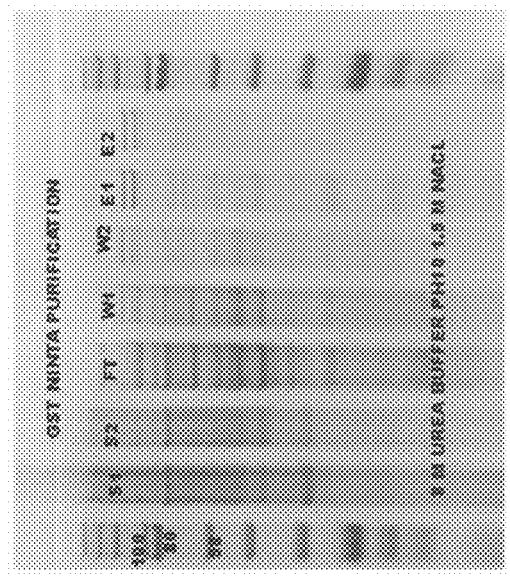 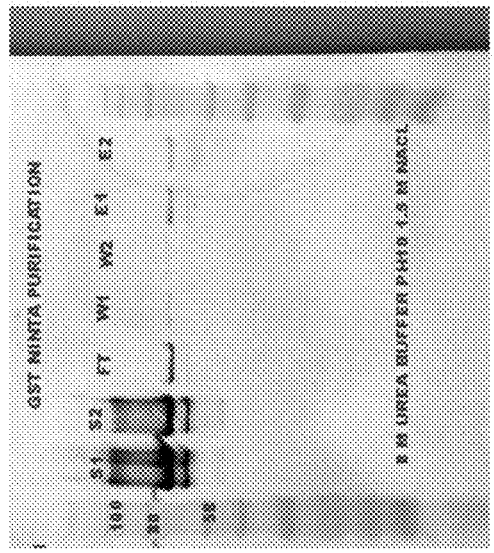

FIG. 22

| Protein Name | Sequence | Vector |
|---|---|---|
| ELP1:1Y:S 10k | (VPGSG VPGYG)$_{11}$ | pET15b |
| ELP3:1Y:S 10k | [VPGSG (VPGYG)$_3$]$_6$ | pET15b |
| MUC5ACLSS | CAS(YTSTYSAP)$_{14}$TSC | pET15b |

FIG. 27
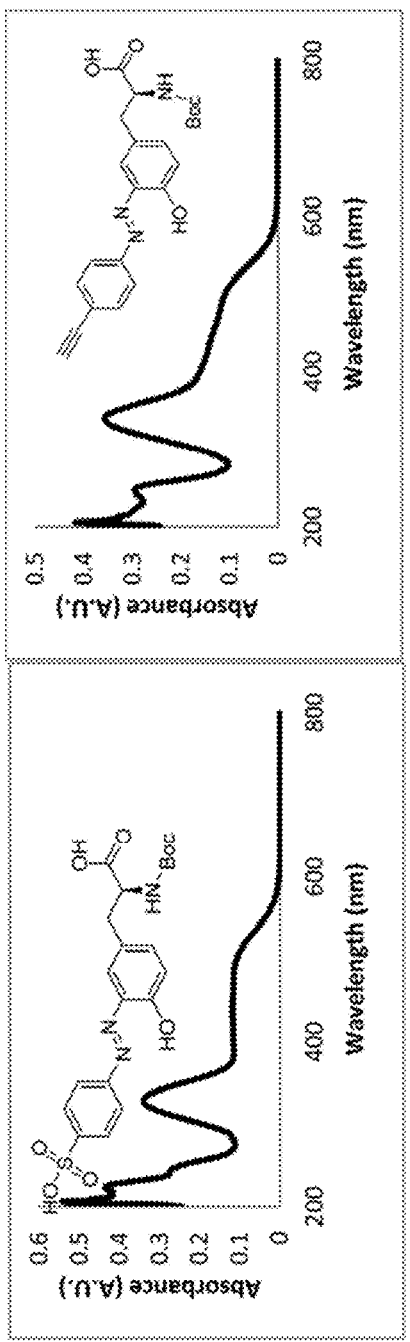
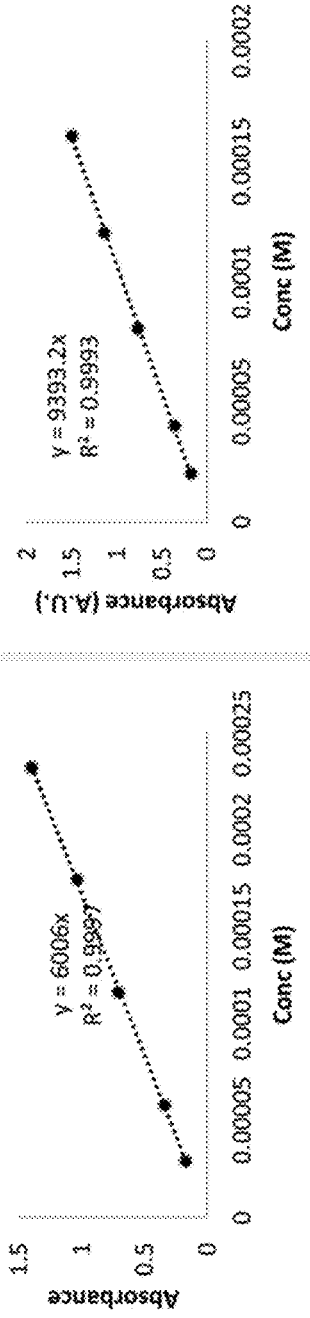

SEQUENCE LISTING

```
<160> NUMBER OF SEQ ID NOS: 17

<210> SEQ ID NO 1
<211> LENGTH: 368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Tyr Thr Ser Thr Tyr Ser Ala Pro Tyr Thr Ser Thr Tyr Ser Ala Pro
1               5                   10                  15

Tyr Thr Ser Thr Tyr Ser Ala Pro Tyr Thr Ser Thr Tyr Ser Ala Pro
            20                  25                  30

Tyr Thr Ser Thr Tyr Ser Ala Pro Tyr Thr Ser Thr Tyr Ser Ala Pro
        35                  40                  45

Tyr Thr Ser Thr Tyr Ser Ala Pro Tyr Thr Ser Thr Tyr Ser Ala Pro
    50                  55                  60

Tyr Thr Ser Thr Tyr Ser Ala Pro Tyr Thr Ser Thr Tyr Ser Ala Pro
65                  70                  75                  80

Tyr Thr Ser Thr Tyr Ser Ala Pro Tyr Thr Ser Thr Tyr Ser Ala Pro
                85                  90                  95

Tyr Thr Ser Thr Tyr Ser Ala Pro Tyr Thr Ser Thr Tyr Ser Ala Pro
            100                 105                 110

Tyr Thr Ser Thr Tyr Ser Ala Pro Tyr Thr Ser Thr Tyr Ser Ala Pro
        115                 120                 125

Tyr Thr Ser Thr Tyr Ser Ala Pro Tyr Thr Ser Thr Tyr Ser Ala Pro
    130                 135                 140

Tyr Thr Ser Thr Tyr Ser Ala Pro Tyr Thr Ser Thr Tyr Ser Ala Pro
145                 150                 155                 160

Tyr Thr Ser Thr Tyr Ser Ala Pro Tyr Thr Ser Thr Tyr Ser Ala Pro
                165                 170                 175

Tyr Thr Ser Thr Tyr Ser Ala Pro Tyr Thr Ser Thr Tyr Ser Ala Pro
            180                 185                 190

Tyr Thr Ser Thr Tyr Ser Ala Pro Tyr Thr Ser Thr Tyr Ser Ala Pro
        195                 200                 205

Tyr Thr Ser Thr Tyr Ser Ala Pro Tyr Thr Ser Thr Tyr Ser Ala Pro
```

```
            210                 215                 220
Tyr Thr Ser Thr Tyr Ser Ala Pro Tyr Thr Ser Thr Tyr Ser Ala Pro
225                 230                 235                 240

Tyr Thr Ser Thr Tyr Ser Ala Pro Tyr Thr Ser Thr Tyr Ser Ala Pro
            245                 250                 255

Tyr Thr Ser Thr Tyr Ser Ala Pro Tyr Thr Ser Thr Tyr Ser Ala Pro
            260                 265                 270

Tyr Thr Ser Thr Tyr Ser Ala Pro Tyr Thr Ser Thr Tyr Ser Ala Pro
            275                 280                 285

Tyr Thr Ser Thr Tyr Ser Ala Pro Tyr Thr Ser Thr Tyr Ser Ala Pro
            290                 295                 300

Tyr Thr Ser Thr Tyr Ser Ala Pro Tyr Thr Ser Thr Tyr Ser Ala Pro
305                 310                 315                 320

Tyr Thr Ser Thr Tyr Ser Ala Pro Tyr Thr Ser Thr Tyr Ser Ala Pro
            325                 330                 335

Tyr Thr Ser Thr Tyr Ser Ala Pro Tyr Thr Ser Thr Tyr Ser Ala Pro
            340                 345                 350

Tyr Thr Ser Thr Tyr Ser Ala Pro Tyr Thr Ser Thr Tyr Ser Ala Pro
            355                 360                 365

<210> SEQ ID NO 2
<211> LENGTH: 374
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: MUC5ACL

<400> SEQUENCE: 2

Cys Ala Ser Tyr Thr Ser Thr Tyr Ser Ala Pro Tyr Thr Ser Thr Tyr
1               5                   10                  15

Ser Ala Pro Tyr Thr Ser Thr Tyr Ser Ala Pro Tyr Thr Ser Thr Tyr
            20                  25                  30

Ser Ala Pro Tyr Thr Ser Thr Tyr Ser Ala Pro Tyr Thr Ser Thr Tyr
        35                  40                  45

Ser Ala Pro Tyr Thr Ser Thr Tyr Ser Ala Pro Tyr Thr Ser Thr Tyr
    50                  55                  60

Ser Ala Pro Tyr Thr Ser Thr Tyr Ser Ala Pro Tyr Thr Ser Thr Tyr
65                  70                  75                  80

Ser Ala Pro Tyr Thr Ser Thr Tyr Ser Ala Pro Tyr Thr Ser Thr Tyr
            85                  90                  95

Ser Ala Pro Tyr Thr Ser Thr Tyr Ser Ala Pro Tyr Thr Ser Thr Tyr
        100                 105                 110

Ser Ala Pro Tyr Thr Ser Thr Tyr Ser Ala Pro Tyr Thr Ser Thr Tyr
    115                 120                 125

Ser Ala Pro Tyr Thr Ser Thr Tyr Ser Ala Pro Tyr Thr Ser Thr Tyr
130                 135                 140

Ser Ala Pro Tyr Thr Ser Thr Tyr Ser Ala Pro Tyr Thr Ser Thr Tyr
145                 150                 155                 160

Ser Ala Pro Tyr Thr Ser Thr Tyr Ser Ala Pro Tyr Thr Ser Thr Tyr
            165                 170                 175

Ser Ala Pro Tyr Thr Ser Thr Tyr Ser Ala Pro Tyr Thr Ser Thr Tyr
        180                 185                 190

Ser Ala Pro Tyr Thr Ser Thr Tyr Ser Ala Pro Tyr Thr Ser Thr Tyr
```

-continued

```
                195                 200                 205
Ser Ala Pro Tyr Thr Ser Thr Tyr Ser Ala Pro Tyr Thr Ser Thr Tyr
210                 215                 220

Ser Ala Pro Tyr Thr Ser Thr Tyr Ser Ala Pro Tyr Thr Ser Thr Tyr
225                 230                 235                 240

Ser Ala Pro Tyr Thr Ser Thr Tyr Ser Ala Pro Tyr Thr Ser Thr Tyr
                245                 250                 255

Ser Ala Pro Tyr Thr Ser Thr Tyr Ser Ala Pro Tyr Thr Ser Thr Tyr
            260                 265                 270

Ser Ala Pro Tyr Thr Ser Thr Tyr Ser Ala Pro Tyr Thr Ser Thr Tyr
        275                 280                 285

Ser Ala Pro Tyr Thr Ser Thr Tyr Ser Ala Pro Tyr Thr Ser Thr Tyr
    290                 295                 300

Ser Ala Pro Tyr Thr Ser Thr Tyr Ser Ala Pro Tyr Thr Ser Thr Tyr
305                 310                 315                 320

Ser Ala Pro Tyr Thr Ser Thr Tyr Ser Ala Pro Tyr Thr Ser Thr Tyr
                325                 330                 335

Ser Ala Pro Tyr Thr Ser Thr Tyr Ser Ala Pro Tyr Thr Ser Thr Tyr
            340                 345                 350

Ser Ala Pro Tyr Thr Ser Thr Tyr Ser Ala Pro Tyr Thr Ser Thr Tyr
        355                 360                 365

Ser Ala Pro Thr Ser Cys
    370

<210> SEQ ID NO 3
<211> LENGTH: 374
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: MUC5ACH

<400> SEQUENCE: 3

Cys Ala Ser Thr Tyr Ser Thr Thr Tyr Ala Pro Thr Tyr Ser Thr Thr
1               5                   10                  15

Tyr Ala Pro Thr Tyr Ser Thr Thr Tyr Ala Pro Thr Tyr Ser Thr Thr
                20                  25                  30

Tyr Ala Pro Thr Tyr Ser Thr Thr Tyr Ala Pro Thr Tyr Ser Thr Thr
            35                  40                  45

Tyr Ala Pro Thr Tyr Ser Thr Thr Tyr Ala Pro Thr Tyr Ser Thr Thr
50                  55                  60

Tyr Ala Pro Thr Tyr Ser Thr Thr Tyr Ala Pro Thr Tyr Ser Thr Thr
65                  70                  75                  80

Tyr Ala Pro Thr Tyr Ser Thr Thr Tyr Ala Pro Thr Tyr Ser Thr Thr
                85                  90                  95

Tyr Ala Pro Thr Tyr Ser Thr Thr Tyr Ala Pro Thr Tyr Ser Thr Thr
            100                 105                 110

Tyr Ala Pro Thr Tyr Ser Thr Thr Tyr Ala Pro Thr Tyr Ser Thr Thr
        115                 120                 125

Tyr Ala Pro Thr Tyr Ser Thr Thr Tyr Ala Pro Thr Tyr Ser Thr Thr
    130                 135                 140

Tyr Ala Pro Thr Tyr Ser Thr Thr Tyr Ala Pro Thr Tyr Ser Thr Thr
145                 150                 155                 160

Tyr Ala Pro Thr Tyr Ser Thr Thr Tyr Ala Pro Thr Tyr Ser Thr Thr
```

```
                165                 170                 175
Tyr Ala Pro Thr Tyr Ser Thr Thr Tyr Ala Pro Thr Tyr Ser Thr Thr
            180                 185                 190

Tyr Ala Pro Thr Tyr Ser Thr Thr Tyr Ala Pro Thr Tyr Ser Thr Thr
        195                 200                 205

Tyr Ala Pro Thr Tyr Ser Thr Thr Tyr Ala Pro Thr Tyr Ser Thr Thr
    210                 215                 220

Tyr Ala Pro Thr Tyr Ser Thr Thr Tyr Ala Pro Thr Tyr Ser Thr Thr
225                 230                 235                 240

Tyr Ala Pro Thr Tyr Ser Thr Thr Tyr Ala Pro Thr Tyr Ser Thr Thr
                245                 250                 255

Tyr Ala Pro Thr Tyr Ser Thr Thr Tyr Ala Pro Thr Tyr Ser Thr Thr
            260                 265                 270

Tyr Ala Pro Thr Tyr Ser Thr Thr Tyr Ala Pro Thr Tyr Ser Thr Thr
        275                 280                 285

Tyr Ala Pro Thr Tyr Ser Thr Thr Tyr Ala Pro Thr Tyr Ser Thr Thr
    290                 295                 300

Tyr Ala Pro Thr Tyr Ser Thr Thr Tyr Ala Pro Thr Tyr Ser Thr Thr
305                 310                 315                 320

Tyr Ala Pro Thr Tyr Ser Thr Thr Tyr Ala Pro Thr Tyr Ser Thr Thr
                325                 330                 335

Tyr Ala Pro Thr Tyr Ser Thr Thr Tyr Ala Pro Thr Tyr Ser Thr Thr
            340                 345                 350

Tyr Ala Pro Thr Tyr Ser Thr Thr Tyr Ala Pro Thr Tyr Ser Thr Thr
        355                 360                 365

Tyr Ala Pro Thr Ser Cys
    370

<210> SEQ ID NO 4
<211> LENGTH: 354
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: MUC5BL

<400> SEQUENCE: 4

Cys Ala Ser His Tyr Pro Tyr Val Leu Tyr Thr Thr Ala Thr Tyr Tyr
1               5                   10                  15

Ala Ala Thr Gly Ser Tyr Ala Tyr Pro Ser Ser Thr Pro Gly Thr Tyr
            20                  25                  30

His Tyr Pro Tyr Val Leu Tyr Thr Thr Ala Thr Tyr Tyr Ala Ala Thr
        35                  40                  45

Gly Ser Tyr Ala Tyr Pro Ser Ser Thr Pro Gly Thr Tyr His Tyr Pro
    50                  55                  60

Tyr Val Leu Tyr Thr Thr Ala Thr Tyr Tyr Ala Ala Thr Gly Ser Tyr
65                  70                  75                  80

Ala Tyr Pro Ser Ser Thr Pro Gly Thr Tyr His Tyr Pro Tyr Val Leu
                85                  90                  95

Tyr Thr Thr Ala Thr Tyr Tyr Ala Ala Thr Gly Ser Tyr Ala Tyr Pro
            100                 105                 110

Ser Ser Thr Pro Gly Thr Tyr His Tyr Pro Tyr Val Leu Tyr Thr Thr
        115                 120                 125

Ala Thr Tyr Tyr Ala Ala Thr Gly Ser Tyr Ala Tyr Pro Ser Ser Thr
```

```
                130                 135                 140
Pro Gly Thr Tyr His Tyr Pro Tyr Val Leu Tyr Thr Thr Ala Thr Tyr
145                 150                 155                 160

Tyr Ala Ala Thr Gly Ser Tyr Ala Tyr Pro Ser Ser Thr Pro Gly Thr
                165                 170                 175

Tyr His Tyr Pro Tyr Val Leu Tyr Thr Thr Ala Thr Tyr Tyr Ala Ala
                180                 185                 190

Thr Gly Ser Tyr Ala Tyr Pro Ser Ser Thr Pro Gly Thr Tyr His Tyr
                195                 200                 205

Pro Tyr Val Leu Tyr Thr Thr Ala Thr Tyr Tyr Ala Ala Thr Gly Ser
                210                 215                 220

Tyr Ala Tyr Pro Ser Ser Thr Pro Gly Thr Tyr His Tyr Pro Tyr Val
225                 230                 235                 240

Leu Tyr Thr Thr Ala Thr Tyr Tyr Ala Ala Thr Gly Ser Tyr Ala Tyr
                245                 250                 255

Pro Ser Ser Thr Pro Gly Thr Tyr His Tyr Pro Tyr Val Leu Tyr Thr
                260                 265                 270

Thr Ala Thr Tyr Tyr Ala Ala Thr Gly Ser Tyr Ala Tyr Pro Ser Ser
                275                 280                 285

Thr Pro Gly Thr Tyr His Tyr Pro Tyr Val Leu Tyr Thr Thr Ala Thr
                290                 295                 300

Tyr Tyr Ala Ala Thr Gly Ser Tyr Ala Tyr Pro Ser Ser Thr Pro Gly
305                 310                 315                 320

Thr Tyr His Tyr Pro Tyr Val Leu Tyr Thr Thr Ala Thr Tyr Tyr Ala
                325                 330                 335

Ala Thr Gly Ser Tyr Ala Tyr Pro Ser Ser Thr Pro Gly Thr Tyr Thr
                340                 345                 350

Ser Cys

<210> SEQ ID NO 5
<211> LENGTH: 354
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: MUC5BH

<400> SEQUENCE: 5

Cys Ala Ser His Thr Pro Thr Val Leu Thr Tyr Tyr Ala Tyr Thr Thr
1               5                   10                  15

Ala Ala Tyr Gly Tyr Thr Ala Ala Pro Tyr Tyr Thr Pro Gly Tyr Thr
                20                  25                  30

His Thr Pro Thr Val Leu Thr Tyr Tyr Ala Tyr Thr Thr Ala Ala Tyr
                35                  40                  45

Gly Tyr Thr Ala Ala Pro Tyr Tyr Thr Pro Gly Tyr Thr His Thr Pro
                50                  55                  60

Thr Val Leu Thr Tyr Tyr Ala Tyr Thr Thr Ala Ala Tyr Gly Tyr Thr
65                  70                  75                  80

Ala Ala Pro Tyr Tyr Thr Pro Gly Tyr Thr His Thr Pro Thr Val Leu
                85                  90                  95

Thr Tyr Tyr Ala Tyr Thr Thr Ala Ala Tyr Gly Tyr Thr Ala Ala Pro
                100                 105                 110

Tyr Tyr Thr Pro Gly Tyr Thr His Thr Pro Thr Val Leu Thr Tyr Tyr
                115                 120                 125
```

```
Ala Tyr Thr Thr Ala Ala Tyr Gly Tyr Thr Ala Ala Pro Tyr Tyr Thr
    130                 135                 140

Pro Gly Tyr Thr His Thr Pro Thr Val Leu Thr Tyr Tyr Ala Tyr Thr
145                 150                 155                 160

Thr Ala Ala Tyr Gly Tyr Thr Ala Ala Pro Tyr Tyr Thr Pro Gly Tyr
                165                 170                 175

Thr His Thr Pro Thr Val Leu Thr Tyr Tyr Ala Tyr Thr Thr Ala Ala
            180                 185                 190

Tyr Gly Tyr Thr Ala Ala Pro Tyr Tyr Thr Pro Gly Tyr Thr His Thr
        195                 200                 205

Pro Thr Val Leu Thr Tyr Tyr Ala Tyr Thr Thr Ala Ala Tyr Gly Tyr
    210                 215                 220

Thr Ala Ala Pro Tyr Tyr Thr Pro Gly Tyr Thr His Thr Pro Thr Val
225                 230                 235                 240

Leu Thr Tyr Tyr Ala Tyr Thr Thr Ala Ala Tyr Gly Tyr Thr Ala Ala
                245                 250                 255

Pro Tyr Tyr Thr Pro Gly Tyr Thr His Thr Pro Thr Val Leu Thr Tyr
            260                 265                 270

Tyr Ala Tyr Thr Thr Ala Ala Tyr Gly Tyr Thr Ala Ala Pro Tyr Tyr
        275                 280                 285

Thr Pro Gly Tyr Thr His Thr Pro Thr Val Leu Thr Tyr Tyr Ala Tyr
    290                 295                 300

Thr Thr Ala Ala Tyr Gly Tyr Thr Ala Ala Pro Tyr Tyr Thr Pro Gly
305                 310                 315                 320

Tyr Thr His Thr Pro Thr Val Leu Thr Tyr Tyr Ala Tyr Thr Thr Ala
                325                 330                 335

Ala Tyr Gly Tyr Thr Ala Ala Pro Tyr Tyr Thr Pro Gly Tyr Thr Thr
            340                 345                 350

Ser Cys

<210> SEQ ID NO 6
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: MUC5ACL-S, MUC5ACLS-15, pCoil-MUC5ACL-S,
      MUC5ACL-S-Cold, GST-MUC5ACL-S, and MBP-MUC5ACL-S

<400> SEQUENCE: 6

Cys Ala Ser Tyr Thr Ser Thr Tyr Ser Ala Pro Tyr Thr Ser Thr Tyr
1               5                   10                  15

Ser Ala Pro Tyr Thr Ser Thr Tyr Ser Ala Pro Tyr Thr Ser Thr Tyr
            20                  25                  30

Ser Ala Pro Tyr Thr Ser Thr Tyr Ser Ala Pro Tyr Thr Ser Thr Tyr
        35                  40                  45

Ser Ala Pro Tyr Thr Ser Thr Tyr Ser Ala Pro Tyr Thr Ser Thr Tyr
    50                  55                  60

Ser Ala Pro Tyr Thr Ser Thr Tyr Ser Ala Pro Tyr Thr Ser Thr Tyr
65                  70                  75                  80

Ser Ala Pro Tyr Thr Ser Thr Tyr Ser Ala Pro Tyr Thr Ser Thr Tyr
                85                  90                  95

Ser Ala Pro Tyr Thr Ser Thr Tyr Ser Ala Pro Tyr Thr Ser Thr Tyr
            100                 105                 110
```

```
Ser Ala Pro Tyr Thr Ser Thr Tyr Ser Ala Pro Tyr Thr Ser Thr Tyr
            115                 120                 125

Ser Ala Pro Tyr Thr Ser Thr Tyr Ser Ala Pro Tyr Thr Ser Thr Tyr
        130                 135                 140

Ser Ala Pro Tyr Thr Ser Thr Tyr Ser Ala Pro Tyr Thr Ser Thr Tyr
145                 150                 155                 160

Ser Ala Pro Tyr Thr Ser Thr Tyr Ser Ala Pro Tyr Thr Ser Thr Tyr
                165                 170                 175

Ser Ala Pro Tyr Thr Ser Thr Tyr Ser Ala Pro Tyr Thr Ser Thr Tyr
            180                 185                 190

Ser Ala Pro Tyr Thr Ser Thr Tyr Ser Ala Pro Tyr Thr Ser Thr Tyr
        195                 200                 205

Ser Ala Pro Tyr Thr Ser Thr Tyr Ser Ala Pro Tyr Thr Ser Thr Tyr
210                 215                 220

Ser Ala Pro Tyr Thr Ser Thr Tyr Ser Ala Pro Tyr Thr Ser Thr Tyr
225                 230                 235                 240

Ser Ala Pro Thr Ser Cys
            245

<210> SEQ ID NO 7
<211> LENGTH: 374
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: MUC5ACL-LT and pCoil-MUC5ACL-LT

<400> SEQUENCE: 7

Cys Ala Ser Thr Thr Ser Thr Tyr Ser Ala Pro Thr Thr Ser Thr Tyr
1               5                   10                  15

Ser Ala Pro Thr Thr Ser Thr Tyr Ser Ala Pro Thr Thr Ser Thr Tyr
            20                  25                  30

Ser Ala Pro Thr Thr Ser Thr Tyr Ser Ala Pro Thr Thr Ser Thr Tyr
        35                  40                  45

Ser Ala Pro Thr Thr Ser Thr Tyr Ser Ala Pro Thr Thr Ser Thr Tyr
    50                  55                  60

Ser Ala Pro Thr Thr Ser Thr Tyr Ser Ala Pro Thr Thr Ser Thr Tyr
65                  70                  75                  80

Ser Ala Pro Thr Thr Ser Thr Tyr Ser Ala Pro Thr Thr Ser Thr Tyr
                85                  90                  95

Ser Ala Pro Thr Thr Ser Thr Tyr Ser Ala Pro Thr Thr Ser Thr Tyr
            100                 105                 110

Ser Ala Pro Thr Thr Ser Thr Tyr Ser Ala Pro Thr Thr Ser Thr Tyr
        115                 120                 125

Ser Ala Pro Thr Thr Ser Thr Tyr Ser Ala Pro Thr Thr Ser Thr Tyr
    130                 135                 140

Ser Ala Pro Thr Thr Ser Thr Tyr Ser Ala Pro Thr Thr Ser Thr Tyr
145                 150                 155                 160

Ser Ala Pro Thr Thr Ser Thr Tyr Ser Ala Pro Thr Thr Ser Thr Tyr
                165                 170                 175

Ser Ala Pro Thr Thr Ser Thr Tyr Ser Ala Pro Thr Thr Ser Thr Tyr
            180                 185                 190

Ser Ala Pro Thr Thr Ser Thr Tyr Ser Ala Pro Thr Thr Ser Thr Tyr
        195                 200                 205
```

-continued

Ser Ala Pro Thr Thr Ser Thr Tyr Ser Ala Pro Thr Thr Ser Thr Tyr
            210                 215                 220

Ser Ala Pro Thr Thr Ser Thr Tyr Ser Ala Pro Thr Thr Ser Thr Tyr
225                 230                 235                 240

Ser Ala Pro Thr Thr Ser Thr Tyr Ser Ala Pro Thr Thr Ser Thr Tyr
            245                 250                 255

Ser Ala Pro Thr Thr Ser Thr Tyr Ser Ala Pro Thr Thr Ser Thr Tyr
            260                 265                 270

Ser Ala Pro Thr Thr Ser Thr Tyr Ser Ala Pro Thr Thr Ser Thr Tyr
            275                 280                 285

Ser Ala Pro Thr Thr Ser Thr Tyr Ser Ala Pro Thr Thr Ser Thr Tyr
            290                 295                 300

Ser Ala Pro Thr Thr Ser Thr Tyr Ser Ala Pro Thr Thr Ser Thr Tyr
305                 310                 315                 320

Ser Ala Pro Thr Thr Ser Thr Tyr Ser Ala Pro Thr Thr Ser Thr Tyr
            325                 330                 335

Ser Ala Pro Thr Thr Ser Thr Tyr Ser Ala Pro Thr Thr Ser Thr Tyr
            340                 345                 350

Ser Ala Pro Thr Thr Ser Thr Tyr Ser Ala Pro Thr Thr Ser Thr Tyr
            355                 360                 365

Ser Ala Pro Thr Ser Cys
    370

<210> SEQ ID NO 8
<211> LENGTH: 420
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: MUC5ACL+D and pCoil-MUC5ACL+D

<400> SEQUENCE: 8

Cys Ala Ser Tyr Thr Ser Thr Tyr Ser Ala Pro Asp Tyr Thr Ser Thr
1               5                   10                  15

Tyr Ser Ala Pro Asp Tyr Thr Ser Thr Tyr Ser Ala Pro Asp Tyr Thr
            20                  25                  30

Ser Thr Tyr Ser Ala Pro Asp Tyr Thr Ser Thr Tyr Ser Ala Pro Asp
        35                  40                  45

Tyr Thr Ser Thr Tyr Ser Ala Pro Asp Tyr Thr Ser Thr Tyr Ser Ala
    50                  55                  60

Pro Asp Tyr Thr Ser Thr Tyr Ser Ala Pro Asp Tyr Thr Ser Thr Tyr
65                  70                  75                  80

Ser Ala Pro Asp Tyr Thr Ser Thr Tyr Ser Ala Pro Asp Tyr Thr Ser
            85                  90                  95

Thr Tyr Ser Ala Pro Asp Tyr Thr Ser Thr Tyr Ser Ala Pro Asp Tyr
            100                 105                 110

Thr Ser Thr Tyr Ser Ala Pro Asp Tyr Thr Ser Thr Tyr Ser Ala Pro
        115                 120                 125

Asp Tyr Thr Ser Thr Tyr Ser Ala Pro Asp Tyr Thr Ser Thr Tyr Ser
    130                 135                 140

Ala Pro Asp Tyr Thr Ser Thr Tyr Ser Ala Pro Asp Tyr Thr Ser Thr
145                 150                 155                 160

Tyr Ser Ala Pro Asp Tyr Thr Ser Thr Tyr Ser Ala Pro Asp Tyr Thr
            165                 170                 175

Ser Thr Tyr Ser Ala Pro Asp Tyr Thr Ser Thr Tyr Ser Ala Pro Asp
            180                 185                 190

Tyr Thr Ser Thr Tyr Ser Ala Pro Asp Tyr Thr Ser Thr Tyr Ser Ala
            195                 200                 205

Pro Asp Tyr Thr Ser Thr Tyr Ser Ala Pro Asp Tyr Thr Ser Thr Tyr
            210                 215                 220

Ser Ala Pro Asp Tyr Thr Ser Thr Tyr Ser Ala Pro Asp Tyr Thr Ser
225                 230                 235                 240

Thr Tyr Ser Ala Pro Asp Tyr Thr Ser Thr Tyr Ser Ala Pro Asp Tyr
            245                 250                 255

Thr Ser Thr Tyr Ser Ala Pro Asp Tyr Thr Ser Thr Tyr Ser Ala Pro
            260                 265                 270

Asp Tyr Thr Ser Thr Tyr Ser Ala Pro Asp Tyr Thr Ser Thr Tyr Ser
            275                 280                 285

Ala Pro Asp Tyr Thr Ser Thr Tyr Ser Ala Pro Asp Tyr Thr Ser Thr
            290                 295                 300

Tyr Ser Ala Pro Asp Tyr Thr Ser Thr Tyr Ser Ala Pro Asp Tyr Thr
305                 310                 315                 320

Ser Thr Tyr Ser Ala Pro Asp Tyr Thr Ser Thr Tyr Ser Ala Pro Asp
            325                 330                 335

Tyr Thr Ser Thr Tyr Ser Ala Pro Asp Tyr Thr Ser Thr Tyr Ser Ala
            340                 345                 350

Pro Asp Tyr Thr Ser Thr Tyr Ser Ala Pro Asp Tyr Thr Ser Thr Tyr
            355                 360                 365

Ser Ala Pro Asp Tyr Thr Ser Thr Tyr Ser Ala Pro Asp Tyr Thr Ser
            370                 375                 380

Thr Tyr Ser Ala Pro Asp Tyr Thr Ser Thr Tyr Ser Ala Pro Asp Tyr
385                 390                 395                 400

Thr Ser Thr Tyr Ser Ala Pro Asp Tyr Thr Ser Thr Tyr Ser Ala Pro
            405                 410                 415

Asp Thr Ser Cys
            420

<210> SEQ ID NO 9
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ELP 1:1 Y:S 10k

<400> SEQUENCE: 9

Val Pro Gly Ser Gly Val Pro Gly Tyr Gly Val Pro Gly Ser Gly Val
1               5                   10                  15

Pro Gly Tyr Gly Val Pro Gly Ser Gly Val Pro Gly Tyr Gly Val Pro
            20                  25                  30

Gly Ser Gly Val Pro Gly Tyr Gly Val Pro Gly Ser Gly Val Pro Gly
            35                  40                  45

Tyr Gly Val Pro Gly Ser Gly Val Pro Gly Tyr Gly Val Pro Gly Ser
            50                  55                  60

Gly Val Pro Gly Tyr Gly Val Pro Gly Ser Gly Val Pro Gly Tyr Gly
65                  70                  75                  80

Val Pro Gly Ser Gly Val Pro Gly Tyr Gly Val Pro Gly Ser Gly Val
            85                  90                  95

-continued

Pro Gly Tyr Gly Val Pro Gly Ser Gly Val Pro Gly Tyr Gly
            100                 105                 110

<210> SEQ ID NO 10
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ELP 3:1 Y:S 10k

<400> SEQUENCE: 10

Val Pro Gly Ser Gly Val Pro Gly Tyr Gly Val Pro Gly Tyr Gly Val
1               5                   10                  15

Pro Gly Tyr Gly Val Pro Gly Ser Gly Val Pro Gly Tyr Gly Val Pro
            20                  25                  30

Gly Tyr Gly Val Pro Gly Tyr Gly Val Pro Gly Ser Gly Val Pro Gly
        35                  40                  45

Tyr Gly Val Pro Gly Tyr Gly Val Pro Gly Tyr Gly Val Pro Gly Ser
    50                  55                  60

Gly Val Pro Gly Tyr Gly Val Pro Gly Tyr Gly Val Pro Gly Tyr Gly
65                  70                  75                  80

Val Pro Gly Ser Gly Val Pro Gly Tyr Gly Val Pro Gly Tyr Gly Val
                85                  90                  95

Pro Gly Tyr Gly Val Pro Gly Ser Gly Val Pro Gly Tyr Gly Val Pro
            100                 105                 110

Gly Tyr Gly Val Pro Gly Tyr Gly
        115                 120

<210> SEQ ID NO 11
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: MUC5ACLSS

<400> SEQUENCE: 11

Cys Ala Ser Tyr Thr Ser Thr Tyr Ser Ala Pro Tyr Thr Ser Thr Tyr
1               5                   10                  15

Ser Ala Pro Tyr Thr Ser Thr Tyr Ser Ala Pro Tyr Thr Ser Thr Tyr
            20                  25                  30

Ser Ala Pro Tyr Thr Ser Thr Tyr Ser Ala Pro Tyr Thr Ser Thr Tyr
        35                  40                  45

Ser Ala Pro Tyr Thr Ser Thr Tyr Ser Ala Pro Tyr Thr Ser Thr Tyr
    50                  55                  60

Ser Ala Pro Tyr Thr Ser Thr Tyr Ser Ala Pro Tyr Thr Ser Thr Tyr
65                  70                  75                  80

Ser Ala Pro Tyr Thr Ser Thr Tyr Ser Ala Pro Tyr Thr Ser Thr Tyr
                85                  90                  95

Ser Ala Pro Tyr Thr Ser Thr Tyr Ser Ala Pro Tyr Thr Ser Thr Tyr
            100                 105                 110

Ser Ala Pro Thr Ser Cys
        115

<210> SEQ ID NO 12
<211> LENGTH: 1255
<212> TYPE: PRT
<213> ORGANISM: Homo sapiens
<220> FEATURE:
<223> OTHER INFORMATION: MUC1

<400> SEQUENCE: 12

```
Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Val Ser Met Thr Ser Ser Val Leu Ser Ser His
    50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
        115                 120                 125

Gly Ser Thr Ala Pro Pro Ala His Gly Val Thr Ser Ala Pro Asp Thr
    130                 135                 140

Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
            180                 185                 190

Pro Pro Ala His Gly Val Thr Ser Ala Pro Asp Thr Arg Pro Ala Pro
        195                 200                 205

Gly Ser Thr Ala Pro Pro Ala His Gly Val Thr Ser Ala Pro Asp Thr
    210                 215                 220

Arg Pro Ala Pro Gly Ser Thr Ala Pro Pro Ala His Gly Val Thr Ser
225                 230                 235                 240

Ala Pro Asp Thr Arg Pro Ala Pro Gly Ser Thr Ala Pro Pro Ala His
                245                 250                 255

Gly Val Thr Ser Ala Pro Asp Thr Arg Pro Ala Pro Gly Ser Thr Ala
            260                 265                 270

Pro Pro Ala His Gly Val Thr Ser Ala Pro Asp Thr Arg Pro Ala Pro
        275                 280                 285

Gly Ser Thr Ala Pro Pro Ala His Gly Val Thr Ser Ala Pro Asp Thr
    290                 295                 300

Arg Pro Ala Pro Gly Ser Thr Ala Pro Pro Ala His Gly Val Thr Ser
305                 310                 315                 320

Ala Pro Asp Thr Arg Pro Ala Pro Gly Ser Thr Ala Pro Pro Ala His
                325                 330                 335

Gly Val Thr Ser Ala Pro Asp Thr Arg Pro Ala Pro Gly Ser Thr Ala
            340                 345                 350

Pro Pro Ala His Gly Val Thr Ser Ala Pro Asp Thr Arg Pro Ala Pro
        355                 360                 365

Gly Ser Thr Ala Pro Pro Ala His Gly Val Thr Ser Ala Pro Asp Thr
```

```
                    370                 375                 380
Arg Pro Ala Pro Gly Ser Thr Ala Pro Pro Ala His Gly Val Thr Ser
385                 390                 395                 400

Ala Pro Asp Thr Arg Pro Ala Pro Gly Ser Thr Ala Pro Pro Ala His
                405                 410                 415

Gly Val Thr Ser Ala Pro Asp Thr Arg Pro Ala Pro Gly Ser Thr Ala
                420                 425                 430

Pro Pro Ala His Gly Val Thr Ser Ala Pro Asp Thr Arg Pro Ala Pro
                435                 440                 445

Gly Ser Thr Ala Pro Pro Ala His Gly Val Thr Ser Ala Pro Asp Thr
                450                 455                 460

Arg Pro Ala Pro Gly Ser Thr Ala Pro Pro Ala His Gly Val Thr Ser
465                 470                 475                 480

Ala Pro Asp Thr Arg Pro Ala Pro Gly Ser Thr Ala Pro Pro Ala His
                485                 490                 495

Gly Val Thr Ser Ala Pro Asp Thr Arg Pro Ala Pro Gly Ser Thr Ala
                500                 505                 510

Pro Pro Ala His Gly Val Thr Ser Ala Pro Asp Thr Arg Pro Ala Pro
                515                 520                 525

Gly Ser Thr Ala Pro Pro Ala His Gly Val Thr Ser Ala Pro Asp Thr
                530                 535                 540

Arg Pro Ala Pro Gly Ser Thr Ala Pro Pro Ala His Gly Val Thr Ser
545                 550                 555                 560

Ala Pro Asp Thr Arg Pro Ala Pro Gly Ser Thr Ala Pro Pro Ala His
                565                 570                 575

Gly Val Thr Ser Ala Pro Asp Thr Arg Pro Ala Pro Gly Ser Thr Ala
                580                 585                 590

Pro Pro Ala His Gly Val Thr Ser Ala Pro Asp Thr Arg Pro Ala Pro
                595                 600                 605

Gly Ser Thr Ala Pro Pro Ala His Gly Val Thr Ser Ala Pro Asp Thr
                610                 615                 620

Arg Pro Ala Pro Gly Ser Thr Ala Pro Pro Ala His Gly Val Thr Ser
625                 630                 635                 640

Ala Pro Asp Thr Arg Pro Ala Pro Gly Ser Thr Ala Pro Pro Ala His
                645                 650                 655

Gly Val Thr Ser Ala Pro Asp Thr Arg Pro Ala Pro Gly Ser Thr Ala
                660                 665                 670

Pro Pro Ala His Gly Val Thr Ser Ala Pro Asp Thr Arg Pro Ala Pro
                675                 680                 685

Gly Ser Thr Ala Pro Pro Ala His Gly Val Thr Ser Ala Pro Asp Thr
                690                 695                 700

Arg Pro Ala Pro Gly Ser Thr Ala Pro Pro Ala His Gly Val Thr Ser
705                 710                 715                 720

Ala Pro Asp Thr Arg Pro Ala Pro Gly Ser Thr Ala Pro Pro Ala His
                725                 730                 735

Gly Val Thr Ser Ala Pro Asp Thr Arg Pro Ala Pro Gly Ser Thr Ala
                740                 745                 750

Pro Pro Ala His Gly Val Thr Ser Ala Pro Asp Thr Arg Pro Ala Pro
                755                 760                 765

Gly Ser Thr Ala Pro Pro Ala His Gly Val Thr Ser Ala Pro Asp Thr
                770                 775                 780

Arg Pro Ala Pro Gly Ser Thr Ala Pro Pro Ala His Gly Val Thr Ser
785                 790                 795                 800
```

```
Ala Pro Asp Thr Arg Pro Ala Pro Gly Ser Thr Ala Pro Ala His
                805                 810                 815

Gly Val Thr Ser Ala Pro Asp Thr Arg Pro Ala Pro Gly Ser Thr Ala
                820                 825                 830

Pro Pro Ala His Gly Val Thr Ser Ala Pro Asp Thr Arg Pro Ala Pro
            835                 840                 845

Gly Ser Thr Ala Pro Pro Ala His Gly Val Thr Ser Ala Pro Asp Thr
        850                 855                 860

Arg Pro Ala Pro Gly Ser Thr Ala Pro Pro Ala His Gly Val Thr Ser
865                 870                 875                 880

Ala Pro Asp Thr Arg Pro Ala Pro Gly Ser Thr Ala Pro Pro Ala His
                885                 890                 895

Gly Val Thr Ser Ala Pro Asp Thr Arg Pro Ala Pro Gly Ser Thr Ala
                900                 905                 910

Pro Pro Ala His Gly Val Thr Ser Ala Pro Asp Thr Arg Pro Ala Pro
            915                 920                 925

Gly Ser Thr Ala Pro Pro Ala His Gly Val Thr Ser Ala Pro Asp Asn
        930                 935                 940

Arg Pro Ala Leu Gly Ser Thr Ala Pro Pro Val His Asn Val Thr Ser
945                 950                 955                 960

Ala Ser Gly Ser Ala Ser Gly Ser Ala Ser Thr Leu Val His Asn Gly
                965                 970                 975

Thr Ser Ala Arg Ala Thr Thr Thr Pro Ala Ser Lys Ser Thr Pro Phe
                980                 985                 990

Ser Ile Pro Ser His His Ser Asp Thr Pro Thr Thr Leu Ala Ser His
                995                 1000                1005

Ser Thr Lys Thr Asp Ala Ser Ser Thr His His Ser Ser Val Pro
        1010                1015                1020

Pro Leu Thr Ser Ser Asn His Ser Thr Ser Pro Gln Leu Ser Thr
        1025                1030                1035

Gly Val Ser Phe Phe Phe Leu Ser Phe His Ile Ser Asn Leu Gln
        1040                1045                1050

Phe Asn Ser Ser Leu Glu Asp Pro Ser Thr Asp Tyr Tyr Gln Glu
        1055                1060                1065

Leu Gln Arg Asp Ile Ser Glu Met Phe Leu Gln Ile Tyr Lys Gln
        1070                1075                1080

Gly Gly Phe Leu Gly Leu Ser Asn Ile Lys Phe Arg Pro Gly Ser
        1085                1090                1095

Val Val Val Gln Leu Thr Leu Ala Phe Arg Glu Gly Thr Ile Asn
        1100                1105                1110

Val His Asp Val Glu Thr Gln Phe Asn Gln Tyr Lys Thr Glu Ala
        1115                1120                1125

Ala Ser Arg Tyr Asn Leu Thr Ile Ser Asp Val Ser Val Ser Asp
        1130                1135                1140

Val Pro Phe Pro Phe Ser Ala Gln Ser Gly Ala Gly Val Pro Gly
        1145                1150                1155

Trp Gly Ile Ala Leu Leu Val Leu Val Cys Val Leu Val Ala Leu
        1160                1165                1170

Ala Ile Val Tyr Leu Ile Ala Leu Ala Val Cys Gln Cys Arg Arg
        1175                1180                1185

Lys Asn Tyr Gly Gln Leu Asp Ile Phe Pro Ala Arg Asp Thr Tyr
        1190                1195                1200
```

-continued

```
His Pro Met Ser Glu Tyr Pro Thr Tyr His Thr His Gly Arg Tyr
    1205                1210                1215

Val Pro Pro Ser Ser Thr Asp Arg Ser Pro Tyr Glu Lys Val Ser
    1220                1225                1230

Ala Gly Asn Gly Gly Ser Ser Leu Ser Tyr Thr Asn Pro Ala Val
    1235                1240                1245

Ala Ala Thr Ser Ala Asn Leu
    1250                1255

<210> SEQ ID NO 13
<211> LENGTH: 5179
<212> TYPE: PRT
<213> ORGANISM: Homo sapiens
<220> FEATURE:
<223> OTHER INFORMATION: MUC2

<400> SEQUENCE: 13

Met Gly Leu Pro Leu Ala Arg Leu Ala Ala Val Cys Leu Ala Leu Ser
1               5                   10                  15

Leu Ala Gly Gly Ser Glu Leu Gln Thr Glu Gly Arg Thr Arg Tyr His
                20                  25                  30

Gly Arg Asn Val Cys Ser Thr Trp Gly Asn Phe His Tyr Lys Thr Phe
            35                  40                  45

Asp Gly Asp Val Phe Arg Phe Pro Gly Leu Cys Asp Tyr Asn Phe Ala
        50                  55                  60

Ser Asp Cys Arg Gly Ser Tyr Lys Glu Phe Ala Val His Leu Lys Arg
65                  70                  75                  80

Gly Pro Gly Gln Ala Glu Ala Pro Ala Gly Val Glu Ser Ile Leu Leu
                85                  90                  95

Thr Ile Lys Asp Asp Thr Ile Tyr Leu Thr Arg His Leu Ala Val Leu
            100                 105                 110

Asn Gly Ala Val Val Ser Thr Pro His Tyr Ser Pro Gly Leu Leu Ile
        115                 120                 125

Glu Lys Ser Asp Ala Tyr Thr Lys Val Tyr Ser Arg Ala Gly Leu Thr
    130                 135                 140

Leu Met Trp Asn Arg Glu Asp Ala Leu Met Leu Glu Leu Asp Thr Lys
145                 150                 155                 160

Phe Arg Asn His Thr Cys Gly Leu Cys Gly Asp Tyr Asn Gly Leu Gln
                165                 170                 175

Ser Tyr Ser Glu Phe Leu Ser Asp Gly Val Leu Phe Ser Pro Leu Glu
            180                 185                 190

Phe Gly Asn Met Gln Lys Ile Asn Gln Pro Asp Val Val Cys Glu Asp
        195                 200                 205

Pro Glu Glu Glu Val Ala Pro Ala Ser Cys Ser Glu His Arg Ala Glu
    210                 215                 220

Cys Glu Arg Leu Leu Thr Ala Glu Ala Phe Ala Asp Cys Gln Asp Leu
225                 230                 235                 240

Val Pro Leu Glu Pro Tyr Leu Arg Ala Cys Gln Gln Asp Arg Cys Arg
                245                 250                 255

Cys Pro Gly Gly Asp Thr Cys Val Cys Ser Thr Val Ala Glu Phe Ser
            260                 265                 270

Arg Gln Cys Ser His Ala Gly Gly Arg Pro Gly Asn Trp Arg Thr Ala
        275                 280                 285

Thr Leu Cys Pro Lys Thr Cys Pro Gly Asn Leu Val Tyr Leu Glu Ser
    290                 295                 300
```

-continued

```
Gly Ser Pro Cys Met Asp Thr Cys Ser His Leu Glu Val Ser Ser Leu
305                 310                 315                 320

Cys Glu Glu His Arg Met Asp Gly Cys Phe Cys Pro Glu Gly Thr Val
            325                 330                 335

Tyr Asp Asp Ile Gly Asp Ser Gly Cys Val Pro Val Ser Gln Cys His
                340                 345                 350

Cys Arg Leu His Gly His Leu Tyr Thr Pro Gly Gln Glu Ile Thr Asn
            355                 360                 365

Asp Cys Glu Gln Cys Val Cys Asn Ala Gly Arg Trp Val Cys Lys Asp
370                 375                 380

Leu Pro Cys Pro Gly Thr Cys Ala Leu Glu Gly Gly Ser His Ile Thr
385                 390                 395                 400

Thr Phe Asp Gly Lys Thr Tyr Thr Phe His Gly Asp Cys Tyr Tyr Val
                405                 410                 415

Leu Ala Lys Gly Asp His Asn Asp Ser Tyr Ala Leu Leu Gly Glu Leu
            420                 425                 430

Ala Pro Cys Gly Ser Thr Asp Lys Gln Thr Cys Leu Lys Thr Val Val
            435                 440                 445

Leu Leu Ala Asp Lys Lys Lys Asn Ala Val Val Phe Lys Ser Asp Gly
450                 455                 460

Ser Val Leu Leu Asn Gln Leu Gln Val Asn Leu Pro His Val Thr Ala
465                 470                 475                 480

Ser Phe Ser Val Phe Arg Pro Ser Ser Tyr His Ile Met Val Ser Met
            485                 490                 495

Ala Ile Gly Val Arg Leu Gln Val Gln Leu Ala Pro Val Met Gln Leu
            500                 505                 510

Phe Val Thr Leu Asp Gln Ala Ser Gln Gly Gln Val Gln Gly Leu Cys
            515                 520                 525

Gly Asn Phe Asn Gly Leu Glu Gly Asp Asp Phe Lys Thr Ala Ser Gly
            530                 535                 540

Leu Val Glu Ala Thr Gly Ala Gly Phe Ala Asn Thr Trp Lys Ala Gln
545                 550                 555                 560

Ser Thr Cys His Asp Lys Leu Asp Trp Leu Asp Asp Pro Cys Ser Leu
            565                 570                 575

Asn Ile Glu Ser Ala Asn Tyr Ala Glu His Trp Cys Ser Leu Leu Lys
            580                 585                 590

Lys Thr Glu Thr Pro Phe Gly Arg Cys His Ser Ala Val Asp Pro Ala
            595                 600                 605

Glu Tyr Tyr Lys Arg Cys Lys Tyr Asp Thr Cys Asn Cys Gln Asn Asn
            610                 615                 620

Glu Asp Cys Leu Cys Ala Ala Leu Ser Ser Tyr Ala Arg Ala Cys Thr
625                 630                 635                 640

Ala Lys Gly Val Met Leu Trp Gly Trp Arg Glu His Val Cys Asn Lys
            645                 650                 655

Asp Val Gly Ser Cys Pro Asn Ser Gln Val Phe Leu Tyr Asn Leu Thr
            660                 665                 670

Thr Cys Gln Gln Thr Cys Arg Ser Leu Ser Glu Ala Asp Ser His Cys
            675                 680                 685

Leu Glu Gly Phe Ala Pro Val Asp Gly Cys Gly Cys Pro Asp His Thr
            690                 695                 700

Phe Leu Asp Glu Lys Gly Arg Cys Val Pro Leu Ala Lys Cys Ser Cys
705                 710                 715                 720

Tyr His Arg Gly Leu Tyr Leu Glu Ala Gly Asp Val Val Val Arg Gln
```

-continued

```
            725                 730                 735
Glu Glu Arg Cys Val Cys Arg Asp Gly Arg Leu His Cys Arg Gln Ile
                740                 745                 750
Arg Leu Ile Gly Gln Ser Cys Thr Ala Pro Lys Ile His Met Asp Cys
                755                 760                 765
Ser Asn Leu Thr Ala Leu Ala Thr Ser Lys Pro Arg Ala Leu Ser Cys
                770                 775                 780
Gln Thr Leu Ala Ala Gly Tyr Tyr His Thr Glu Cys Val Ser Gly Cys
785                 790                 795                 800
Val Cys Pro Asp Gly Leu Met Asp Asp Gly Arg Gly Gly Cys Val Val
                805                 810                 815
Glu Lys Glu Cys Pro Cys Val His Asn Asn Asp Leu Tyr Ser Ser Gly
                820                 825                 830
Ala Lys Ile Lys Val Asp Cys Asn Thr Cys Thr Cys Lys Arg Gly Arg
                835                 840                 845
Trp Val Cys Thr Gln Ala Val Cys His Gly Thr Cys Ser Ile Tyr Gly
850                 855                 860
Ser Gly His Tyr Ile Thr Phe Asp Gly Lys Tyr Tyr Asp Phe Asp Gly
865                 870                 875                 880
His Cys Ser Tyr Val Ala Val Gln Asp Tyr Cys Gly Gln Asn Ser Ser
                885                 890                 895
Leu Gly Ser Phe Ser Ile Ile Thr Glu Asn Val Pro Cys Gly Thr Thr
                900                 905                 910
Gly Val Thr Cys Ser Lys Ala Ile Lys Ile Phe Met Gly Arg Thr Glu
                915                 920                 925
Leu Lys Leu Glu Asp Lys His Arg Val Val Ile Gln Arg Asp Glu Gly
                930                 935                 940
His His Val Ala Tyr Thr Thr Arg Glu Val Gly Gln Tyr Leu Val Val
945                 950                 955                 960
Glu Ser Ser Thr Gly Ile Ile Val Ile Trp Asp Lys Arg Thr Thr Val
                965                 970                 975
Phe Ile Lys Leu Ala Pro Ser Tyr Lys Gly Thr Val Cys Gly Leu Cys
                980                 985                 990
Gly Asn Phe Asp His Arg Ser Asn  Asn Asp Phe Thr Thr Arg Asp His
                995                1000                1005
Met Val  Val Ser Ser Glu Leu Asp Phe Gly Asn Ser  Trp Lys Glu
                1010                1015                1020
Ala Pro  Thr Cys Pro Asp Val  Ser Thr Asn Pro Glu  Pro Cys Ser
                1025                1030                1035
Leu Asn  Pro His Arg Arg Ser  Trp Ala Glu Lys Gln  Cys Ser Ile
                1040                1045                1050
Leu Lys  Ser Ser Val Phe Ser  Ile Cys His Ser Lys  Val Asp Pro
                1055                1060                1065
Lys Pro  Phe Tyr Glu Ala Cys  Val His Asp Ser Cys  Ser Cys Asp
                1070                1075                1080
Thr Gly  Gly Asp Cys Glu Cys  Phe Cys Ser Ala Val  Ala Ser Tyr
                1085                1090                1095
Ala Gln  Glu Cys Thr Lys Glu  Gly Ala Cys Val Phe  Trp Arg Thr
                1100                1105                1110
Pro Asp  Leu Cys Pro Ile Phe  Cys Asp Tyr Tyr Asn  Pro Pro His
                1115                1120                1125
Glu Cys  Glu Trp His Tyr Glu  Pro Cys Gly Asn Arg  Ser Phe Glu
                1130                1135                1140
```

```
Thr Cys Arg Thr Ile Asn Gly Ile His Ser Asn Ile Ser Val Ser
1145                1150                1155

Tyr Leu Glu Gly Cys Tyr Pro Arg Cys Pro Lys Asp Arg Pro Ile
1160                1165                1170

Tyr Glu Glu Asp Leu Lys Lys Cys Val Thr Ala Asp Lys Cys Gly
1175                1180                1185

Cys Tyr Val Glu Asp Thr His Tyr Pro Pro Gly Ala Ser Val Pro
1190                1195                1200

Thr Glu Glu Thr Cys Lys Ser Cys Val Cys Thr Asn Ser Ser Gln
1205                1210                1215

Val Val Cys Arg Pro Glu Glu Gly Lys Ile Leu Asn Gln Thr Gln
1220                1225                1230

Asp Gly Ala Phe Cys Tyr Trp Glu Ile Cys Gly Pro Asn Gly Thr
1235                1240                1245

Val Glu Lys His Phe Asn Ile Cys Ser Ile Thr Thr Arg Pro Ser
1250                1255                1260

Thr Leu Thr Thr Phe Thr Thr Ile Thr Leu Pro Thr Thr Pro Thr
1265                1270                1275

Ser Phe Thr Thr Thr Thr Thr Thr Thr Pro Thr Ser Ser Thr
1280                1285                1290

Val Leu Ser Thr Thr Pro Lys Leu Cys Cys Leu Trp Ser Asp Trp
1295                1300                1305

Ile Asn Glu Asp His Pro Ser Ser Gly Ser Asp Asp Gly Asp Arg
1310                1315                1320

Glu Pro Phe Asp Gly Val Cys Gly Ala Pro Glu Asp Ile Glu Cys
1325                1330                1335

Arg Ser Val Lys Asp Pro His Leu Ser Leu Glu Gln His Gly Gln
1340                1345                1350

Lys Val Gln Cys Asp Val Ser Val Gly Phe Ile Cys Lys Asn Glu
1355                1360                1365

Asp Gln Phe Gly Asn Gly Pro Phe Gly Leu Cys Tyr Asp Tyr Lys
1370                1375                1380

Ile Arg Val Asn Cys Cys Trp Pro Met Asp Lys Cys Ile Thr Thr
1385                1390                1395

Pro Ser Pro Pro Thr Thr Thr Pro Ser Pro Pro Thr Thr Thr
1400                1405                1410

Thr Thr Leu Pro Pro Thr Thr Pro Ser Pro Thr Thr Thr
1415                1420                1425

Thr Thr Thr Pro Pro Pro Thr Thr Pro Ser Pro Pro Ile Thr
1430                1435                1440

Thr Thr Thr Thr Pro Leu Pro Thr Thr Thr Pro Ser Pro Pro Ile
1445                1450                1455

Ser Thr Thr Thr Thr Pro Pro Thr Thr Thr Pro Ser Pro Pro
1460                1465                1470

Thr Thr Thr Pro Ser Pro Pro Thr Thr Thr Pro Ser Pro Pro Thr
1475                1480                1485

Thr Thr Thr Thr Thr Pro Pro Pro Thr Thr Thr Pro Ser Pro Pro
1490                1495                1500

Met Thr Thr Pro Ile Thr Pro Pro Ala Ser Thr Thr Thr Leu Pro
1505                1510                1515

Pro Thr Thr Thr Pro Ser Pro Pro Thr Thr Thr Thr Thr Pro
1520                1525                1530
```

-continued

Pro Pro Thr Thr Thr Pro Ser Pro Pro Thr Thr Thr Pro Ile Thr
1535                1540                1545

Pro Pro Thr Ser Thr Thr Thr Leu Pro Pro Thr Thr Thr Pro Ser
1550                1555                1560

Pro Pro Pro Thr Thr Thr Thr Pro Pro Pro Thr Thr Thr Pro
1565                1570                1575

Ser Pro Pro Thr Thr Thr Thr Pro Ser Pro Pro Thr Ile Thr Thr
1580                1585                1590

Thr Thr Pro Pro Pro Thr Thr Thr Pro Ser Pro Pro Thr Thr Thr
1595                1600                1605

Thr Thr Thr Pro Pro Pro Thr Thr Thr Pro Ser Pro Pro Thr Thr
1610                1615                1620

Thr Pro Ile Thr Pro Pro Thr Ser Thr Thr Thr Leu Pro Pro Thr
1625                1630                1635

Thr Thr Pro Ser Pro Pro Pro Thr Thr Thr Thr Thr Pro Pro Pro
1640                1645                1650

Thr Thr Thr Pro Ser Pro Pro Thr Thr Thr Thr Pro Ser Pro Pro
1655                1660                1665

Ile Thr Thr Thr Thr Thr Pro Pro Pro Thr Thr Thr Pro Ser Ser
1670                1675                1680

Pro Ile Thr Thr Thr Pro Ser Pro Pro Thr Thr Thr Met Thr Thr
1685                1690                1695

Pro Ser Pro Thr Thr Thr Thr Pro Ser Ser Pro Ile Thr Thr Thr Thr
1700                1705                1710

Thr Pro Ser Ser Thr Thr Thr Pro Ser Pro Pro Thr Thr Met
1715                1720                1725

Thr Thr Pro Ser Pro Thr Thr Thr Pro Ser Pro Pro Thr Thr Thr
1730                1735                1740

Met Thr Thr Leu Pro Pro Thr Thr Thr Ser Ser Pro Leu Thr Thr
1745                1750                1755

Thr Pro Leu Pro Pro Ser Ile Thr Pro Pro Thr Phe Ser Pro Phe
1760                1765                1770

Ser Thr Thr Thr Pro Thr Thr Pro Cys Val Pro Leu Cys Asn Trp
1775                1780                1785

Thr Gly Trp Leu Asp Ser Gly Lys Pro Asn Phe His Lys Pro Gly
1790                1795                1800

Gly Asp Thr Glu Leu Ile Gly Asp Val Cys Gly Pro Gly Trp Ala
1805                1810                1815

Ala Asn Ile Ser Cys Arg Ala Thr Met Tyr Pro Asp Val Pro Ile
1820                1825                1830

Gly Gln Leu Gly Gln Thr Val Val Cys Asp Val Ser Val Gly Leu
1835                1840                1845

Ile Cys Lys Asn Glu Asp Gln Lys Pro Gly Gly Val Ile Pro Met
1850                1855                1860

Ala Phe Cys Leu Asn Tyr Glu Ile Asn Val Gln Cys Cys Glu Cys
1865                1870                1875

Val Thr Gln Pro Thr Thr Met Thr Thr Thr Thr Glu Asn Pro
1880                1885                1890

Thr Pro Pro Thr Thr Thr Pro Ile Thr Thr Thr Thr Thr Val Thr
1895                1900                1905

Pro Thr Pro Thr Pro Thr Gly Thr Gln Thr Pro Thr Thr Thr Pro
1910                1915                1920

Ile Thr Thr Thr Thr Thr Val Thr Pro Thr Pro Thr Pro Thr Gly

-continued

```
              1925                1930                1935
Thr Gln Thr Pro Thr Thr Thr Pro Ile Thr Thr Thr Thr Val
        1940                1945                1950
Thr Pro Thr Pro Thr Pro Thr Gly Thr Gln Thr Pro Thr Thr Thr
        1955                1960                1965
Pro Ile Thr Thr Thr Thr Thr Val Thr Pro Thr Pro Thr Pro Thr
        1970                1975                1980
Gly Thr Gln Thr Pro Thr Thr Thr Pro Ile Thr Thr Thr Thr
        1985                1990                1995
Val Thr Pro Thr Pro Thr Pro Thr Gly Thr Gln Thr Pro Thr Thr
        2000                2005                2010
Thr Pro Ile Thr Thr Thr Thr Thr Val Thr Pro Thr Pro Thr Pro
        2015                2020                2025
Thr Gly Thr Gln Thr Pro Thr Thr Thr Pro Ile Thr Thr Thr Thr
        2030                2035                2040
Thr Val Thr Pro Thr Pro Thr Pro Thr Gly Thr Gln Thr Pro Thr
        2045                2050                2055
Thr Thr Pro Ile Thr Thr Thr Thr Thr Val Thr Pro Thr Pro Thr
        2060                2065                2070
Pro Thr Gly Thr Gln Thr Pro Thr Thr Thr Pro Ile Thr Thr Thr
        2075                2080                2085
Thr Thr Val Thr Pro Thr Pro Thr Pro Thr Gly Thr Gln Thr Pro
        2090                2095                2100
Thr Thr Thr Pro Ile Thr Thr Thr Thr Thr Val Thr Pro Thr Pro
        2105                2110                2115
Thr Pro Thr Gly Thr Gln Thr Pro Thr Thr Thr Pro Ile Thr Thr
        2120                2125                2130
Thr Thr Thr Val Thr Pro Thr Pro Thr Pro Thr Gly Thr Gln Thr
        2135                2140                2145
Pro Thr Thr Thr Pro Ile Thr Thr Thr Thr Thr Val Thr Pro Thr
        2150                2155                2160
Pro Thr Pro Thr Gly Thr Gln Thr Pro Thr Thr Thr Pro Ile Thr
        2165                2170                2175
Thr Thr Thr Val Thr Pro Thr Pro Thr Pro Thr Gly Thr Gln
        2180                2185                2190
Thr Pro Thr Thr Thr Pro Ile Thr Thr Thr Thr Thr Val Thr Pro
        2195                2200                2205
Thr Pro Thr Pro Thr Gly Thr Gln Thr Pro Thr Thr Thr Pro Ile
        2210                2215                2220
Thr Thr Thr Thr Val Thr Pro Thr Pro Thr Pro Thr Gly Thr
        2225                2230                2235
Gln Thr Pro Thr Thr Thr Pro Ile Thr Thr Thr Thr Thr Val Thr
        2240                2245                2250
Pro Thr Pro Thr Pro Thr Gly Thr Gln Thr Pro Thr Thr Thr Pro
        2255                2260                2265
Ile Thr Thr Thr Thr Thr Val Thr Pro Thr Pro Thr Pro Thr Gly
        2270                2275                2280
Thr Gln Thr Pro Thr Thr Thr Pro Ile Thr Thr Thr Thr Thr Val
        2285                2290                2295
Thr Pro Thr Pro Thr Pro Thr Gly Thr Gln Thr Pro Thr Thr Thr
        2300                2305                2310
Pro Ile Thr Thr Thr Thr Thr Val Thr Pro Thr Pro Thr Pro Thr
        2315                2320                2325
```

-continued

```
Gly Thr Gln Thr Pro Thr Thr Pro Ile Thr Thr Thr Thr Thr
    2330            2335            2340

Val Thr Pro Thr Pro Thr Pro Thr Gly Thr Gln Thr Pro Thr Thr
    2345            2350            2355

Thr Pro Ile Thr Thr Thr Thr Thr Val Thr Pro Thr Pro Thr Pro
    2360            2365            2370

Thr Gly Thr Gln Thr Pro Thr Thr Thr Pro Ile Thr Thr Thr Thr
    2375            2380            2385

Thr Val Thr Pro Thr Pro Thr Pro Thr Gly Thr Gln Thr Pro Thr
    2390            2395            2400

Thr Thr Pro Ile Thr Thr Thr Thr Thr Val Thr Pro Thr Pro Thr
    2405            2410            2415

Pro Thr Gly Thr Gln Thr Pro Thr Thr Thr Pro Ile Thr Thr Thr
    2420            2425            2430

Thr Thr Val Thr Pro Thr Pro Thr Pro Thr Gly Thr Gln Thr Pro
    2435            2440            2445

Thr Thr Thr Pro Ile Thr Thr Thr Thr Thr Val Thr Pro Thr Pro
    2450            2455            2460

Thr Pro Thr Gly Thr Gln Thr Pro Thr Thr Thr Pro Ile Thr Thr
    2465            2470            2475

Thr Thr Thr Val Thr Pro Thr Pro Thr Pro Thr Gly Thr Gln Thr
    2480            2485            2490

Pro Thr Thr Thr Pro Ile Thr Thr Thr Thr Thr Val Thr Pro Thr
    2495            2500            2505

Pro Thr Pro Thr Gly Thr Gln Thr Pro Thr Thr Thr Pro Ile Thr
    2510            2515            2520

Thr Thr Thr Thr Val Thr Pro Thr Pro Thr Pro Thr Gly Thr Gln
    2525            2530            2535

Thr Pro Thr Thr Thr Pro Ile Thr Thr Thr Thr Thr Val Thr Pro
    2540            2545            2550

Thr Pro Thr Pro Thr Gly Thr Gln Thr Pro Thr Thr Thr Pro Ile
    2555            2560            2565

Thr Thr Thr Thr Thr Val Thr Pro Thr Pro Thr Pro Thr Gly Thr
    2570            2575            2580

Gln Thr Pro Thr Thr Thr Pro Ile Thr Thr Thr Thr Thr Val Thr
    2585            2590            2595

Pro Thr Pro Thr Pro Thr Gly Thr Gln Thr Pro Thr Thr Thr Pro
    2600            2605            2610

Ile Thr Thr Thr Thr Thr Val Thr Pro Thr Pro Thr Pro Thr Gly
    2615            2620            2625

Thr Gln Thr Pro Thr Thr Thr Pro Ile Thr Thr Thr Thr Thr Val
    2630            2635            2640

Thr Pro Thr Pro Thr Pro Thr Gly Thr Gln Thr Pro Thr Thr Thr
    2645            2650            2655

Pro Ile Thr Thr Thr Thr Thr Val Thr Pro Thr Pro Thr Pro Thr
    2660            2665            2670

Gly Thr Gln Thr Pro Thr Thr Thr Pro Ile Thr Thr Thr Thr Thr
    2675            2680            2685

Val Thr Pro Thr Pro Thr Pro Thr Gly Thr Gln Thr Pro Thr Thr
    2690            2695            2700

Thr Pro Ile Thr Thr Thr Thr Thr Val Thr Pro Thr Pro Thr Pro
    2705            2710            2715
```

-continued

```
Thr Gly Thr Gln Thr Pro Thr Thr Pro Ile Thr Thr Thr
    2720            2725            2730

Thr Val Thr Pro Thr Pro Thr Pro Thr Gly Thr Gln Thr Pro Thr
    2735            2740            2745

Thr Thr Pro Ile Thr Thr Thr Thr Thr Val Thr Pro Thr Pro Thr
    2750            2755            2760

Pro Thr Gly Thr Gln Thr Pro Thr Thr Pro Ile Thr Thr Thr
    2765            2770            2775

Thr Thr Val Thr Pro Thr Pro Thr Pro Thr Gly Thr Gln Thr Pro
    2780            2785            2790

Thr Thr Thr Pro Ile Thr Thr Thr Thr Val Thr Pro Thr Pro
    2795            2800            2805

Thr Pro Thr Gly Thr Gln Thr Pro Thr Thr Thr Pro Ile Thr Thr
    2810            2815            2820

Thr Thr Thr Val Thr Pro Thr Pro Thr Pro Thr Gly Thr Gln Thr
    2825            2830            2835

Pro Thr Thr Thr Pro Ile Thr Thr Thr Thr Val Thr Pro Thr
    2840            2845            2850

Pro Thr Pro Thr Gly Thr Gln Thr Pro Thr Thr Thr Pro Ile Thr
    2855            2860            2865

Thr Thr Thr Val Thr Pro Thr Pro Thr Pro Thr Gly Thr Gln
    2870            2875            2880

Thr Pro Thr Thr Thr Pro Ile Thr Thr Thr Thr Val Thr Pro
    2885            2890            2895

Thr Pro Thr Pro Thr Gly Thr Gln Thr Pro Thr Thr Thr Pro Ile
    2900            2905            2910

Thr Thr Thr Thr Val Thr Pro Thr Pro Thr Pro Thr Gly Thr
    2915            2920            2925

Gln Thr Pro Thr Thr Thr Pro Ile Thr Thr Thr Thr Val Thr
    2930            2935            2940

Pro Thr Pro Thr Pro Thr Gly Thr Gln Thr Pro Thr Thr Thr Pro
    2945            2950            2955

Ile Thr Thr Thr Thr Val Thr Pro Thr Pro Thr Pro Thr Gly
    2960            2965            2970

Thr Gln Thr Pro Thr Thr Thr Pro Ile Thr Thr Thr Thr Val
    2975            2980            2985

Thr Pro Thr Pro Thr Pro Thr Gly Thr Gln Thr Pro Thr Thr Thr
    2990            2995            3000

Pro Ile Thr Thr Thr Thr Val Thr Pro Thr Pro Thr Pro Thr
    3005            3010            3015

Gly Thr Gln Thr Pro Thr Thr Thr Pro Ile Thr Thr Thr Thr
    3020            3025            3030

Val Thr Pro Thr Pro Thr Pro Thr Gly Thr Gln Thr Pro Thr Thr
    3035            3040            3045

Thr Pro Ile Thr Thr Thr Thr Val Thr Pro Thr Pro Thr Pro
    3050            3055            3060

Thr Gly Thr Gln Thr Pro Thr Thr Thr Pro Ile Thr Thr Thr
    3065            3070            3075

Thr Val Thr Pro Thr Pro Thr Pro Thr Gly Thr Gln Thr Pro Thr
    3080            3085            3090

Thr Thr Pro Ile Thr Thr Thr Thr Val Thr Pro Thr Pro Thr
    3095            3100            3105

Pro Thr Gly Thr Gln Thr Pro Thr Thr Thr Pro Ile Thr Thr Thr
```

-continued

```
            3110            3115            3120
Thr Thr Val Thr Pro Thr Pro Thr Pro Thr Gly Thr Gln Thr Pro
    3125            3130            3135
Thr Thr Thr Pro Ile Thr Thr Thr Thr Val Thr Pro Thr Pro
    3140            3145            3150
Thr Pro Thr Gly Thr Gln Thr Pro Thr Thr Thr Pro Ile Thr Thr
    3155            3160            3165
Thr Thr Thr Val Thr Pro Thr Pro Thr Pro Thr Gly Thr Gln Thr
    3170            3175            3180
Pro Thr Thr Thr Pro Ile Thr Thr Thr Thr Val Thr Pro Thr
    3185            3190            3195
Pro Thr Pro Thr Gly Thr Gln Thr Pro Thr Thr Thr Pro Ile Thr
    3200            3205            3210
Thr Thr Thr Val Thr Pro Thr Pro Thr Pro Thr Gly Thr Gln
    3215            3220            3225
Thr Pro Thr Thr Thr Pro Ile Thr Thr Thr Thr Val Thr Pro
    3230            3235            3240
Thr Pro Thr Pro Thr Gly Thr Gln Thr Pro Thr Thr Thr Pro Ile
    3245            3250            3255
Thr Thr Thr Thr Val Thr Pro Thr Pro Thr Pro Thr Gly Thr
    3260            3265            3270
Gln Thr Pro Thr Thr Thr Pro Ile Thr Thr Thr Thr Val Thr
    3275            3280            3285
Pro Thr Pro Thr Pro Thr Gly Thr Gln Thr Pro Thr Thr Thr Pro
    3290            3295            3300
Ile Thr Thr Thr Thr Val Thr Pro Thr Pro Thr Pro Thr Gly
    3305            3310            3315
Thr Gln Thr Pro Thr Thr Thr Pro Ile Thr Thr Thr Thr Val
    3320            3325            3330
Thr Pro Thr Pro Thr Pro Thr Gly Thr Gln Thr Pro Thr Thr Thr
    3335            3340            3345
Pro Ile Thr Thr Thr Thr Val Thr Pro Thr Pro Thr Pro Thr
    3350            3355            3360
Gly Thr Gln Thr Pro Thr Thr Thr Pro Ile Thr Thr Thr Thr
    3365            3370            3375
Val Thr Pro Thr Pro Thr Pro Thr Gly Thr Gln Thr Pro Thr Thr
    3380            3385            3390
Thr Pro Ile Thr Thr Thr Thr Val Thr Pro Thr Pro Thr Pro
    3395            3400            3405
Thr Gly Thr Gln Thr Pro Thr Thr Pro Ile Thr Thr Thr
    3410            3415            3420
Thr Val Thr Pro Thr Pro Thr Pro Thr Gly Thr Gln Thr Pro Thr
    3425            3430            3435
Thr Thr Pro Ile Thr Thr Thr Thr Val Thr Pro Thr Pro Thr
    3440            3445            3450
Pro Thr Gly Thr Gln Thr Pro Thr Thr Pro Ile Thr Thr Thr
    3455            3460            3465
Thr Thr Val Thr Pro Thr Pro Thr Pro Thr Gly Thr Gln Thr Pro
    3470            3475            3480
Thr Thr Thr Pro Ile Thr Thr Thr Thr Val Thr Pro Thr Pro
    3485            3490            3495
Thr Pro Thr Gly Thr Gln Thr Pro Thr Thr Thr Pro Ile Thr Thr
    3500            3505            3510
```

-continued

Thr Thr Thr Val Thr Pro Thr Pro Thr Gly Thr Gln Thr
    3515            3520            3525

Pro Thr Thr Thr Pro Ile Thr Thr Thr Thr Val Thr Pro Thr
    3530            3535            3540

Pro Thr Pro Thr Gly Thr Gln Thr Pro Thr Thr Thr Pro Ile Thr
    3545            3550            3555

Thr Thr Thr Thr Val Thr Pro Thr Pro Thr Pro Thr Gly Thr Gln
    3560            3565            3570

Thr Pro Thr Thr Thr Pro Ile Thr Thr Thr Thr Val Thr Pro
    3575            3580            3585

Thr Pro Thr Pro Thr Gly Thr Gln Thr Pro Thr Thr Thr Pro Ile
    3590            3595            3600

Thr Thr Thr Thr Thr Val Thr Pro Thr Pro Thr Pro Thr Gly Thr
    3605            3610            3615

Gln Thr Pro Thr Thr Thr Pro Ile Thr Thr Thr Thr Val Thr
    3620            3625            3630

Pro Thr Pro Thr Pro Thr Gly Thr Gln Thr Pro Thr Thr Thr Pro
    3635            3640            3645

Ile Thr Thr Thr Thr Thr Val Thr Pro Thr Pro Thr Pro Thr Gly
    3650            3655            3660

Thr Gln Thr Pro Thr Thr Thr Pro Ile Thr Thr Thr Thr Val
    3665            3670            3675

Thr Pro Thr Pro Thr Pro Thr Gly Thr Gln Thr Pro Thr Thr Thr
    3680            3685            3690

Pro Ile Thr Thr Thr Thr Thr Val Thr Pro Thr Pro Thr Pro Thr
    3695            3700            3705

Gly Thr Gln Thr Pro Thr Thr Thr Pro Ile Thr Thr Thr Thr
    3710            3715            3720

Val Thr Pro Thr Pro Thr Pro Thr Gly Thr Gln Thr Pro Thr Thr
    3725            3730            3735

Thr Pro Ile Thr Thr Thr Thr Thr Val Thr Pro Thr Pro Thr Pro
    3740            3745            3750

Thr Gly Thr Gln Thr Pro Thr Thr Thr Pro Ile Thr Thr Thr Thr
    3755            3760            3765

Thr Val Thr Pro Thr Pro Thr Pro Thr Gly Thr Gln Thr Pro Thr
    3770            3775            3780

Thr Thr Pro Ile Thr Thr Thr Thr Thr Val Thr Pro Thr Pro Thr
    3785            3790            3795

Pro Thr Gly Thr Gln Thr Pro Thr Thr Thr Pro Ile Thr Thr Thr
    3800            3805            3810

Thr Thr Val Thr Pro Thr Pro Thr Pro Thr Gly Thr Gln Thr Pro
    3815            3820            3825

Thr Thr Thr Pro Ile Thr Thr Thr Thr Thr Val Thr Pro Thr Pro
    3830            3835            3840

Thr Pro Thr Gly Thr Gln Thr Pro Thr Thr Thr Pro Ile Thr Thr
    3845            3850            3855

Thr Thr Thr Val Thr Pro Thr Pro Thr Pro Thr Gly Thr Gln Thr
    3860            3865            3870

Pro Thr Thr Thr Pro Ile Thr Thr Thr Thr Val Thr Pro Thr
    3875            3880            3885

Pro Thr Pro Thr Gly Thr Gln Thr Pro Thr Thr Thr Pro Ile Thr
    3890            3895            3900

-continued

Thr Thr Thr Thr Val Thr Pro Thr Pro Thr Pro Thr Gly Thr Gln
3905              3910              3915

Thr Pro Thr Thr Thr Pro Ile Thr Thr Thr Thr Val Thr Pro
3920              3925              3930

Thr Pro Thr Pro Thr Gly Thr Gln Thr Pro Thr Thr Pro Ile
3935              3940              3945

Thr Thr Thr Thr Thr Val Thr Pro Thr Pro Thr Pro Thr Gly Thr
3950              3955              3960

Gln Thr Pro Thr Thr Thr Pro Ile Thr Thr Thr Thr Val Thr
3965              3970              3975

Pro Thr Pro Thr Pro Thr Gly Thr Gln Thr Pro Thr Thr Thr Pro
3980              3985              3990

Ile Thr Thr Thr Thr Val Thr Pro Thr Pro Thr Pro Thr Gly
3995              4000              4005

Thr Gln Thr Pro Thr Thr Thr Pro Ile Thr Thr Thr Thr Val
4010              4015              4020

Thr Pro Thr Pro Thr Pro Thr Gly Thr Gln Thr Pro Thr Thr Thr
4025              4030              4035

Pro Ile Thr Thr Thr Thr Thr Val Thr Pro Thr Pro Thr Pro Thr
4040              4045              4050

Gly Thr Gln Thr Pro Thr Thr Thr Pro Ile Thr Thr Thr Thr
4055              4060              4065

Val Thr Pro Thr Pro Thr Pro Thr Gly Thr Gln Thr Pro Thr Thr
4070              4075              4080

Thr Pro Ile Thr Thr Thr Thr Thr Val Thr Pro Thr Pro Thr Pro
4085              4090              4095

Thr Gly Thr Gln Thr Pro Thr Thr Thr Pro Ile Thr Thr Thr
4100              4105              4110

Thr Val Thr Pro Thr Pro Thr Pro Thr Gly Thr Gln Thr Pro Thr
4115              4120              4125

Thr Thr Pro Ile Thr Thr Thr Thr Thr Val Thr Pro Thr Pro Thr
4130              4135              4140

Pro Thr Gly Thr Gln Thr Pro Thr Thr Thr Pro Ile Thr Thr Thr
4145              4150              4155

Thr Thr Val Thr Pro Thr Pro Thr Pro Thr Gly Thr Gln Thr Pro
4160              4165              4170

Thr Thr Thr Pro Ile Thr Thr Thr Thr Thr Val Thr Pro Thr Pro
4175              4180              4185

Thr Pro Thr Gly Thr Gln Thr Gly Pro Pro Thr His Thr Ser Thr
4190              4195              4200

Ala Pro Ile Ala Glu Leu Thr Thr Ser Asn Pro Pro Glu Ser
4205              4210              4215

Ser Thr Pro Gln Thr Ser Arg Ser Thr Ser Ser Pro Leu Thr Glu
4220              4225              4230

Ser Thr Thr Leu Leu Ser Thr Leu Pro Pro Ala Ile Glu Met Thr
4235              4240              4245

Ser Thr Ala Pro Pro Ser Thr Pro Thr Ala Pro Thr Thr Thr Ser
4250              4255              4260

Gly Gly His Thr Leu Ser Pro Pro Pro Ser Thr Thr Thr Ser Pro
4265              4270              4275

Pro Gly Thr Pro Thr Arg Gly Thr Thr Thr Gly Ser Ser Ser Ala
4280              4285              4290

Pro Thr Pro Ser Thr Val Gln Thr Thr Thr Thr Ser Ala Trp Thr

-continued

```
              4295                4300                4305
Pro Thr Pro Thr Pro Leu Ser Thr Pro Ser Ile Ile Arg Thr Thr
        4310                4315                4320
Gly Leu Arg Pro Tyr Pro Ser Ser Val Leu Ile Cys Cys Val Leu
        4325                4330                4335
Asn Asp Thr Tyr Tyr Ala Pro Gly Glu Glu Val Tyr Asn Gly Thr
        4340                4345                4350
Tyr Gly Asp Thr Cys Tyr Phe Val Asn Cys Ser Leu Ser Cys Thr
        4355                4360                4365
Leu Glu Phe Tyr Asn Trp Ser Cys Pro Ser Thr Pro Ser Pro Thr
        4370                4375                4380
Pro Thr Pro Ser Lys Ser Thr Pro Thr Pro Ser Lys Pro Ser Ser
        4385                4390                4395
Thr Pro Ser Lys Pro Thr Pro Gly Thr Lys Pro Pro Glu Cys Pro
        4400                4405                4410
Asp Phe Asp Pro Pro Arg Gln Glu Asn Glu Thr Trp Trp Leu Cys
        4415                4420                4425
Asp Cys Phe Met Ala Thr Cys Lys Tyr Asn Asn Thr Val Glu Ile
        4430                4435                4440
Val Lys Val Glu Cys Glu Pro Pro Met Pro Thr Cys Ser Asn
        4445                4450                4455
Gly Leu Gln Pro Val Arg Val Glu Asp Pro Asp Gly Cys Cys Trp
        4460                4465                4470
His Trp Glu Cys Asp Cys Tyr Cys Thr Gly Trp Gly Asp Pro His
        4475                4480                4485
Tyr Val Thr Phe Asp Gly Leu Tyr Tyr Ser Tyr Gln Gly Asn Cys
        4490                4495                4500
Thr Tyr Val Leu Val Glu Glu Ile Ser Pro Ser Val Asp Asn Phe
        4505                4510                4515
Gly Val Tyr Ile Asp Asn Tyr His Cys Asp Pro Asn Asp Lys Val
        4520                4525                4530
Ser Cys Pro Arg Thr Leu Ile Val Arg His Glu Thr Gln Glu Val
        4535                4540                4545
Leu Ile Lys Thr Val His Met Met Pro Met Gln Val Gln Val Gln
        4550                4555                4560
Val Asn Arg Gln Ala Val Ala Leu Pro Tyr Lys Lys Tyr Gly Leu
        4565                4570                4575
Glu Val Tyr Gln Ser Gly Ile Asn Tyr Val Val Asp Ile Pro Glu
        4580                4585                4590
Leu Gly Val Leu Val Ser Tyr Asn Gly Leu Ser Phe Ser Val Arg
        4595                4600                4605
Leu Pro Tyr His Arg Phe Gly Asn Asn Thr Lys Gly Gln Cys Gly
        4610                4615                4620
Thr Cys Thr Asn Thr Thr Ser Asp Asp Cys Ile Leu Pro Ser Gly
        4625                4630                4635
Glu Ile Val Ser Asn Cys Glu Ala Ala Ala Asp Gln Trp Leu Val
        4640                4645                4650
Asn Asp Pro Ser Lys Pro His Cys Pro His Ser Ser Thr Thr
        4655                4660                4665
Lys Arg Pro Ala Val Thr Val Pro Gly Gly Gly Lys Thr Thr Pro
        4670                4675                4680
His Lys Asp Cys Thr Pro Ser Pro Leu Cys Gln Leu Ile Lys Asp
        4685                4690                4695
```

```
Ser Leu Phe Ala Gln Cys His Ala Leu Val Pro Pro Gln His Tyr
    4700            4705            4710

Tyr Asp Ala Cys Val Phe Asp Ser Cys Phe Met Pro Gly Ser Ser
    4715            4720            4725

Leu Glu Cys Ala Ser Leu Gln Ala Tyr Ala Ala Leu Cys Ala Gln
    4730            4735            4740

Gln Asn Ile Cys Leu Asp Trp Arg Asn His Thr His Gly Ala Cys
    4745            4750            4755

Leu Val Glu Cys Pro Ser His Arg Glu Tyr Gln Ala Cys Gly Pro
    4760            4765            4770

Ala Glu Glu Pro Thr Cys Lys Ser Ser Ser Gln Gln Asn Asn
    4775            4780            4785

Thr Val Leu Val Glu Gly Cys Phe Cys Pro Glu Gly Thr Met Asn
    4790            4795            4800

Tyr Ala Pro Gly Phe Asp Val Cys Val Lys Thr Cys Gly Cys Val
    4805            4810            4815

Gly Pro Asp Asn Val Pro Arg Glu Phe Gly Glu His Phe Glu Phe
    4820            4825            4830

Asp Cys Lys Asn Cys Val Cys Leu Glu Gly Gly Ser Gly Ile Ile
    4835            4840            4845

Cys Gln Pro Lys Arg Cys Ser Gln Lys Pro Val Thr His Cys Val
    4850            4855            4860

Glu Asp Gly Thr Tyr Leu Ala Thr Glu Val Asn Pro Ala Asp Thr
    4865            4870            4875

Cys Cys Asn Ile Thr Val Cys Lys Cys Asn Thr Ser Leu Cys Lys
    4880            4885            4890

Glu Lys Pro Ser Val Cys Pro Leu Gly Phe Glu Val Lys Ser Lys
    4895            4900            4905

Met Val Pro Gly Arg Cys Cys Pro Phe Tyr Trp Cys Glu Ser Lys
    4910            4915            4920

Gly Val Cys Val His Gly Asn Ala Glu Tyr Gln Pro Gly Ser Pro
    4925            4930            4935

Val Tyr Ser Ser Lys Cys Gln Asp Cys Val Cys Thr Asp Lys Val
    4940            4945            4950

Asp Asn Asn Thr Leu Leu Asn Val Ile Ala Cys Thr His Val Pro
    4955            4960            4965

Cys Asn Thr Ser Cys Ser Pro Gly Phe Glu Leu Met Glu Ala Pro
    4970            4975            4980

Gly Glu Cys Cys Lys Lys Cys Glu Gln Thr His Cys Ile Ile Lys
    4985            4990            4995

Arg Pro Asp Asn Gln His Val Ile Leu Lys Pro Gly Asp Phe Lys
    5000            5005            5010

Ser Asp Pro Lys Asn Asn Cys Thr Phe Phe Ser Cys Val Lys Ile
    5015            5020            5025

His Asn Gln Leu Ile Ser Ser Val Ser Asn Ile Thr Cys Pro Asn
    5030            5035            5040

Phe Asp Ala Ser Ile Cys Ile Pro Gly Ser Ile Thr Phe Met Pro
    5045            5050            5055

Asn Gly Cys Cys Lys Thr Cys Thr Pro Arg Asn Glu Thr Arg Val
    5060            5065            5070

Pro Cys Ser Thr Val Pro Val Thr Thr Glu Val Ser Tyr Ala Gly
    5075            5080            5085
```

```
Cys Thr Lys Thr Val Leu Met Asn His Cys Ser Gly Ser Cys Gly
    5090                5095                5100

Thr Phe Val Met Tyr Ser Ala Lys Ala Gln Ala Leu Asp His Ser
    5105                5110                5115

Cys Ser Cys Cys Lys Glu Glu Lys Thr Ser Gln Arg Glu Val Val
    5120                5125                5130

Leu Ser Cys Pro Asn Gly Gly Ser Leu Thr His Thr Tyr Thr His
    5135                5140                5145

Ile Glu Ser Cys Gln Cys Gln Asp Thr Val Cys Gly Leu Pro Thr
    5150                5155                5160

Gly Thr Ser Arg Arg Ala Arg Arg Ser Pro Arg His Leu Gly Ser
    5165                5170                5175

Gly
```

<210> SEQ ID NO 14
<211> LENGTH: 2169
<212> TYPE: PRT
<213> ORGANISM: Homo sapiens
<220> FEATURE:
<223> OTHER INFORMATION: MUC4

<400> SEQUENCE: 14

```
Met Lys Gly Ala Arg Trp Arg Arg Val Pro Trp Val Ser Leu Ser Cys
1               5                   10                  15

Leu Cys Leu Cys Leu Leu Pro His Val Val Pro Gly Thr Thr Glu Asp
            20                  25                  30

Thr Leu Ile Thr Gly Ser Lys Thr Ala Ala Pro Val Thr Ser Thr Gly
        35                  40                  45

Ser Thr Thr Ala Thr Leu Glu Gly Gln Ser Thr Ala Ala Ser Ser Arg
    50                  55                  60

Thr Ser Asn Gln Asp Ile Ser Ala Ser Ser Gln Asn His Gln Thr Lys
65                  70                  75                  80

Ser Thr Glu Thr Thr Ser Lys Ala Gln Thr Asp Thr Leu Thr Gln Met
                85                  90                  95

Met Thr Ser Thr Leu Phe Ser Ser Pro Ser Val His Asn Val Met Glu
            100                 105                 110

Thr Val Thr Gln Glu Thr Ala Pro Pro Asp Glu Met Thr Thr Ser Phe
        115                 120                 125

Pro Ser Ser Val Thr Asn Thr Leu Met Met Thr Ser Lys Thr Ile Thr
    130                 135                 140

Met Thr Thr Ser Thr Asp Ser Thr Leu Gly Asn Thr Glu Glu Thr Ser
145                 150                 155                 160

Thr Ala Gly Thr Glu Ser Ser Thr Pro Val Thr Ser Ala Val Ser Ile
                165                 170                 175

Thr Ala Gly Gln Glu Gly Gln Ser Arg Thr Thr Ser Trp Arg Thr Ser
            180                 185                 190

Ile Gln Asp Thr Ser Ala Ser Ser Gln Asn His Trp Thr Arg Ser Thr
        195                 200                 205

Gln Thr Thr Arg Glu Ser Gln Thr Ser Thr Leu Thr His Arg Thr Thr
    210                 215                 220

Ser Thr Pro Ser Phe Ser Pro Ser Val His Asn Val Thr Gly Thr Val
225                 230                 235                 240

Ser Gln Lys Thr Ser Pro Ser Gly Glu Thr Ala Thr Ser Ser Leu Cys
                245                 250                 255

Ser Val Thr Asn Thr Ser Met Met Thr Ser Glu Lys Ile Thr Val Thr
```

-continued

```
                260                 265                 270
Thr Ser Thr Gly Ser Thr Leu Gly Asn Pro Gly Glu Thr Ser Ser Val
            275                 280                 285

Pro Val Thr Gly Ser Leu Met Pro Val Thr Ser Ala Ala Leu Val Thr
            290                 295                 300

Val Asp Pro Glu Gly Gln Ser Pro Ala Thr Phe Ser Arg Thr Ser Thr
305                 310                 315                 320

Gln Asp Thr Thr Ala Phe Ser Lys Asn His Gln Thr Gln Ser Val Glu
            325                 330                 335

Thr Thr Arg Val Ser Gln Ile Asn Thr Leu Asn Thr Leu Thr Pro Val
            340                 345                 350

Thr Thr Ser Thr Val Leu Ser Ser Pro Ser Gly Phe Asn Pro Ser Gly
            355                 360                 365

Thr Val Ser Gln Glu Thr Phe Pro Ser Gly Thr Thr Ile Ser Ser
            370                 375                 380

Pro Ser Ser Val Ser Asn Thr Phe Leu Val Thr Ser Lys Val Phe Arg
385                 390                 395                 400

Met Pro Ile Ser Arg Asp Ser Thr Leu Gly Asn Thr Glu Glu Thr Ser
                405                 410                 415

Leu Ser Val Ser Gly Thr Ile Ser Ala Ile Thr Ser Lys Val Ser Thr
            420                 425                 430

Ile Trp Trp Ser Asp Thr Leu Ser Thr Ala Leu Ser Pro Ser Ser Leu
            435                 440                 445

Pro Pro Lys Ile Ser Thr Ala Phe His Thr Gln Gln Ser Glu Gly Ala
            450                 455                 460

Glu Thr Thr Gly Arg Pro His Glu Arg Ser Ser Phe Ser Pro Gly Val
465                 470                 475                 480

Ser Gln Glu Ile Phe Thr Leu His Glu Thr Thr Thr Trp Pro Ser Ser
                485                 490                 495

Phe Ser Ser Lys Gly His Thr Thr Trp Ser Gln Thr Glu Leu Pro Ser
            500                 505                 510

Thr Ser Thr Gly Ala Ala Thr Arg Leu Val Thr Gly Asn Pro Ser Thr
            515                 520                 525

Arg Ala Ala Gly Thr Ile Pro Arg Val Pro Ser Lys Val Ser Ala Ile
530                 535                 540

Gly Glu Pro Gly Glu Pro Thr Thr Tyr Ser Ser His Ser Thr Thr Leu
545                 550                 555                 560

Pro Lys Thr Thr Gly Ala Gly Ala Gln Thr Gln Trp Thr Gln Glu Thr
                565                 570                 575

Gly Thr Thr Gly Glu Ala Leu Leu Ser Ser Pro Ser Tyr Ser Val Ile
            580                 585                 590

Gln Met Ile Lys Thr Ala Thr Ser Pro Ser Ser Pro Met Leu Asp
            595                 600                 605

Arg His Thr Ser Gln Gln Ile Thr Thr Ala Pro Ser Thr Asn His Ser
            610                 615                 620

Thr Ile His Ser Thr Ser Thr Ser Pro Gln Glu Ser Pro Ala Val Ser
625                 630                 635                 640

Gln Arg Gly His Thr Arg Ala Pro Gln Thr Thr Gln Glu Ser Gln Thr
                645                 650                 655

Thr Arg Ser Val Ser Pro Met Thr Asp Thr Lys Thr Val Thr Thr Pro
            660                 665                 670

Gly Ser Ser Phe Thr Ala Ser Gly His Ser Pro Ser Glu Ile Val Pro
            675                 680                 685
```

Gln Asp Ala Pro Thr Ile Ser Ala Ala Thr Thr Phe Ala Pro Ala Pro
690                 695                 700

Thr Gly Asn Gly His Thr Thr Gln Ala Pro Thr Ala Leu Gln Ala
705                 710                 715                 720

Ala Pro Ser Ser His Asp Ala Thr Leu Gly Pro Ser Gly Gly Thr Ser
            725                 730                 735

Leu Ser Lys Thr Gly Ala Leu Thr Leu Ala Asn Ser Val Val Ser Thr
        740                 745                 750

Pro Gly Gly Pro Glu Gly Gln Trp Thr Ser Ala Ser Ala Ser Thr Ser
    755                 760                 765

Pro Asp Thr Ala Ala Ala Met Thr His Thr His Gln Ala Glu Ser Thr
770                 775                 780

Glu Ala Ser Gly Gln Thr Gln Thr Ser Glu Pro Ala Ser Ser Gly Ser
785                 790                 795                 800

Arg Thr Thr Ser Ala Gly Thr Ala Thr Pro Ser Ser Ser Gly Ala Ser
                805                 810                 815

Gly Thr Thr Pro Ser Gly Ser Glu Gly Ile Ser Thr Ser Gly Glu Thr
            820                 825                 830

Thr Arg Phe Ser Ser Asn Pro Ser Arg Asp Ser His Thr Thr Gln Ser
        835                 840                 845

Thr Thr Glu Leu Leu Ser Ala Ser Ala Ser His Gly Ala Ile Pro Val
850                 855                 860

Ser Thr Gly Met Ala Ser Ser Ile Val Pro Gly Thr Phe His Pro Thr
865                 870                 875                 880

Leu Ser Glu Ala Ser Thr Ala Gly Arg Pro Thr Gly Gln Ser Ser Pro
                885                 890                 895

Thr Ser Pro Ser Ala Ser Pro Gln Glu Thr Ala Ala Ile Ser Arg Met
            900                 905                 910

Ala Gln Thr Gln Arg Thr Gly Thr Ser Arg Gly Ser Asp Thr Ile Ser
        915                 920                 925

Leu Ala Ser Gln Ala Thr Asp Thr Phe Ser Thr Val Pro Pro Thr Pro
930                 935                 940

Pro Ser Ile Thr Ser Ser Gly Leu Thr Ser Pro Gln Thr Gln Thr His
945                 950                 955                 960

Thr Leu Ser Pro Ser Gly Ser Gly Lys Thr Phe Thr Thr Ala Leu Ile
                965                 970                 975

Ser Asn Ala Thr Pro Leu Pro Val Thr Ser Thr Ser Ser Ala Ser Thr
            980                 985                 990

Gly His Ala Thr Pro Leu Ala Val Ser Ser Ala Thr Ser Ala Ser Thr
        995                 1000                1005

Val Ser Ser Asp Ser Pro Leu Lys Met Glu Thr Ser Gly Met Thr
    1010                1015                1020

Thr Pro Ser Leu Lys Thr Asp Gly Gly Arg Arg Thr Ala Thr Ser
    1025                1030                1035

Pro Pro Pro Thr Thr Ser Gln Thr Ile Ile Ser Thr Ile Pro Ser
    1040                1045                1050

Thr Ala Met His Thr Arg Ser Thr Ala Ala Pro Ile Pro Ile Leu
    1055                1060                1065

Pro Glu Arg Gly Val Ser Leu Phe Pro Tyr Gly Ala Gly Ala Gly
    1070                1075                1080

Asp Leu Glu Phe Val Arg Arg Thr Val Asp Phe Thr Ser Pro Leu
    1085                1090                1095

-continued

```
Phe Lys Pro Ala Thr Gly Phe Pro Leu Gly Ser Ser Leu Arg Asp
    1100                1105                1110
Ser Leu Tyr Phe Thr Asp Asn Gly Gln Ile Ile Phe Pro Glu Ser
    1115                1120                1125
Asp Tyr Gln Ile Phe Ser Tyr Pro Asn Pro Leu Pro Thr Gly Phe
    1130                1135                1140
Thr Gly Arg Asp Pro Val Ala Leu Val Ala Pro Phe Trp Asp Asp
    1145                1150                1155
Ala Asp Phe Ser Thr Gly Arg Gly Thr Thr Phe Tyr Gln Glu Tyr
    1160                1165                1170
Glu Thr Phe Tyr Gly Glu His Ser Leu Leu Val Gln Gln Ala Glu
    1175                1180                1185
Ser Trp Ile Arg Lys Met Thr Asn Asn Gly Gly Tyr Lys Ala Arg
    1190                1195                1200
Trp Ala Leu Lys Val Thr Trp Val Asn Ala His Ala Tyr Pro Ala
    1205                1210                1215
Gln Trp Thr Leu Gly Ser Asn Thr Tyr Gln Ala Ile Leu Ser Thr
    1220                1225                1230
Asp Gly Ser Arg Ser Tyr Ala Leu Phe Leu Tyr Gln Ser Gly Gly
    1235                1240                1245
Met Gln Trp Asp Val Ala Gln Arg Ser Gly Asn Pro Val Leu Met
    1250                1255                1260
Gly Phe Ser Ser Gly Asp Gly Tyr Phe Glu Asn Ser Pro Leu Met
    1265                1270                1275
Ser Gln Pro Val Trp Glu Arg Tyr Arg Pro Asp Arg Phe Leu Asn
    1280                1285                1290
Ser Asn Ser Gly Leu Gln Gly Leu Gln Phe Tyr Arg Leu His Arg
    1295                1300                1305
Glu Glu Arg Pro Asn Tyr Arg Leu Glu Cys Leu Gln Trp Leu Lys
    1310                1315                1320
Ser Gln Pro Arg Trp Pro Ser Trp Gly Trp Asn Gln Val Ser Cys
    1325                1330                1335
Pro Cys Ser Trp Gln Gln Gly Arg Arg Asp Leu Arg Phe Gln Pro
    1340                1345                1350
Val Ser Ile Gly Arg Trp Gly Leu Gly Ser Arg Gln Leu Cys Ser
    1355                1360                1365
Phe Thr Ser Trp Arg Gly Gly Val Cys Cys Ser Tyr Gly Pro Trp
    1370                1375                1380
Gly Glu Phe Arg Glu Gly Trp His Val Gln Arg Pro Trp Gln Leu
    1385                1390                1395
Ala Gln Glu Leu Glu Pro Gln Ser Trp Cys Cys Arg Trp Asn Asp
    1400                1405                1410
Lys Pro Tyr Leu Cys Ala Leu Tyr Gln Gln Arg Arg Pro His Val
    1415                1420                1425
Gly Cys Ala Thr Tyr Arg Pro Pro Gln Pro Ala Trp Met Phe Gly
    1430                1435                1440
Asp Pro His Ile Thr Thr Leu Asp Gly Val Ser Tyr Thr Phe Asn
    1445                1450                1455
Gly Leu Gly Asp Phe Leu Leu Val Gly Ala Gln Asp Gly Asn Ser
    1460                1465                1470
Ser Phe Leu Leu Gln Gly Arg Thr Ala Gln Thr Gly Ser Ala Gln
    1475                1480                1485
Ala Thr Asn Phe Ile Ala Phe Ala Ala Gln Tyr Arg Ser Ser Ser
```

-continued

```
            1490                1495                1500

Leu Gly Pro Val Thr Val Gln Trp Leu Glu Pro His Asp Ala
    1505                1510                1515

Ile Arg Val Leu Leu Asp Asn Gln Thr Val Thr Phe Gln Pro Asp
    1520                1525                1530

His Glu Asp Gly Gly Gln Glu Thr Phe Asn Ala Thr Gly Val
    1535                1540                1545

Leu Leu Ser Arg Asn Gly Ser Glu Val Ser Ala Ser Phe Asp Gly
    1550                1555                1560

Trp Ala Thr Val Ser Val Ile Ala Leu Ser Asn Ile Leu His Ala
    1565                1570                1575

Ser Ala Ser Leu Pro Pro Glu Tyr Gln Asn Arg Thr Glu Gly Leu
    1580                1585                1590

Leu Gly Val Trp Asn Asn Pro Glu Asp Asp Phe Arg Met Pro
    1595                1600                1605

Asn Gly Ser Thr Ile Pro Pro Gly Ser Pro Glu Glu Met Leu Phe
    1610                1615                1620

His Phe Gly Met Thr Trp Gln Ile Asn Gly Thr Gly Leu Leu Gly
    1625                1630                1635

Lys Arg Asn Asp Gln Leu Pro Ser Asn Phe Thr Pro Val Phe Tyr
    1640                1645                1650

Ser Gln Leu Gln Lys Asn Ser Ser Trp Ala Glu His Leu Ile Ser
    1655                1660                1665

Asn Cys Asp Gly Asp Ser Ser Cys Ile Tyr Asp Thr Leu Ala Leu
    1670                1675                1680

Arg Asn Ala Ser Ile Gly Leu His Thr Arg Glu Val Ser Lys Asn
    1685                1690                1695

Tyr Glu Gln Ala Asn Ala Thr Leu Asn Gln Tyr Pro Pro Ser Ile
    1700                1705                1710

Asn Gly Gly Arg Val Ile Glu Ala Tyr Lys Gly Gln Thr Thr Leu
    1715                1720                1725

Ile Gln Tyr Thr Ser Asn Ala Glu Asp Ala Asn Phe Thr Leu Arg
    1730                1735                1740

Asp Ser Cys Thr Asp Leu Glu Leu Phe Glu Asn Gly Thr Leu Leu
    1745                1750                1755

Trp Thr Pro Lys Ser Leu Glu Pro Phe Thr Leu Glu Ile Leu Ala
    1760                1765                1770

Arg Ser Ala Lys Ile Gly Leu Ala Ser Ala Leu Gln Pro Arg Thr
    1775                1780                1785

Val Val Cys His Cys Asn Ala Glu Ser Gln Cys Leu Tyr Asn Gln
    1790                1795                1800

Thr Ser Arg Val Gly Asn Ser Ser Leu Glu Val Ala Gly Cys Lys
    1805                1810                1815

Cys Asp Gly Gly Thr Phe Gly Arg Tyr Cys Glu Gly Ser Glu Asp
    1820                1825                1830

Ala Cys Glu Glu Pro Cys Phe Pro Ser Val His Cys Val Pro Gly
    1835                1840                1845

Lys Gly Cys Glu Ala Cys Pro Pro Asn Leu Thr Gly Asp Gly Arg
    1850                1855                1860

His Cys Ala Ala Leu Gly Ser Ser Phe Leu Cys Gln Asn Gln Ser
    1865                1870                1875

Cys Pro Val Asn Tyr Cys Tyr Asn Gln Gly His Cys Tyr Ile Ser
    1880                1885                1890
```

```
Gln Thr Leu Gly Cys Gln Pro Met Cys Thr Cys Pro Pro Ala Phe
    1895                1900                1905

Thr Asp Ser Arg Cys Phe Leu Ala Gly Asn Asn Phe Ser Pro Thr
    1910                1915                1920

Val Asn Leu Glu Leu Pro Leu Arg Val Ile Gln Leu Leu Leu Ser
    1925                1930                1935

Glu Glu Glu Asn Ala Ser Met Ala Glu Val Asn Ala Ser Val Ala
    1940                1945                1950

Tyr Arg Leu Gly Thr Leu Asp Met Arg Ala Phe Leu Arg Asn Ser
    1955                1960                1965

Gln Val Glu Arg Ile Asp Ser Ala Ala Pro Ala Ser Gly Ser Pro
    1970                1975                1980

Ile Gln His Trp Met Val Ile Ser Glu Phe Gln Tyr Arg Pro Arg
    1985                1990                1995

Gly Pro Val Ile Asp Phe Leu Asn Asn Gln Leu Leu Ala Ala Val
    2000                2005                2010

Val Glu Ala Phe Leu Tyr His Val Pro Arg Arg Ser Glu Glu Pro
    2015                2020                2025

Arg Asn Asp Val Val Phe Gln Pro Ile Ser Gly Glu Asp Val Arg
    2030                2035                2040

Asp Val Thr Ala Leu Asn Val Ser Thr Leu Lys Ala Tyr Phe Arg
    2045                2050                2055

Cys Asp Gly Tyr Lys Gly Tyr Asp Leu Val Tyr Ser Pro Gln Ser
    2060                2065                2070

Gly Phe Thr Cys Val Ser Pro Cys Ser Arg Gly Tyr Cys Asp His
    2075                2080                2085

Gly Gly Gln Cys Gln His Leu Pro Ser Gly Pro Arg Cys Ser Cys
    2090                2095                2100

Val Ser Phe Ser Ile Tyr Thr Ala Trp Gly Glu His Cys Glu His
    2105                2110                2115

Leu Ser Met Lys Leu Asp Ala Phe Phe Gly Ile Phe Phe Gly Ala
    2120                2125                2130

Leu Gly Gly Leu Leu Leu Leu Gly Val Gly Thr Phe Val Val Leu
    2135                2140                2145

Arg Phe Trp Gly Cys Ser Gly Ala Arg Phe Ser Tyr Phe Leu Asn
    2150                2155                2160

Ser Ala Glu Ala Leu Pro
    2165

<210> SEQ ID NO 15
<211> LENGTH: 377
<212> TYPE: PRT
<213> ORGANISM: Homo sapiens
<220> FEATURE:
<223> OTHER INFORMATION: MUC7

<400> SEQUENCE: 15

Met Lys Thr Leu Pro Leu Phe Val Cys Ile Cys Ala Leu Ser Ala Cys
1               5                   10                  15

Phe Ser Phe Ser Glu Gly Arg Glu Arg Asp His Glu Leu Arg His Arg
                20                  25                  30

Arg His His Gln Ser Pro Lys Ser His Phe Glu Leu Pro His Tyr
            35                  40                  45

Pro Gly Leu Leu Ala His Gln Lys Pro Phe Ile Arg Lys Ser Tyr Lys
    50                  55                  60
```

Cys Leu His Lys Arg Cys Arg Pro Lys Leu Pro Pro Ser Pro Asn Asn
65                  70                  75                  80

Pro Pro Lys Phe Pro Asn Pro His Gln Pro Lys His Pro Asp Lys
            85                  90                  95

Asn Ser Ser Val Val Asn Pro Thr Leu Val Ala Thr Thr Gln Ile Pro
                100                 105                 110

Ser Val Thr Phe Pro Ser Ala Ser Thr Lys Ile Thr Thr Leu Pro Asn
                115                 120                 125

Val Thr Phe Leu Pro Gln Asn Ala Thr Thr Ile Ser Ser Arg Glu Asn
130             135                 140

Val Asn Thr Ser Ser Val Ala Thr Leu Ala Pro Val Asn Ser Pro
145                 150                 155                 160

Ala Pro Gln Asp Thr Thr Ala Ala Pro Thr Pro Ser Ala Thr Thr
                165                 170                 175

Pro Ala Pro Pro Ser Ser Ser Ala Pro Pro Glu Thr Thr Ala Ala Pro
                180                 185                 190

Pro Thr Pro Ser Ala Thr Thr Gln Ala Pro Pro Ser Ser Ser Ala Pro
                195                 200                 205

Pro Glu Thr Thr Ala Ala Pro Pro Thr Pro Pro Ala Thr Thr Pro Ala
    210                 215                 220

Pro Pro Ser Ser Ser Ala Pro Pro Glu Thr Thr Ala Ala Pro Pro Thr
225                 230                 235                 240

Pro Ser Ala Thr Thr Pro Ala Pro Leu Ser Ser Ser Ala Pro Pro Glu
                245                 250                 255

Thr Thr Ala Val Pro Pro Thr Pro Ser Ala Thr Thr Leu Asp Pro Ser
                260                 265                 270

Ser Ala Ser Ala Pro Pro Glu Thr Thr Ala Ala Pro Pro Thr Pro Ser
                275                 280                 285

Ala Thr Thr Pro Ala Pro Pro Ser Ser Pro Ala Pro Gln Glu Thr Thr
            290                 295                 300

Ala Ala Pro Ile Thr Thr Pro Asn Ser Ser Pro Thr Thr Leu Ala Pro
305                 310                 315                 320

Asp Thr Ser Glu Thr Ser Ala Ala Pro Thr His Gln Thr Thr Thr Ser
                325                 330                 335

Val Thr Thr Gln Thr Thr Thr Thr Lys Gln Pro Thr Ser Ala Pro Gly
                340                 345                 350

Gln Asn Lys Ile Ser Arg Phe Leu Leu Tyr Met Lys Asn Leu Leu Asn
                355                 360                 365

Arg Ile Ile Asp Asp Met Val Glu Gln
            370                 375

<210> SEQ ID NO 16
<211> LENGTH: 5654
<212> TYPE: PRT
<213> ORGANISM: Homo sapiens
<220> FEATURE:
<223> OTHER INFORMATION: MUC5AC

<400> SEQUENCE: 16

Met Ser Val Gly Arg Arg Lys Leu Ala Leu Leu Trp Ala Leu Ala Leu
1               5                   10                  15

Ala Leu Ala Cys Thr Arg His Thr Gly His Ala Gln Asp Gly Ser Ser
                20                  25                  30

Glu Ser Ser Tyr Lys His His Pro Ala Leu Ser Pro Ile Ala Arg Gly
                35                  40                  45

```
Pro Ser Gly Val Pro Leu Arg Gly Ala Thr Val Phe Pro Ser Leu Arg
    50                  55                  60

Thr Ile Pro Val Val Arg Ala Ser Asn Pro Ala His Asn Gly Arg Val
65                  70                  75                  80

Cys Ser Thr Trp Gly Ser Phe His Tyr Lys Thr Phe Asp Gly Asp Val
                85                  90                  95

Phe Arg Phe Pro Gly Leu Cys Asn Tyr Val Phe Ser Glu His Cys Gly
            100                 105                 110

Ala Ala Tyr Glu Asp Phe Asn Ile Gln Leu Arg Arg Ser Gln Glu Ser
        115                 120                 125

Ala Ala Pro Thr Leu Ser Arg Val Leu Met Lys Val Asp Gly Val Val
    130                 135                 140

Ile Gln Leu Thr Lys Gly Ser Val Leu Val Asn Gly His Pro Val Leu
145                 150                 155                 160

Leu Pro Phe Ser Gln Ser Gly Val Leu Ile Gln Gln Ser Ser Ser Tyr
            165                 170                 175

Thr Lys Val Glu Ala Arg Leu Gly Leu Val Leu Met Trp Asn His Asp
        180                 185                 190

Asp Ser Leu Leu Leu Glu Leu Asp Thr Lys Tyr Ala Asn Lys Thr Cys
    195                 200                 205

Gly Leu Cys Gly Asp Phe Asn Gly Met Pro Val Val Ser Glu Leu Leu
    210                 215                 220

Ser His Asn Thr Lys Leu Thr Pro Met Glu Phe Gly Asn Leu Gln Lys
225                 230                 235                 240

Met Asp Asp Pro Thr Asp Gln Cys Gln Asp Pro Val Pro Glu Pro Pro
            245                 250                 255

Arg Asn Cys Ser Thr Gly Phe Gly Ile Cys Glu Glu Leu Leu His Gly
        260                 265                 270

Gln Leu Phe Ser Gly Cys Val Ala Leu Val Asp Val Gly Ser Tyr Leu
    275                 280                 285

Glu Ala Cys Arg Gln Asp Leu Cys Phe Cys Glu Asp Thr Asp Leu Leu
    290                 295                 300

Ser Cys Val Cys His Thr Leu Ala Glu Tyr Ser Arg Gln Cys Thr His
305                 310                 315                 320

Ala Gly Gly Leu Pro Gln Asp Trp Arg Gly Pro Asp Phe Cys Pro Gln
            325                 330                 335

Lys Cys Pro Asn Asn Met Gln Tyr His Glu Cys Arg Ser Pro Cys Ala
        340                 345                 350

Asp Thr Cys Ser Asn Gln Glu His Ser Arg Ala Cys Glu Asp His Cys
    355                 360                 365

Val Ala Gly Cys Phe Cys Pro Glu Gly Thr Val Leu Asp Asp Ile Gly
    370                 375                 380

Gln Thr Gly Cys Val Pro Val Ser Lys Cys Ala Cys Val Tyr Asn Gly
385                 390                 395                 400

Ala Ala Tyr Ala Pro Gly Ala Thr Tyr Ser Thr Asp Cys Thr Asn Cys
            405                 410                 415

Thr Cys Ser Gly Gly Arg Trp Ser Cys Gln Glu Val Pro Cys Pro Gly
        420                 425                 430

Thr Cys Ser Val Leu Gly Gly Ala His Phe Ser Thr Phe Asp Gly Lys
    435                 440                 445

Gln Tyr Thr Val His Gly Asp Cys Ser Tyr Val Leu Thr Lys Pro Cys
450                 455                 460
```

```
Asp Ser Ser Ala Phe Thr Val Leu Ala Glu Leu Arg Arg Cys Gly Leu
465                 470                 475                 480

Thr Asp Ser Glu Thr Cys Leu Lys Ser Val Thr Leu Ser Leu Asp Gly
            485                 490                 495

Ala Gln Thr Val Val Ile Lys Ala Ser Gly Glu Val Phe Leu Asn
            500                 505                 510

Gln Ile Tyr Thr Gln Leu Pro Ile Ser Ala Ala Asn Val Thr Ile Phe
            515                 520                 525

Arg Pro Ser Thr Phe Phe Ile Ala Gln Thr Ser Leu Gly Leu Gln
            530                 535                 540

Leu Asn Leu Gln Leu Val Pro Thr Met Gln Leu Phe Met Gln Leu Ala
545                 550                 555                 560

Pro Lys Leu Arg Gly Gln Thr Cys Gly Leu Cys Gly Asn Phe Asn Ser
                565                 570                 575

Ile Gln Ala Asp Asp Phe Arg Thr Leu Ser Gly Val Val Glu Ala Thr
            580                 585                 590

Ala Ala Ala Phe Phe Asn Thr Phe Lys Thr Gln Ala Ala Cys Pro Asn
            595                 600                 605

Ile Arg Asn Ser Phe Glu Asp Pro Cys Ser Leu Ser Val Glu Asn Glu
            610                 615                 620

Lys Tyr Ala Gln His Trp Cys Ser Gln Leu Thr Asp Ala Asp Gly Pro
625                 630                 635                 640

Phe Gly Arg Cys His Ala Ala Val Lys Pro Gly Thr Tyr Tyr Ser Asn
                645                 650                 655

Cys Met Phe Asp Thr Cys Asn Cys Glu Arg Ser Glu Asp Cys Leu Cys
                660                 665                 670

Ala Ala Leu Ser Ser Tyr Val His Ala Cys Ala Ala Lys Gly Val Gln
            675                 680                 685

Leu Gly Gly Trp Arg Asp Gly Val Cys Thr Lys Pro Met Thr Thr Cys
690                 695                 700

Pro Lys Ser Met Thr Tyr His Tyr Val Ser Thr Cys Gln Pro Thr
705                 710                 715                 720

Cys Arg Ser Leu Ser Glu Gly Asp Ile Thr Cys Ser Val Gly Phe Ile
                725                 730                 735

Pro Val Asp Gly Cys Ile Cys Pro Lys Gly Thr Phe Leu Asp Asp Thr
            740                 745                 750

Gly Lys Cys Val Gln Ala Ser Asn Cys Pro Cys Tyr His Arg Gly Ser
            755                 760                 765

Met Ile Pro Asn Gly Glu Ser His Asp Ser Gly Ala Ile Cys Thr
770                 775                 780

Cys Thr His Gly Lys Leu Ser Cys Ile Gly Gly Gln Ala Pro Ala Pro
785                 790                 795                 800

Val Cys Ala Ala Pro Met Val Phe Phe Asp Cys Arg Asn Ala Thr Pro
            805                 810                 815

Gly Asp Thr Gly Ala Gly Cys Gln Lys Ser Cys His Thr Leu Asp Met
            820                 825                 830

Thr Cys Tyr Ser Pro Gln Cys Val Pro Gly Cys Val Cys Pro Asp Gly
            835                 840                 845

Leu Val Ala Asp Gly Glu Gly Gly Cys Ile Thr Ala Glu Asp Cys Pro
            850                 855                 860

Cys Val His Asn Glu Ala Ser Tyr Arg Ala Gly Gln Thr Ile Arg Val
865                 870                 875                 880

Gly Cys Asn Thr Cys Thr Cys Asp Ser Arg Met Trp Arg Cys Thr Asp
```

885             890             895
Asp Pro Cys Leu Ala Thr Cys Ala Val Tyr Gly Asp Gly His Tyr Leu
            900             905             910
Thr Phe Asp Gly Gln Ser Tyr Ser Phe Asn Gly Asp Cys Glu Tyr Thr
            915             920             925
Leu Val Gln Asn His Cys Gly Gly Lys Asp Ser Thr Gln Asp Ser Phe
            930             935             940
Arg Val Val Thr Glu Asn Val Pro Cys Gly Thr Gly Thr Thr Cys
945             950             955             960
Ser Lys Ala Ile Lys Ile Phe Leu Gly Gly Phe Glu Leu Lys Leu Ser
            965             970             975
His Gly Lys Val Glu Val Ile Gly Thr Asp Glu Ser Gln Glu Val Pro
            980             985             990
Tyr Thr Ile Arg Gln Met Gly Ile Tyr Leu Val Val Asp Thr Asp Ile
            995             1000            1005
Gly Leu Val Leu Leu Trp Asp Lys Lys Thr Ser Ile Phe Ile Asn
     1010            1015            1020
Leu Ser Pro Glu Phe Lys Gly Arg Val Cys Gly Leu Cys Gly Asn
     1025            1030            1035
Phe Asp Asp Ile Ala Val Asn Asp Phe Ala Thr Arg Ser Arg Ser
     1040            1045            1050
Val Val Gly Asp Val Leu Glu Phe Gly Asn Ser Trp Lys Leu Ser
     1055            1060            1065
Pro Ser Cys Pro Asp Ala Leu Ala Pro Lys Asp Pro Cys Thr Ala
     1070            1075            1080
Asn Pro Phe Arg Lys Ser Trp Ala Gln Lys Gln Cys Ser Ile Leu
     1085            1090            1095
His Gly Pro Thr Phe Ala Ala Cys His Ala His Val Glu Pro Ala
     1100            1105            1110
Arg Tyr Tyr Glu Ala Cys Val Asn Asp Ala Cys Ala Cys Asp Ser
     1115            1120            1125
Gly Gly Asp Cys Glu Cys Phe Cys Thr Ala Val Ala Ala Tyr Ala
     1130            1135            1140
Gln Ala Cys His Glu Val Gly Leu Cys Val Ser Trp Arg Thr Pro
     1145            1150            1155
Ser Ile Cys Pro Leu Phe Cys Asp Tyr Tyr Asn Pro Glu Gly Gln
     1160            1165            1170
Cys Glu Trp His Tyr Gln Pro Cys Gly Val Pro Cys Leu Arg Thr
     1175            1180            1185
Cys Arg Asn Pro Arg Gly Asp Cys Leu Arg Asp Val Arg Gly Leu
     1190            1195            1200
Glu Gly Cys Tyr Pro Lys Cys Pro Pro Glu Ala Pro Ile Phe Asp
     1205            1210            1215
Glu Asp Lys Met Gln Cys Val Ala Thr Cys Pro Thr Pro Pro Leu
     1220            1225            1230
Pro Pro Arg Cys His Val His Gly Lys Ser Tyr Arg Pro Gly Ala
     1235            1240            1245
Val Val Pro Ser Asp Lys Asn Cys Gln Ser Cys Leu Cys Thr Glu
     1250            1255            1260
Arg Gly Val Glu Cys Thr Tyr Lys Ala Glu Ala Cys Val Cys Thr
     1265            1270            1275
Tyr Asn Gly Gln Arg Phe His Pro Gly Asp Val Ile Tyr His Thr
     1280            1285            1290

```
Thr Asp Gly Thr Gly Gly Cys Ile Ser Ala Arg Cys Gly Ala Asn
    1295            1300                1305

Gly Thr Ile Glu Arg Arg Val Tyr Pro Cys Ser Pro Thr Thr Pro
    1310            1315                1320

Val Pro Pro Thr Thr Phe Ser Phe Ser Thr Pro Pro Leu Val Val
    1325            1330                1335

Ser Ser Thr His Thr Pro Ser Asn Gly Pro Ser Ser Ala His Thr
    1340            1345                1350

Gly Pro Pro Ser Ser Ala Trp Pro Thr Thr Ala Gly Thr Ser Pro
    1355            1360                1365

Arg Thr Arg Leu Pro Thr Ala Ser Ala Ser Leu Pro Pro Val Cys
    1370            1375                1380

Gly Glu Lys Cys Leu Trp Ser Pro Trp Met Asp Val Ser Arg Pro
    1385            1390                1395

Gly Arg Gly Thr Asp Ser Gly Asp Phe Asp Thr Leu Glu Asn Leu
    1400            1405                1410

Arg Ala His Gly Tyr Arg Val Cys Glu Ser Pro Arg Ser Val Glu
    1415            1420                1425

Cys Arg Ala Glu Asp Ala Pro Gly Val Pro Leu Arg Ala Leu Gly
    1430            1435                1440

Gln Arg Val Gln Cys Ser Pro Asp Val Gly Leu Thr Cys Arg Asn
    1445            1450                1455

Arg Glu Gln Ala Ser Gly Leu Cys Tyr Asn Tyr Gln Ile Arg Val
    1460            1465                1470

Gln Cys Cys Thr Pro Leu Pro Cys Ser Thr Ser Ser Ser Pro Ala
    1475            1480                1485

Gln Thr Thr Pro Pro Thr Thr Ser Lys Thr Thr Glu Thr Arg Ala
    1490            1495                1500

Ser Gly Ser Ser Ala Pro Ser Ser Thr Pro Gly Thr Val Ser Leu
    1505            1510                1515

Ser Thr Ala Arg Thr Thr Pro Ala Pro Gly Thr Ala Thr Ser Val
    1520            1525                1530

Lys Lys Thr Phe Ser Thr Pro Ser Pro Pro Val Pro Ala Thr
    1535            1540                1545

Ser Thr Ser Ser Met Ser Thr Thr Ala Pro Gly Thr Ser Val Val
    1550            1555                1560

Ser Ser Lys Pro Thr Pro Thr Glu Pro Ser Thr Ser Cys Leu
    1565            1570                1575

Gln Glu Leu Cys Thr Trp Thr Glu Trp Ile Asp Gly Ser Tyr Pro
    1580            1585                1590

Ala Pro Gly Ile Asn Gly Gly Asp Phe Asp Thr Phe Gln Asn Leu
    1595            1600                1605

Arg Asp Glu Gly Tyr Thr Phe Cys Glu Ser Pro Arg Ser Val Gln
    1610            1615                1620

Cys Arg Ala Glu Ser Phe Pro Asn Thr Pro Leu Ala Asp Leu Gly
    1625            1630                1635

Gln Asp Val Ile Cys Ser His Thr Glu Gly Leu Ile Cys Leu Asn
    1640            1645                1650

Lys Asn Gln Leu Pro Pro Ile Cys Tyr Asn Tyr Glu Ile Arg Ile
    1655            1660                1665

Gln Cys Cys Glu Thr Val Asn Val Cys Arg Asp Ile Thr Arg Leu
    1670            1675                1680
```

```
Pro Lys Thr Val Ala Thr Thr Arg Pro Thr Pro His Pro Thr Gly
    1685                1690                1695

Ala Gln Thr Gln Thr Thr Phe Thr Thr His Met Pro Ser Ala Ser
    1700                1705                1710

Thr Glu Gln Pro Thr Ala Thr Ser Arg Gly Gly Pro Thr Ala Thr
    1715                1720                1725

Ser Val Thr Gln Gly Thr His Thr Thr Leu Val Thr Arg Asn Cys
    1730                1735                1740

His Pro Arg Cys Thr Trp Thr Lys Trp Phe Asp Val Asp Phe Pro
    1745                1750                1755

Ser Pro Gly Pro His Gly Gly Asp Lys Glu Thr Tyr Asn Asn Ile
    1760                1765                1770

Ile Arg Ser Gly Glu Lys Ile Cys Arg Arg Pro Glu Glu Ile Thr
    1775                1780                1785

Arg Leu Gln Cys Arg Ala Lys Ser His Pro Glu Val Ser Ile Glu
    1790                1795                1800

His Leu Gly Gln Val Val Gln Cys Ser Arg Glu Glu Gly Leu Val
    1805                1810                1815

Cys Arg Asn Gln Asp Gln Gln Gly Pro Phe Lys Met Cys Leu Asn
    1820                1825                1830

Tyr Glu Val Arg Val Leu Cys Cys Glu Thr Pro Arg Gly Cys His
    1835                1840                1845

Met Thr Ser Thr Pro Gly Ser Thr Ser Ser Ser Pro Ala Gln Thr
    1850                1855                1860

Thr Pro Ser Thr Thr Ser Lys Thr Thr Glu Thr Gln Ala Ser Gly
    1865                1870                1875

Ser Ser Ala Pro Ser Ser Thr Pro Gly Thr Val Ser Leu Ser Thr
    1880                1885                1890

Ala Arg Thr Thr Pro Ala Pro Gly Thr Ala Thr Ser Val Lys Lys
    1895                1900                1905

Thr Phe Ser Thr Pro Ser Pro Pro Val Pro Ala Thr Ser Thr
    1910                1915                1920

Ser Ser Met Ser Thr Thr Ala Pro Gly Thr Ser Val Val Ser Ser
    1925                1930                1935

Lys Pro Thr Pro Thr Glu Pro Ser Thr Ser Ser Cys Leu Gln Glu
    1940                1945                1950

Leu Cys Thr Trp Thr Glu Trp Ile Asp Gly Ser Tyr Pro Ala Pro
    1955                1960                1965

Gly Ile Asn Gly Gly Asp Phe Asp Thr Phe Gln Asn Leu Arg Asp
    1970                1975                1980

Glu Gly Tyr Thr Phe Cys Glu Ser Pro Arg Ser Val Gln Cys Arg
    1985                1990                1995

Ala Glu Ser Phe Pro Asn Thr Pro Leu Ala Asp Leu Gly Gln Asp
    2000                2005                2010

Val Ile Cys Ser His Thr Glu Gly Leu Ile Cys Leu Asn Lys Asn
    2015                2020                2025

Gln Leu Pro Pro Ile Cys Tyr Asn Tyr Glu Ile Arg Ile Gln Cys
    2030                2035                2040

Cys Glu Thr Val Asn Val Cys Arg Asp Ile Thr Arg Pro Pro Lys
    2045                2050                2055

Thr Val Ala Thr Thr Arg Pro Thr Pro His Pro Thr Gly Ala Gln
    2060                2065                2070

Thr Gln Thr Thr Phe Thr Thr His Met Pro Ser Ala Ser Thr Glu
```

-continued

```
                2075                2080                2085
Gln Pro Thr Ala Thr Ser Arg Gly Gly Pro Thr Ala Thr Ser Val
    2090                2095                2100
Thr Gln Gly Thr His Thr Thr Pro Val Thr Arg Asn Cys His Pro
    2105                2110                2115
Arg Cys Thr Trp Thr Thr Trp Phe Asp Val Asp Phe Pro Ser Pro
    2120                2125                2130
Gly Pro His Gly Gly Asp Lys Glu Thr Tyr Asn Asn Ile Ile Arg
    2135                2140                2145
Ser Gly Glu Lys Ile Cys Arg Arg Pro Glu Glu Ile Thr Arg Leu
    2150                2155                2160
Gln Cys Arg Ala Lys Ser His Pro Glu Val Ser Ile Glu His Leu
    2165                2170                2175
Gly Gln Val Val Gln Cys Ser Arg Glu Glu Gly Leu Val Cys Arg
    2180                2185                2190
Asn Gln Asp Gln Gln Gly Pro Phe Lys Met Cys Leu Asn Tyr Glu
    2195                2200                2205
Val Arg Val Leu Cys Cys Glu Thr Pro Lys Gly Cys Pro Val Thr
    2210                2215                2220
Ser Thr Pro Val Thr Ala Pro Ser Thr Pro Ser Gly Arg Ala Thr
    2225                2230                2235
Ser Pro Thr Gln Ser Thr Ser Ser Trp Gln Lys Ser Arg Thr Thr
    2240                2245                2250
Thr Leu Val Thr Thr Ser Thr Ser Thr Pro Gln Thr Ser Thr
    2255                2260                2265
Thr Tyr Ala His Thr Thr Ser Thr Thr Ser Ala Pro Thr Ala Arg
    2270                2275                2280
Thr Thr Ser Ala Pro Thr Thr Arg Thr Thr Ser Ala Ser Pro Ala
    2285                2290                2295
Ser Thr Thr Ser Gly Pro Gly Asn Thr Pro Ser Pro Val Pro Thr
    2300                2305                2310
Thr Ser Thr Ile Ser Ala Pro Thr Thr Ser Ile Thr Ser Ala Pro
    2315                2320                2325
Thr Thr Ser Thr Thr Ser Ala Pro Thr Ser Ser Thr Thr Ser Gly
    2330                2335                2340
Pro Gly Thr Thr Pro Ser Pro Val Pro Thr Thr Ser Ile Thr Ser
    2345                2350                2355
Ala Pro Thr Thr Ser Thr Thr Ser Ala Pro Thr Thr Ser Thr Thr
    2360                2365                2370
Ser Ala Arg Thr Ser Ser Thr Thr Ser Ala Thr Thr Thr Ser Arg
    2375                2380                2385
Ile Ser Gly Pro Glu Thr Thr Pro Ser Pro Val Pro Thr Thr Ser
    2390                2395                2400
Thr Thr Ser Ala Thr Thr Thr Ser Thr Thr Ser Ala Pro Thr Thr
    2405                2410                2415
Ser Thr Ser Ala Pro Thr Ser Ser Thr Thr Ser Ser Pro Gln
    2420                2425                2430
Thr Ser Thr Thr Ser Ala Pro Thr Thr Ser Thr Thr Ser Gly Pro
    2435                2440                2445
Gly Thr Thr Pro Ser Pro Val Pro Thr Thr Ser Thr Thr Ser Ala
    2450                2455                2460
Pro Thr Thr Arg Thr Thr Ser Ala Pro Lys Ser Ser Thr Thr Ser
    2465                2470                2475
```

```
Ala Ala Thr Thr Ser Thr Thr Ser Gly Pro Glu Thr Thr Pro Arg
2480                2485                2490

Pro Val Pro Thr Thr Ser Thr Thr Ser Ser Pro Thr Thr Ser Thr
    2495                2500                2505

Thr Ser Ala Pro Thr Thr Ser Thr Thr Ser Ala Ser Thr Thr Ser
    2510                2515                2520

Thr Thr Ser Gly Ala Gly Thr Thr Pro Ser Pro Val Pro Thr Thr
    2525                2530                2535

Ser Thr Thr Ser Ala Pro Thr Thr Ser Thr Thr Ser Ala Pro Ile
    2540                2545                2550

Ser Ser Thr Thr Ser Ala Thr Thr Thr Ser Thr Thr Ser Gly Pro
    2555                2560                2565

Gly Thr Thr Pro Ser Pro Val Pro Thr Thr Ser Thr Thr Ser Ala
    2570                2575                2580

Pro Thr Thr Ser Thr Thr Ser Gly Pro Gly Thr Thr Pro Ser Ala
    2585                2590                2595

Val Pro Thr Thr Ser Ile Thr Ser Ala Pro Thr Thr Ser Thr Asn
    2600                2605                2610

Ser Ala Pro Ile Ser Ser Thr Thr Ser Ala Thr Thr Thr Ser Arg
    2615                2620                2625

Ile Ser Gly Pro Glu Thr Thr Pro Ser Pro Val Pro Thr Ala Ser
    2630                2635                2640

Thr Thr Ser Ala Ser Thr Thr Ser Thr Thr Ser Gly Pro Gly Thr
    2645                2650                2655

Thr Pro Ser Pro Val Pro Thr Thr Ser Thr Ile Ser Val Pro Thr
    2660                2665                2670

Thr Ser Thr Thr Ser Ala Ser Thr Thr Ser Thr Thr Ser Ala Ser
    2675                2680                2685

Thr Thr Ser Thr Thr Ser Gly Pro Gly Thr Thr Pro Ser Pro Val
    2690                2695                2700

Pro Thr Thr Ser Thr Thr Ser Ala Pro Thr Thr Ser Thr Thr Ser
    2705                2710                2715

Ala Pro Thr Thr Ser Thr Ile Ser Ala Pro Thr Thr Ser Thr Thr
    2720                2725                2730

Ser Ala Thr Thr Thr Ser Thr Thr Ser Ala Pro Thr Pro Arg Arg
    2735                2740                2745

Thr Ser Ala Pro Thr Thr Ser Thr Ile Ser Ala Ser Thr Thr Ser
    2750                2755                2760

Thr Thr Ser Ala Thr Thr Thr Ser Thr Thr Ser Ala Thr Thr Thr
    2765                2770                2775

Ser Thr Ile Ser Ala Pro Thr Thr Ser Thr Thr Leu Ser Pro Thr
    2780                2785                2790

Thr Ser Thr Thr Ser Thr Thr Ile Thr Ser Thr Thr Ser Ala Pro
    2795                2800                2805

Ile Ser Ser Thr Thr Ser Thr Pro Gln Thr Ser Thr Thr Ser Ala
    2810                2815                2820

Pro Thr Thr Ser Thr Thr Ser Gly Pro Gly Thr Thr Ser Ser Pro
    2825                2830                2835

Val Pro Thr Thr Ser Thr Thr Ser Ala Pro Thr Thr Ser Thr Thr
    2840                2845                2850

Ser Ala Pro Thr Thr Arg Thr Thr Ser Val Pro Thr Ser Ser Thr
    2855                2860                2865
```

-continued

| | | | | | | | | | | | |
|---|---|---|---|---|---|---|---|---|---|---|---|
|Thr|Ser|Thr|Ala|Thr|Thr|Ser|Thr|Ser|Gly|Pro|Gly|Thr|Thr|
| |2870| | | |2875| | | |2880| | | | |

Thr Ser Thr Ala Thr Thr Ser Thr Ser Gly Pro Gly Thr Thr
    2870              2875              2880

Pro Ser Pro Val Pro Thr Thr Ser Thr Thr Ser Ala Pro Thr Thr
    2885              2890              2895

Arg Thr Thr Ser Ala Pro Thr Thr Ser Thr Thr Ser Ala Pro Thr
    2900              2905              2910

Thr Ser Thr Thr Ser Ala Pro Thr Ser Ser Thr Thr Ser Ala Thr
    2915              2920              2925

Thr Thr Ser Thr Ile Ser Val Pro Thr Thr Ser Thr Thr Ser Val
    2930              2935              2940

Pro Gly Thr Thr Pro Ser Pro Val Pro Thr Thr Ser Thr Ile Ser
    2945              2950              2955

Val Pro Thr Thr Ser Thr Thr Ser Ala Ser Thr Thr Ser Thr Thr
    2960              2965              2970

Ser Gly Pro Gly Thr Thr Pro Ser Pro Val Pro Thr Thr Ser Thr
    2975              2980              2985

Thr Ser Ala Pro Thr Thr Ser Thr Thr Ser Ala Pro Thr Thr Ser
    2990              2995              3000

Thr Ile Ser Ala Pro Thr Thr Ser Thr Pro Ser Ala Pro Thr Thr
    3005              3010              3015

Ser Thr Thr Leu Ala Pro Thr Thr Ser Thr Thr Ser Ala Pro Thr
    3020              3025              3030

Thr Ser Thr Thr Ser Thr Pro Thr Ser Ser Thr Thr Ser Ser Pro
    3035              3040              3045

Gln Thr Ser Thr Thr Ser Ala Ser Thr Thr Ser Ile Thr Ser Gly
    3050              3055              3060

Pro Gly Thr Thr Pro Ser Pro Val Pro Thr Thr Ser Thr Thr Ser
    3065              3070              3075

Ala Pro Thr Thr Ser Thr Thr Ser Ala Ala Thr Thr Ser Thr Ile
    3080              3085              3090

Ser Ala Pro Thr Thr Ser Thr Thr Ser Ala Pro Thr Thr Ser Thr
    3095              3100              3105

Thr Ser Ala Ser Thr Ala Ser Lys Thr Ser Gly Leu Gly Thr Thr
    3110              3115              3120

Pro Ser Pro Ile Pro Thr Thr Ser Thr Thr Ser Pro Pro Thr Thr
    3125              3130              3135

Ser Thr Thr Ser Ala Ser Thr Ala Ser Lys Thr Ser Gly Pro Gly
    3140              3145              3150

Thr Thr Pro Ser Pro Val Pro Thr Thr Ser Thr Ile Phe Ala Pro
    3155              3160              3165

Arg Thr Ser Thr Thr Ser Ala Ser Thr Thr Ser Thr Thr Pro Gly
    3170              3175              3180

Pro Gly Thr Thr Pro Ser Pro Val Pro Thr Thr Ser Thr Ala Ser
    3185              3190              3195

Val Ser Lys Thr Ser Thr Ser His Val Ser Ile Ser Lys Thr Thr
    3200              3205              3210

His Ser Gln Pro Val Thr Arg Asp Cys His Leu Arg Cys Thr Trp
    3215              3220              3225

Thr Lys Trp Phe Asp Ile Asp Phe Pro Ser Pro Gly Pro His Gly
    3230              3235              3240

Gly Asp Lys Glu Thr Tyr Asn Asn Ile Ile Arg Ser Gly Glu Lys
    3245              3250              3255

Ile Cys Arg Arg Pro Glu Glu Ile Thr Arg Leu Gln Cys Arg Ala

|           |           |           |           |           |           |           |           |           |           |
|-----------|-----------|-----------|-----------|-----------|-----------|-----------|-----------|-----------|-----------|
|           |           |     3260  |           |           |     3265  |           |           |     3270  |           |
| Glu  3275 | Ser       | His       | Pro       | Glu  3280 | Val       | Ser       | Ile       | Glu  3285 | His       | Leu       | Gly       | Gln       | Val       | Val       |

Glu Ser His Pro Glu Val Ser Ile Glu His Leu Gly Gln Val Val
3275            3280                3285

Gln Cys Ser Arg Glu Glu Gly Leu Val Cys Arg Asn Gln Asp Gln
3290            3295                3300

Gln Gly Pro Phe Lys Met Cys Leu Asn Tyr Glu Val Arg Val Leu
3305            3310                3315

Cys Cys Glu Thr Pro Lys Gly Cys Pro Val Thr Ser Thr Pro Val
3320            3325                3330

Thr Ala Pro Ser Thr Pro Ser Gly Arg Ala Thr Ser Pro Thr Gln
3335            3340                3345

Ser Thr Ser Ser Trp Gln Lys Ser Arg Thr Thr Thr Leu Val Thr
3350            3355                3360

Thr Ser Thr Thr Ser Thr Pro Gln Thr Ser Thr Thr Ser Ala Pro
3365            3370                3375

Thr Thr Ser Thr Thr Ser Ala Pro Thr Thr Ser Thr Thr Ser Ala
3380            3385                3390

Pro Thr Thr Ser Thr Thr Ser Thr Pro Gln Thr Ser Ile Ser Ser
3395            3400                3405

Ala Pro Thr Ser Ser Thr Thr Ser Ala Pro Thr Ser Ser Thr Ile
3410            3415                3420

Ser Ala Arg Thr Thr Ser Ile Ile Ser Ala Pro Thr Thr Ser Thr
3425            3430                3435

Thr Ser Ser Pro Thr Thr Ser Thr Thr Ser Ala Thr Thr Thr Ser
3440            3445                3450

Thr Thr Ser Ala Pro Thr Ser Ser Thr Thr Ser Thr Pro Gln Thr
3455            3460                3465

Ser Lys Thr Ser Ala Ala Thr Ser Ser Thr Thr Ser Gly Ser Gly
3470            3475                3480

Thr Thr Pro Ser Pro Val Thr Thr Thr Ser Thr Ala Ser Val Ser
3485            3490                3495

Lys Thr Ser Thr Ser His Val Ser Val Ser Lys Thr Thr His Ser
3500            3505                3510

Gln Pro Val Thr Arg Asp Cys His Pro Arg Cys Thr Trp Thr Lys
3515            3520                3525

Trp Phe Asp Val Asp Phe Pro Ser Pro Gly Pro His Gly Gly Asp
3530            3535                3540

Lys Glu Thr Tyr Asn Asn Ile Ile Arg Ser Gly Glu Lys Ile Cys
3545            3550                3555

Arg Arg Pro Glu Glu Ile Thr Arg Leu Gln Cys Arg Ala Lys Ser
3560            3565                3570

His Pro Glu Val Ser Ile Glu His Leu Gly Gln Val Val Gln Cys
3575            3580                3585

Ser Arg Glu Glu Gly Leu Val Cys Arg Asn Gln Asp Gln Gln Gly
3590            3595                3600

Pro Phe Lys Met Cys Leu Asn Tyr Glu Val Arg Val Leu Cys Cys
3605            3610                3615

Glu Thr Pro Lys Gly Cys Pro Val Thr Ser Thr Ser Val Thr Ala
3620            3625                3630

Pro Ser Thr Pro Ser Gly Arg Ala Thr Ser Pro Thr Gln Ser Thr
3635            3640                3645

Ser Ser Trp Gln Lys Ser Arg Thr Thr Thr Leu Val Thr Ser Ser
3650            3655                3660

-continued

Ile Thr Ser Thr Thr Gln Thr Ser Thr Thr Ser Ala Pro Thr Thr
3665                3670                3675

Ser Thr Thr Pro Ala Ser Ile Pro Ser Thr Thr Ser Ala Pro Thr
3680                3685                3690

Thr Ser Thr Thr Ser Ala Pro Thr Thr Ser Thr Thr Ser Ala Pro
3695                3700                3705

Thr Thr Ser Thr Thr Ser Thr Pro Gln Thr Thr Thr Ser Ser Ala
3710                3715                3720

Pro Thr Ser Ser Thr Thr Ser Ala Pro Thr Thr Ser Thr Ile Ser
3725                3730                3735

Ala Pro Thr Thr Ser Thr Ile Ser Ala Pro Thr Thr Ser Thr Thr
3740                3745                3750

Ser Ala Pro Thr Ala Ser Thr Thr Ser Ala Pro Thr Ser Thr Ser
3755                3760                3765

Ser Ala Pro Thr Thr Asn Thr Thr Ser Ala Pro Thr Thr Ser Thr
3770                3775                3780

Thr Ser Ala Pro Ile Thr Ser Thr Ile Ser Ala Pro Thr Thr Ser
3785                3790                3795

Thr Thr Ser Thr Pro Gln Thr Ser Thr Ile Ser Ser Pro Thr Thr
3800                3805                3810

Ser Thr Thr Ser Thr Pro Gln Thr Ser Thr Thr Ser Ser Pro Thr
3815                3820                3825

Thr Ser Thr Thr Ser Ala Pro Thr Thr Ser Thr Thr Ser Ala Pro
3830                3835                3840

Thr Thr Ser Thr Thr Ser Thr Pro Gln Thr Ser Ile Ser Ser Ala
3845                3850                3855

Pro Thr Ser Ser Thr Thr Ser Ala Pro Thr Ala Ser Thr Ile Ser
3860                3865                3870

Ala Pro Thr Thr Ser Thr Thr Ser Phe His Thr Thr Ser Thr Thr
3875                3880                3885

Ser Pro Pro Thr Ser Ser Thr Ser Ser Thr Pro Gln Thr Ser Lys
3890                3895                3900

Thr Ser Ala Ala Thr Ser Ser Thr Thr Ser Gly Ser Gly Thr Thr
3905                3910                3915

Pro Ser Pro Val Pro Thr Thr Ser Thr Ala Ser Val Ser Lys Thr
3920                3925                3930

Ser Thr Ser His Val Ser Val Ser Lys Thr Thr His Ser Gln Pro
3935                3940                3945

Val Thr Arg Asp Cys His Pro Arg Cys Thr Trp Thr Lys Trp Phe
3950                3955                3960

Asp Val Asp Phe Pro Ser Pro Gly Pro His Gly Gly Asp Lys Glu
3965                3970                3975

Thr Tyr Asn Asn Ile Ile Arg Ser Gly Glu Lys Ile Cys Arg Arg
3980                3985                3990

Pro Glu Glu Ile Thr Arg Leu Gln Cys Arg Ala Glu Ser His Pro
3995                4000                4005

Glu Val Ser Ile Glu His Leu Gly Gln Val Val Gln Cys Ser Arg
4010                4015                4020

Glu Glu Gly Leu Val Cys Arg Asn Gln Asp Gln Gln Gly Pro Phe
4025                4030                4035

Lys Met Cys Leu Asn Tyr Glu Val Arg Val Leu Cys Cys Glu Thr
4040                4045                4050

-continued

```
Pro Lys Gly Cys Pro Val Thr Ser Thr Pro Val Thr Ala Pro Ser
4055                4060                4065

Thr Pro Ser Gly Arg Ala Thr Ser Pro Thr Gln Ser Thr Ser Ser
4070                4075                4080

Trp Gln Lys Ser Arg Thr Thr Leu Val Thr Thr Ser Thr Thr
4085                4090                4095

Ser Thr Pro Gln Thr Ser Thr Thr Ser Ala Pro Thr Thr Ser Thr
4100                4105                4110

Ile Pro Ala Ser Thr Pro Ser Thr Thr Ser Ala Pro Thr Thr Ser
4115                4120                4125

Thr Thr Ser Ala Pro Thr Thr Ser Thr Thr Ser Ala Pro Thr His
4130                4135                4140

Arg Thr Thr Ser Gly Pro Thr Thr Ser Thr Thr Leu Ala Pro Thr
4145                4150                4155

Thr Ser Thr Thr Ser Ala Pro Thr Thr Ser Thr Asn Ser Ala Pro
4160                4165                4170

Thr Thr Ser Thr Ile Ser Ala Ser Thr Thr Ser Thr Ile Ser Ala
4175                4180                4185

Pro Thr Thr Ser Thr Ile Ser Ser Pro Thr Ser Ser Thr Thr Ser
4190                4195                4200

Thr Pro Gln Thr Ser Lys Thr Ser Ala Ala Thr Ser Ser Thr Thr
4205                4210                4215

Ser Gly Ser Gly Thr Thr Pro Ser Pro Val Pro Thr Thr Ser Thr
4220                4225                4230

Thr Ser Ala Ser Thr Thr Ser Thr Thr Ser Ala Pro Thr Thr Ser
4235                4240                4245

Thr Thr Ser Gly Pro Gly Thr Pro Ser Pro Val Pro Ser Thr
4250                4255                4260

Ser Thr Thr Ser Ala Ala Thr Thr Ser Thr Thr Ser Ala Pro Thr
4265                4270                4275

Thr Arg Thr Thr Ser Ala Pro Thr Ser Ser Met Thr Ser Gly Pro
4280                4285                4290

Gly Thr Thr Pro Ser Pro Val Pro Thr Thr Ser Thr Thr Ser Ala
4295                4300                4305

Pro Thr Thr Ser Thr Thr Ser Gly Pro Gly Thr Thr Pro Ser Pro
4310                4315                4320

Val Pro Thr Thr Ser Thr Thr Ser Ala Pro Ile Thr Ser Thr Thr
4325                4330                4335

Ser Gly Pro Gly Ser Thr Pro Ser Pro Val Pro Thr Thr Ser Thr
4340                4345                4350

Thr Ser Ala Pro Thr Thr Ser Thr Thr Ser Ala Ser Thr Ala Ser
4355                4360                4365

Thr Thr Ser Gly Pro Gly Thr Pro Ser Pro Val Pro Thr Thr
4370                4375                4380

Ser Thr Thr Ser Ala Pro Thr Thr Arg Thr Thr Ser Ala Ser Thr
4385                4390                4395

Ala Ser Thr Thr Ser Gly Pro Gly Ser Thr Pro Ser Pro Val Pro
4400                4405                4410

Thr Thr Ser Thr Thr Ser Ala Pro Thr Thr Arg Thr Thr Pro Ala
4415                4420                4425

Ser Thr Ala Ser Thr Thr Ser Gly Pro Gly Thr Thr Pro Ser Pro
4430                4435                4440

Val Pro Thr Thr Ser Thr Thr Ser Ala Ser Thr Thr Ser Thr Ile
```

```
                4445                 4450                4455
Ser Leu Pro Thr Thr Ser Thr Thr Ser Ala Pro Ile Thr Ser Met
    4460                4465                4470

Thr Ser Gly Pro Gly Thr Thr Pro Ser Pro Val Pro Thr Thr Ser
    4475                4480                4485

Thr Thr Ser Ala Pro Thr Thr Ser Thr Thr Ser Ala Ser Thr Ala
    4490                4495                4500

Ser Thr Thr Ser Gly Pro Gly Thr Thr Pro Ser Pro Val Pro Thr
    4505                4510                4515

Thr Ser Thr Thr Ser Ala Pro Thr Thr Ser Thr Thr Ser Ala Ser
    4520                4525                4530

Thr Ala Ser Thr Thr Ser Gly Pro Gly Thr Ser Leu Ser Pro Val
    4535                4540                4545

Pro Thr Thr Ser Thr Thr Ser Ala Pro Thr Thr Ser Thr Thr Ser
    4550                4555                4560

Gly Pro Gly Thr Thr Pro Ser Pro Val Pro Thr Thr Ser Thr Thr
    4565                4570                4575

Ser Ala Pro Thr Thr Ser Thr Ser Gly Pro Gly Thr Thr Pro
    4580                4585                4590

Ser Pro Val Pro Thr Thr Ser Thr Thr Pro Val Ser Lys Thr Ser
    4595                4600                4605

Thr Ser His Leu Ser Val Ser Lys Thr Thr His Ser Gln Pro Val
    4610                4615                4620

Thr Ser Asp Cys His Pro Leu Cys Ala Trp Thr Lys Trp Phe Asp
    4625                4630                4635

Val Asp Phe Pro Ser Pro Gly Pro His Gly Gly Asp Lys Glu Thr
    4640                4645                4650

Tyr Asn Asn Ile Ile Arg Ser Gly Glu Lys Ile Cys Arg Arg Pro
    4655                4660                4665

Glu Glu Ile Thr Arg Leu Gln Cys Arg Ala Glu Ser His Pro Glu
    4670                4675                4680

Val Asn Ile Glu His Leu Gly Gln Val Val Gln Cys Ser Arg Glu
    4685                4690                4695

Glu Gly Leu Val Cys Arg Asn Gln Asp Gln Gln Gly Pro Phe Lys
    4700                4705                4710

Met Cys Leu Asn Tyr Glu Val Arg Val Leu Cys Cys Glu Thr Pro
    4715                4720                4725

Arg Gly Cys Pro Val Thr Ser Val Thr Pro Tyr Gly Thr Ser Pro
    4730                4735                4740

Thr Asn Ala Leu Tyr Pro Ser Leu Ser Thr Ser Met Val Ser Ala
    4745                4750                4755

Ser Val Ala Ser Thr Ser Val Ala Ser Ser Ser Val Ala Ser Ser
    4760                4765                4770

Ser Val Ala Tyr Ser Thr Gln Thr Cys Phe Cys Asn Val Ala Asp
    4775                4780                4785

Arg Leu Tyr Pro Ala Gly Ser Thr Ile Tyr Arg His Arg Asp Leu
    4790                4795                4800

Ala Gly His Cys Tyr Tyr Ala Leu Cys Ser Gln Asp Cys Gln Val
    4805                4810                4815

Val Arg Gly Val Asp Ser Asp Cys Pro Ser Thr Thr Leu Pro Pro
    4820                4825                4830

Ala Pro Ala Thr Ser Pro Ser Ile Ser Thr Ser Glu Pro Val Thr
    4835                4840                4845
```

-continued

Glu Leu Gly Cys Pro Asn Ala Val Pro Arg Lys Lys Gly Glu
    4850                4855                4860

Thr Trp Ala Thr Pro Asn Cys Ser Glu Ala Thr Cys Glu Gly Asn
    4865                4870                4875

Asn Val Ile Ser Leu Arg Pro Arg Thr Cys Pro Arg Val Glu Lys
    4880                4885                4890

Pro Thr Cys Ala Asn Gly Tyr Pro Ala Val Lys Val Ala Asp Gln
    4895                4900                4905

Asp Gly Cys Cys His His Tyr Gln Cys Gln Cys Val Cys Ser Gly
    4910                4915                4920

Trp Gly Asp Pro His Tyr Ile Thr Phe Asp Gly Thr Tyr Tyr Thr
    4925                4930                4935

Phe Leu Asp Asn Cys Thr Tyr Val Leu Val Gln Gln Ile Val Pro
    4940                4945                4950

Val Tyr Gly His Phe Arg Val Leu Val Asp Asn Tyr Phe Cys Gly
    4955                4960                4965

Ala Glu Asp Gly Leu Ser Cys Pro Arg Ser Ile Ile Leu Glu Tyr
    4970                4975                4980

His Gln Asp Arg Val Val Leu Thr Arg Lys Pro Val His Gly Val
    4985                4990                4995

Met Thr Asn Glu Ile Ile Phe Asn Asn Lys Val Val Ser Pro Gly
    5000                5005                5010

Phe Arg Lys Asn Gly Ile Val Val Ser Arg Ile Gly Val Lys Met
    5015                5020                5025

Tyr Ala Thr Ile Pro Glu Leu Gly Val Gln Val Met Phe Ser Gly
    5030                5035                5040

Leu Ile Phe Ser Val Glu Val Pro Phe Ser Lys Phe Ala Asn Asn
    5045                5050                5055

Thr Glu Gly Gln Cys Gly Thr Cys Thr Asn Asp Arg Lys Asp Glu
    5060                5065                5070

Cys Arg Thr Pro Arg Gly Thr Val Val Ala Ser Cys Ser Glu Met
    5075                5080                5085

Ser Gly Leu Trp Asn Val Ser Ile Pro Asp Gln Pro Ala Cys His
    5090                5095                5100

Arg Pro His Pro Thr Pro Thr Val Gly Pro Thr Thr Val Gly
    5105                5110                5115

Ser Thr Thr Val Gly Pro Thr Val Gly Ser Thr Thr Val Gly
    5120                5125                5130

Pro Thr Thr Pro Pro Ala Pro Cys Leu Pro Ser Pro Ile Cys Gln
    5135                5140                5145

Leu Ile Leu Ser Lys Val Phe Glu Pro Cys His Thr Val Ile Pro
    5150                5155                5160

Pro Leu Leu Phe Tyr Glu Gly Cys Val Phe Asp Arg Cys His Met
    5165                5170                5175

Thr Asp Leu Asp Val Val Cys Ser Ser Leu Glu Leu Tyr Ala Ala
    5180                5185                5190

Leu Cys Ala Ser His Asp Ile Cys Ile Asp Trp Arg Gly Arg Thr
    5195                5200                5205

Gly His Met Cys Pro Phe Thr Cys Pro Ala Asp Lys Val Tyr Gln
    5210                5215                5220

Pro Cys Gly Pro Ser Asn Pro Ser Tyr Cys Tyr Gly Asn Asp Ser
    5225                5230                5235

```
Ala Ser Leu Gly Ala Leu Pro Glu Ala Gly Pro Ile Thr Glu Gly
    5240                5245                5250

Cys Phe Cys Pro Glu Gly Met Thr Leu Phe Ser Thr Ser Ala Gln
    5255                5260                5265

Val Cys Val Pro Thr Gly Cys Pro Arg Cys Leu Gly Pro His Gly
    5270                5275                5280

Glu Pro Val Lys Val Gly His Thr Val Gly Met Asp Cys Gln Glu
    5285                5290                5295

Cys Thr Cys Glu Ala Ala Thr Trp Thr Leu Thr Cys Arg Pro Lys
    5300                5305                5310

Leu Cys Pro Leu Pro Pro Ala Cys Pro Leu Pro Gly Phe Val Pro
    5315                5320                5325

Val Pro Ala Ala Pro Gln Ala Gly Gln Cys Cys Pro Gln Tyr Ser
    5330                5335                5340

Cys Ala Cys Asn Thr Ser Arg Cys Pro Ala Pro Val Gly Cys Pro
    5345                5350                5355

Glu Gly Ala Arg Ala Ile Pro Thr Tyr Gln Glu Gly Ala Cys Cys
    5360                5365                5370

Pro Val Gln Asn Cys Ser Trp Thr Val Cys Ser Ile Asn Gly Thr
    5375                5380                5385

Leu Tyr Gln Pro Gly Ala Val Val Ser Ser Leu Cys Glu Thr
    5390                5395                5400

Cys Arg Cys Glu Leu Pro Gly Gly Pro Pro Ser Asp Ala Phe Val
    5405                5410                5415

Val Ser Cys Glu Thr Gln Ile Cys Asn Thr His Cys Pro Val Gly
    5420                5425                5430

Phe Glu Tyr Gln Glu Gln Ser Gly Gln Cys Cys Gly Thr Cys Val
    5435                5440                5445

Gln Val Ala Cys Val Thr Asn Thr Ser Lys Ser Pro Ala His Leu
    5450                5455                5460

Phe Tyr Pro Gly Glu Thr Trp Ser Asp Ala Gly Asn His Cys Val
    5465                5470                5475

Thr His Gln Cys Glu Lys His Gln Asp Gly Leu Val Val Val Thr
    5480                5485                5490

Thr Lys Lys Ala Cys Pro Pro Leu Ser Cys Ser Leu Asp Glu Ala
    5495                5500                5505

Arg Met Ser Lys Asp Gly Cys Cys Arg Phe Cys Pro Pro Pro Pro
    5510                5515                5520

Pro Pro Tyr Gln Asn Gln Ser Thr Cys Ala Val Tyr His Arg Ser
    5525                5530                5535

Leu Ile Ile Gln Gln Gln Gly Cys Ser Ser Ser Glu Pro Val Arg
    5540                5545                5550

Leu Ala Tyr Cys Arg Gly Asn Cys Gly Asp Ser Ser Met Tyr
    5555                5560                5565

Ser Leu Glu Gly Asn Thr Val Glu His Arg Cys Gln Cys Cys Gln
    5570                5575                5580

Glu Leu Arg Thr Ser Leu Arg Asn Val Thr Leu His Cys Thr Asp
    5585                5590                5595

Gly Ser Ser Arg Ala Phe Ser Tyr Thr Glu Val Glu Glu Cys Gly
    5600                5605                5610

Cys Met Gly Arg Arg Cys Pro Ala Pro Gly Asp Thr Gln His Ser
    5615                5620                5625

Glu Glu Ala Glu Pro Glu Pro Ser Gln Glu Ala Glu Ser Gly Ser
```

```
               5630                5635                5640
Trp Glu Arg Gly Val Pro Val Ser Pro Met His
        5645                5650

<210> SEQ ID NO 17
<211> LENGTH: 5762
<212> TYPE: PRT
<213> ORGANISM: Homo sapiens
<220> FEATURE:
<223> OTHER INFORMATION: MUC5B

<400> SEQUENCE: 17

Met Gly Ala Pro Ser Ala Cys Arg Thr Leu Val Leu Ala Leu Ala Ala
1               5                   10                  15

Met Leu Val Val Pro Gln Ala Glu Thr Gln Gly Pro Val Glu Pro Ser
            20                  25                  30

Trp Glu Asn Ala Gly His Thr Met Asp Gly Gly Ala Pro Thr Ser Ser
        35                  40                  45

Pro Thr Arg Arg Val Ser Phe Val Pro Val Thr Val Phe Pro Ser
    50                  55                  60

Leu Ser Pro Leu Asn Pro Ala His Asn Gly Arg Val Cys Ser Thr Trp
65                  70                  75                  80

Gly Asp Phe His Tyr Lys Thr Phe Asp Gly Asp Val Phe Arg Phe Pro
                85                  90                  95

Gly Leu Cys Asn Tyr Val Phe Ser Glu His Cys Arg Ala Ala Tyr Glu
            100                 105                 110

Asp Phe Asn Val Gln Leu Arg Arg Gly Leu Val Gly Ser Arg Pro Val
        115                 120                 125

Val Thr Arg Val Val Ile Lys Ala Gln Gly Leu Val Leu Glu Ala Ser
    130                 135                 140

Asn Gly Ser Val Leu Ile Asn Gly Gln Arg Glu Glu Leu Pro Tyr Ser
145                 150                 155                 160

Arg Thr Gly Leu Leu Val Glu Gln Ser Gly Asp Tyr Ile Lys Val Ser
                165                 170                 175

Ile Arg Leu Val Leu Thr Phe Leu Trp Asn Gly Glu Asp Ser Ala Leu
            180                 185                 190

Leu Glu Leu Asp Pro Lys Tyr Ala Asn Gln Thr Cys Gly Leu Cys Gly
        195                 200                 205

Asp Phe Asn Gly Leu Pro Ala Phe Asn Glu Phe Tyr Ala His Asn Ala
    210                 215                 220

Arg Leu Thr Pro Leu Gln Phe Gly Asn Leu Gln Lys Leu Asp Gly Pro
225                 230                 235                 240

Thr Glu Gln Cys Pro Asp Pro Leu Pro Leu Pro Ala Gly Asn Cys Thr
                245                 250                 255

Asp Glu Glu Gly Ile Cys His Arg Thr Leu Leu Gly Pro Ala Phe Ala
            260                 265                 270

Glu Cys His Ala Leu Val Asp Ser Thr Ala Tyr Leu Ala Ala Cys Ala
        275                 280                 285

Gln Asp Leu Cys Arg Cys Pro Thr Cys Pro Cys Ala Thr Phe Val Glu
    290                 295                 300

Tyr Ser Arg Gln Cys Ala His Ala Gly Gly Gln Pro Arg Asn Trp Arg
305                 310                 315                 320

Cys Pro Glu Leu Cys Pro Arg Thr Cys Pro Leu Asn Met Gln His Gln
                325                 330                 335

Glu Cys Gly Ser Pro Cys Thr Asp Thr Cys Ser Asn Pro Gln Arg Ala
```

-continued

```
                340                 345                 350
Gln Leu Cys Glu Asp His Cys Val Asp Gly Cys Phe Cys Pro Pro Gly
            355                 360                 365

Thr Val Leu Asp Asp Ile Thr His Ser Gly Cys Leu Pro Leu Gly Gln
        370                 375                 380

Cys Pro Cys Thr His Gly Gly Arg Thr Tyr Ser Pro Gly Thr Ser Phe
385                 390                 395                 400

Asn Thr Thr Cys Ser Ser Cys Thr Cys Ser Gly Gly Leu Trp Gln Cys
                405                 410                 415

Gln Asp Leu Pro Cys Pro Gly Thr Cys Ser Val Gln Gly Gly Ala His
            420                 425                 430

Ile Ser Thr Tyr Asp Glu Lys Leu Tyr Asp Leu His Gly Asp Cys Ser
        435                 440                 445

Tyr Val Leu Ser Lys Lys Cys Ala Asp Ser Ser Phe Thr Val Leu Ala
    450                 455                 460

Glu Leu Arg Lys Cys Gly Leu Thr Asp Asn Glu Asn Cys Leu Lys Ala
465                 470                 475                 480

Val Thr Leu Ser Leu Asp Gly Asp Thr Ala Ile Arg Val Gln Ala
                485                 490                 495

Asp Gly Gly Val Phe Leu Asn Ser Ile Tyr Thr Gln Leu Pro Leu Ser
            500                 505                 510

Ala Ala Asn Ile Thr Leu Phe Thr Pro Ser Ser Phe Ile Val Val
        515                 520                 525

Gln Thr Gly Leu Gly Leu Gln Leu Leu Val Gln Leu Pro Leu Met
    530                 535                 540

Gln Val Phe Val Arg Leu Asp Pro Ala His Gln Gly Gln Met Cys Gly
545                 550                 555                 560

Leu Cys Gly Asn Phe Asn Gln Asn Gln Ala Asp Asp Phe Thr Ala Leu
                565                 570                 575

Ser Gly Val Val Glu Ala Thr Gly Ala Ala Phe Ala Asn Thr Trp Lys
            580                 585                 590

Ala Gln Ala Ala Cys Ala Asn Ala Arg Asn Ser Phe Glu Asp Pro Cys
        595                 600                 605

Ser Leu Ser Val Glu Asn Glu Asn Tyr Ala Arg His Trp Cys Ser Arg
    610                 615                 620

Leu Thr Asp Pro Asn Ser Ala Phe Ser Arg Cys His Ser Ile Ile Asn
625                 630                 635                 640

Pro Lys Pro Phe His Ser Asn Cys Met Phe Asp Thr Cys Asn Cys Glu
                645                 650                 655

Arg Ser Glu Asp Cys Leu Cys Ala Ala Leu Ser Ser Tyr Val His Ala
            660                 665                 670

Cys Ala Ala Lys Gly Val Gln Leu Ser Asp Trp Arg Asp Gly Val Cys
        675                 680                 685

Thr Lys Tyr Met Gln Asn Cys Pro Lys Ser Gln Arg Tyr Ala Tyr Val
    690                 695                 700

Val Asp Ala Cys Gln Pro Thr Cys Arg Gly Leu Ser Glu Ala Asp Val
705                 710                 715                 720

Thr Cys Ser Val Ser Phe Val Pro Val Asp Gly Cys Thr Cys Pro Ala
                725                 730                 735

Gly Thr Phe Leu Asn Asp Ala Gly Ala Cys Val Pro Ala Gln Glu Cys
            740                 745                 750

Pro Cys Tyr Ala His Gly Thr Val Leu Ala Pro Gly Glu Val Val His
        755                 760                 765
```

```
Asp Glu Gly Ala Val Cys Ser Cys Thr Gly Gly Lys Leu Ser Cys Leu
        770                 775                 780
Gly Ala Ser Leu Gln Lys Ser Thr Gly Cys Ala Ala Pro Met Val Tyr
785                 790                 795                 800
Leu Asp Cys Ser Asn Ser Ser Ala Gly Thr Pro Gly Ala Glu Cys Leu
                805                 810                 815
Arg Ser Cys His Thr Leu Asp Val Gly Cys Phe Ser Thr His Cys Val
                820                 825                 830
Ser Gly Cys Val Cys Pro Pro Gly Leu Val Ser Asp Gly Ser Gly Gly
                835                 840                 845
Cys Ile Ala Glu Glu Asp Cys Pro Cys Val His Asn Glu Ala Thr Tyr
        850                 855                 860
Lys Pro Gly Glu Thr Ile Arg Val Asp Cys Asn Thr Cys Thr Cys Arg
865                 870                 875                 880
Asn Arg Arg Trp Glu Cys Ser His Arg Leu Cys Leu Gly Thr Cys Val
                885                 890                 895
Ala Tyr Gly Asp Gly His Phe Ile Thr Phe Asp Gly Asp Arg Tyr Ser
                900                 905                 910
Phe Glu Gly Ser Cys Glu Tyr Ile Leu Ala Gln Asp Tyr Cys Gly Asp
                915                 920                 925
Asn Thr Thr His Gly Thr Phe Arg Ile Val Thr Glu Asn Ile Pro Cys
                930                 935                 940
Gly Thr Thr Gly Thr Thr Cys Ser Lys Ala Ile Lys Leu Phe Val Glu
945                 950                 955                 960
Ser Tyr Glu Leu Ile Leu Gln Glu Gly Thr Phe Lys Ala Val Ala Arg
                965                 970                 975
Gly Pro Gly Gly Asp Pro Pro Tyr Lys Ile Arg Tyr Met Gly Ile Phe
                980                 985                 990
Leu Val Ile Glu Thr His Gly Met Ala Val Ser Trp Asp Arg Lys Thr
                995                 1000                1005
Ser Val Phe Ile Arg Leu His Gln Asp Tyr Lys Gly Arg Val Cys
        1010                1015                1020
Gly Leu Cys Gly Asn Phe Asp Asp Asn Ala Ile Asn Asp Phe Ala
        1025                1030                1035
Thr Arg Ser Arg Ser Val Val Gly Asp Ala Leu Glu Phe Gly Asn
        1040                1045                1050
Ser Trp Lys Leu Ser Pro Ser Cys Pro Asp Ala Leu Ala Pro Lys
        1055                1060                1065
Asp Pro Cys Thr Ala Asn Pro Phe Arg Lys Ser Trp Ala Gln Lys
        1070                1075                1080
Gln Cys Ser Ile Leu His Gly Pro Thr Phe Ala Ala Cys Arg Ser
        1085                1090                1095
Gln Val Asp Ser Thr Lys Tyr Tyr Glu Ala Cys Val Asn Asp Ala
        1100                1105                1110
Cys Ala Cys Asp Ser Gly Gly Asp Cys Glu Cys Phe Cys Thr Ala
        1115                1120                1125
Val Ala Ala Tyr Ala Gln Ala Cys His Asp Ala Gly Leu Cys Val
        1130                1135                1140
Ser Trp Arg Thr Pro Asp Thr Cys Pro Leu Phe Cys Asp Phe Tyr
        1145                1150                1155
Asn Pro His Gly Gly Cys Glu Trp His Tyr Gln Pro Cys Gly Ala
        1160                1165                1170
```

```
Pro Cys Leu Lys Thr Cys Arg Asn Pro Ser Gly His Cys Leu Val
1175                1180                1185

Asp Leu Pro Gly Leu Glu Gly Cys Tyr Pro Lys Cys Pro Pro Ser
1190                1195                1200

Gln Pro Phe Phe Asn Glu Asp Gln Met Lys Cys Val Ala Gln Cys
1205                1210                1215

Gly Cys Tyr Asp Lys Asp Gly Asn Tyr Tyr Asp Val Gly Ala Arg
1220                1225                1230

Val Pro Thr Ala Glu Asn Cys Gln Ser Cys Asn Cys Thr Pro Ser
1235                1240                1245

Gly Ile Gln Cys Ala His Ser Leu Glu Ala Cys Thr Cys Thr Tyr
1250                1255                1260

Glu Asp Arg Thr Tyr Ser Tyr Gln Asp Val Ile Tyr Asn Thr Thr
1265                1270                1275

Asp Gly Leu Gly Ala Cys Leu Ile Ala Ile Cys Gly Ser Asn Gly
1280                1285                1290

Thr Ile Ile Arg Lys Ala Val Ala Cys Pro Gly Thr Pro Ala Thr
1295                1300                1305

Thr Pro Phe Thr Phe Thr Thr Ala Trp Val Pro His Ser Thr Thr
1310                1315                1320

Ser Pro Ala Leu Pro Val Ser Thr Val Cys Val Arg Glu Val Cys
1325                1330                1335

Arg Trp Ser Ser Trp Tyr Asn Gly His Arg Pro Glu Pro Gly Leu
1340                1345                1350

Gly Gly Gly Asp Phe Glu Thr Phe Glu Asn Leu Arg Gln Arg Gly
1355                1360                1365

Tyr Gln Val Cys Pro Val Leu Ala Asp Ile Glu Cys Arg Ala Ala
1370                1375                1380

Gln Leu Pro Asp Met Pro Leu Glu Glu Leu Gly Gln Gln Val Asp
1385                1390                1395

Cys Asp Arg Met Arg Gly Leu Met Cys Ala Asn Ser Gln Gln Ser
1400                1405                1410

Pro Pro Leu Cys His Asp Tyr Glu Leu Arg Val Leu Cys Cys Glu
1415                1420                1425

Tyr Val Pro Cys Gly Pro Ser Pro Ala Pro Gly Thr Ser Pro Gln
1430                1435                1440

Pro Ser Leu Ser Ala Ser Thr Glu Pro Ala Val Pro Thr Pro Thr
1445                1450                1455

Gln Thr Thr Ala Thr Glu Lys Thr Thr Leu Trp Val Thr Pro Ser
1460                1465                1470

Ile Arg Ser Thr Ala Ala Leu Thr Ser Gln Thr Gly Ser Ser Ser
1475                1480                1485

Gly Pro Val Thr Val Thr Pro Ser Ala Pro Gly Thr Thr Thr Cys
1490                1495                1500

Gln Pro Arg Cys Gln Trp Thr Glu Trp Phe Asp Glu Asp Tyr Pro
1505                1510                1515

Lys Ser Glu Gln Leu Gly Gly Asp Val Glu Ser Tyr Asp Lys Ile
1520                1525                1530

Arg Ala Ala Gly Gly His Leu Cys Gln Gln Pro Lys Asp Ile Glu
1535                1540                1545

Cys Gln Ala Glu Ser Phe Pro Asn Trp Thr Leu Ala Gln Val Gly
1550                1555                1560

Gln Lys Val His Cys Asp Val His Phe Gly Leu Val Cys Arg Asn
```

```
              1565                1570                1575

Trp Glu Gln Glu Gly Val Phe Lys Met Cys Tyr Asn Tyr Arg Ile
    1580                1585                1590

Arg Val Leu Cys Cys Ser Asp Asp His Cys Arg Gly Arg Ala Thr
    1595                1600                1605

Thr Pro Pro Pro Thr Thr Glu Leu Glu Thr Ala Thr Thr Thr Thr
    1610                1615                1620

Thr Gln Ala Leu Phe Ser Thr Pro Gln Pro Thr Ser Ser Pro Gly
    1625                1630                1635

Leu Thr Arg Ala Pro Pro Ala Ser Thr Thr Ala Val Pro Thr Leu
    1640                1645                1650

Ser Glu Gly Leu Thr Ser Pro Arg Tyr Thr Ser Thr Leu Gly Thr
    1655                1660                1665

Ala Thr Thr Gly Gly Pro Thr Thr Pro Ala Gly Ser Thr Glu Pro
    1670                1675                1680

Thr Val Pro Gly Val Ala Thr Ser Thr Leu Pro Thr Arg Ser Ala
    1685                1690                1695

Leu Pro Gly Thr Thr Gly Ser Leu Gly Thr Trp Arg Pro Ser Gln
    1700                1705                1710

Pro Pro Thr Leu Ala Pro Thr Thr Met Ala Thr Ser Arg Ala Arg
    1715                1720                1725

Pro Thr Gly Thr Ala Ser Thr Ala Ser Lys Glu Pro Leu Thr Thr
    1730                1735                1740

Ser Leu Ala Pro Thr Leu Thr Ser Glu Leu Ser Thr Ser Gln Ala
    1745                1750                1755

Glu Thr Ser Thr Pro Arg Thr Glu Thr Thr Met Ser Pro Leu Thr
    1760                1765                1770

Asn Thr Thr Thr Ser Gln Gly Thr Thr Arg Cys Gln Pro Lys Cys
    1775                1780                1785

Glu Trp Thr Glu Trp Phe Asp Val Asp Phe Pro Thr Ser Gly Val
    1790                1795                1800

Ala Gly Gly Asp Met Glu Thr Phe Glu Asn Ile Arg Ala Ala Gly
    1805                1810                1815

Gly Lys Met Cys Trp Ala Pro Lys Ser Ile Glu Cys Arg Ala Glu
    1820                1825                1830

Asn Tyr Pro Glu Val Ser Ile Asp Gln Val Gly Gln Val Leu Thr
    1835                1840                1845

Cys Ser Leu Glu Thr Gly Leu Thr Cys Lys Asn Glu Asp Gln Thr
    1850                1855                1860

Gly Arg Phe Asn Met Cys Phe Asn Tyr Asn Val Arg Val Leu Cys
    1865                1870                1875

Cys Asp Asp Tyr Ser His Cys Pro Ser Thr Pro Ala Thr Ser Ser
    1880                1885                1890

Thr Ala Thr Pro Ser Ser Thr Pro Gly Thr Thr Trp Ile Leu Thr
    1895                1900                1905

Lys Pro Thr Thr Thr Ala Thr Thr Thr Ala Ser Thr Gly Ser Thr
    1910                1915                1920

Ala Thr Pro Thr Ser Thr Leu Arg Thr Ala Pro Pro Lys Val
    1925                1930                1935

Leu Thr Thr Thr Ala Thr Thr Pro Thr Val Thr Ser Ser Lys Ala
    1940                1945                1950

Thr Pro Ser Ser Ser Pro Gly Thr Ala Thr Ala Leu Pro Ala Leu
    1955                1960                1965
```

```
Arg Ser Thr Ala Thr Thr Pro Thr Ala Thr Ser Val Thr Pro Ile
    1970            1975            1980

Pro Ser Ser Ser Leu Gly Thr Thr Trp Thr Arg Leu Ser Gln Thr
    1985            1990            1995

Thr Thr Pro Thr Ala Thr Met Ser Thr Ala Thr Pro Ser Ser Thr
    2000            2005            2010

Pro Glu Thr Ala His Thr Ser Thr Val Leu Thr Ala Thr Ala Thr
    2015            2020            2025

Thr Thr Gly Ala Thr Gly Ser Val Ala Thr Pro Ser Ser Thr Pro
    2030            2035            2040

Gly Thr Ala His Thr Thr Lys Val Pro Thr Thr Thr Thr Thr Gly
    2045            2050            2055

Phe Thr Ala Thr Pro Ser Ser Ser Pro Gly Thr Ala Leu Thr Pro
    2060            2065            2070

Pro Val Trp Ile Ser Thr Thr Thr Thr Pro Thr Thr Arg Gly Ser
    2075            2080            2085

Thr Val Thr Pro Ser Ser Ile Pro Gly Thr Thr His Thr Ala Thr
    2090            2095            2100

Val Leu Thr Thr Thr Thr Thr Thr Val Ala Thr Gly Ser Met Ala
    2105            2110            2115

Thr Pro Ser Ser Ser Thr Gln Thr Ser Gly Thr Pro Pro Ser Leu
    2120            2125            2130

Thr Thr Thr Ala Thr Thr Ile Thr Ala Thr Gly Ser Thr Thr Asn
    2135            2140            2145

Pro Ser Ser Thr Pro Gly Thr Thr Pro Ile Pro Pro Val Leu Thr
    2150            2155            2160

Thr Thr Ala Thr Thr Pro Ala Ala Thr Ser Asn Thr Val Thr Pro
    2165            2170            2175

Ser Ser Ala Leu Gly Thr Thr His Thr Pro Pro Val Pro Asn Thr
    2180            2185            2190

Met Ala Thr Thr His Gly Arg Ser Leu Pro Pro Ser Ser Pro His
    2195            2200            2205

Thr Val Arg Thr Ala Trp Thr Ser Ala Thr Ser Gly Ile Leu Gly
    2210            2215            2220

Thr Thr His Ile Thr Glu Pro Ser Thr Val Thr Ser His Thr Leu
    2225            2230            2235

Ala Ala Thr Thr Gly Thr Thr Gln His Ser Thr Pro Ala Leu Ser
    2240            2245            2250

Ser Pro His Pro Ser Ser Arg Thr Thr Glu Ser Pro Pro Ser Pro
    2255            2260            2265

Gly Thr Thr Thr Pro Gly His Thr Thr Ala Thr Ser Arg Thr Thr
    2270            2275            2280

Ala Thr Ala Thr Pro Ser Lys Thr Arg Thr Ser Thr Leu Leu Pro
    2285            2290            2295

Ser Ser Pro Thr Ser Ala Pro Ile Thr Thr Val Val Thr Met Gly
    2300            2305            2310

Cys Glu Pro Gln Cys Ala Trp Ser Glu Trp Leu Asp Tyr Ser Tyr
    2315            2320            2325

Pro Met Pro Gly Pro Ser Gly Gly Asp Phe Asp Thr Tyr Ser Asn
    2330            2335            2340

Ile Arg Ala Ala Gly Gly Ala Val Cys Glu Gln Pro Leu Gly Leu
    2345            2350            2355
```

```
Glu Cys Arg Ala Gln Ala Gln Pro Gly Val Pro Leu Arg Glu Leu
    2360                2365                2370
Gly Gln Val Val Glu Cys Ser Leu Asp Phe Gly Leu Val Cys Arg
    2375                2380                2385
Asn Arg Glu Gln Val Gly Lys Phe Lys Met Cys Phe Asn Tyr Glu
    2390                2395                2400
Ile Arg Val Phe Cys Cys Asn Tyr Gly His Cys Pro Ser Thr Pro
    2405                2410                2415
Ala Thr Ser Ser Thr Ala Met Pro Ser Ser Thr Pro Gly Thr Thr
    2420                2425                2430
Trp Ile Leu Thr Glu Leu Thr Thr Ala Thr Thr Thr Glu Ser
    2435                2440                2445
Thr Gly Ser Thr Ala Thr Pro Ser Ser Thr Pro Gly Thr Thr Trp
    2450                2455                2460
Ile Leu Thr Glu Pro Ser Thr Thr Ala Thr Val Thr Val Pro Thr
    2465                2470                2475
Gly Ser Thr Ala Thr Ala Ser Ser Thr Gln Ala Thr Ala Gly Thr
    2480                2485                2490
Pro His Val Ser Thr Thr Ala Thr Thr Pro Thr Val Thr Ser Ser
    2495                2500                2505
Lys Ala Thr Pro Phe Ser Ser Pro Gly Thr Ala Thr Ala Leu Pro
    2510                2515                2520
Ala Leu Arg Ser Thr Ala Thr Thr Pro Thr Ala Thr Ser Phe Thr
    2525                2530                2535
Ala Ile Pro Ser Ser Ser Leu Gly Thr Thr Trp Thr Arg Leu Ser
    2540                2545                2550
Gln Thr Thr Thr Pro Thr Ala Thr Met Ser Thr Ala Thr Pro Ser
    2555                2560                2565
Ser Thr Pro Glu Thr Val His Thr Ser Thr Val Leu Thr Thr Thr
    2570                2575                2580
Ala Thr Thr Thr Gly Ala Thr Gly Ser Val Ala Thr Pro Ser Ser
    2585                2590                2595
Thr Pro Gly Thr Ala His Thr Thr Lys Val Leu Thr Thr Thr Thr
    2600                2605                2610
Thr Gly Phe Thr Ala Thr Pro Ser Ser Ser Pro Gly Thr Ala Arg
    2615                2620                2625
Thr Leu Pro Val Trp Ile Ser Thr Thr Thr Thr Pro Thr Thr Arg
    2630                2635                2640
Gly Ser Thr Val Thr Pro Ser Ser Ile Pro Gly Thr Thr His Thr
    2645                2650                2655
Pro Thr Val Leu Thr Thr Thr Thr Thr Thr Val Ala Thr Gly Ser
    2660                2665                2670
Met Ala Thr Pro Ser Ser Ser Thr Gln Thr Ser Gly Thr Pro Pro
    2675                2680                2685
Ser Leu Thr Thr Thr Ala Thr Thr Ile Thr Ala Thr Gly Ser Thr
    2690                2695                2700
Thr Asn Pro Ser Ser Thr Pro Gly Thr Thr Pro Ile Pro Pro Val
    2705                2710                2715
Leu Thr Thr Thr Ala Thr Thr Pro Ala Ala Thr Ser Ser Thr Val
    2720                2725                2730
Thr Pro Ser Ser Ala Leu Gly Thr Thr His Thr Pro Pro Val Pro
    2735                2740                2745
Asn Thr Thr Ala Thr Thr His Gly Arg Ser Leu Ser Pro Ser Ser
```

-continued

```
                2750                2755                2760
Pro His Thr Val Arg Thr Ala Trp Thr Ser Ala Thr Ser Gly Thr
        2765                2770                2775
Leu Gly Thr Thr His Ile Thr Glu Pro Ser Thr Gly Thr Ser His
        2780                2785                2790
Thr Pro Ala Ala Thr Thr Gly Thr Thr Gln His Ser Thr Pro Ala
        2795                2800                2805
Leu Ser Ser Pro His Pro Ser Ser Arg Thr Thr Glu Ser Pro Pro
        2810                2815                2820
Ser Pro Gly Thr Thr Thr Pro Gly His Thr Arg Ala Thr Ser Arg
        2825                2830                2835
Thr Thr Ala Thr Ala Thr Pro Ser Lys Thr Arg Thr Ser Thr Leu
        2840                2845                2850
Leu Pro Ser Ser Pro Thr Ser Ala Pro Ile Thr Thr Val Val Thr
        2855                2860                2865
Met Gly Cys Glu Pro Gln Cys Ala Trp Ser Glu Trp Leu Asp Tyr
        2870                2875                2880
Ser Tyr Pro Met Pro Gly Pro Ser Gly Gly Asp Phe Asp Thr Tyr
        2885                2890                2895
Ser Asn Ile Arg Ala Ala Gly Gly Ala Val Cys Glu Gln Pro Leu
        2900                2905                2910
Gly Leu Glu Cys Arg Ala Gln Ala Gln Pro Gly Val Pro Leu Arg
        2915                2920                2925
Glu Leu Gly Gln Val Val Glu Cys Ser Leu Asp Phe Gly Leu Val
        2930                2935                2940
Cys Arg Asn Arg Glu Gln Val Gly Lys Phe Lys Met Cys Phe Asn
        2945                2950                2955
Tyr Glu Ile Arg Val Phe Cys Cys Asn Tyr Gly His Cys Pro Ser
        2960                2965                2970
Thr Pro Ala Thr Ser Ser Thr Ala Thr Pro Ser Ser Thr Pro Gly
        2975                2980                2985
Thr Thr Trp Ile Leu Thr Glu Gln Thr Thr Ala Ala Thr Thr Thr
        2990                2995                3000
Ala Thr Thr Gly Ser Thr Ala Ile Pro Ser Ser Thr Pro Gly Thr
        3005                3010                3015
Ala Pro Pro Pro Lys Val Leu Thr Ser Thr Ala Thr Thr Pro Thr
        3020                3025                3030
Ala Thr Ser Ser Lys Ala Thr Ser Ser Ser Ser Pro Arg Thr Ala
        3035                3040                3045
Thr Thr Leu Pro Val Leu Thr Ser Thr Ala Thr Lys Ser Thr Ala
        3050                3055                3060
Thr Ser Phe Thr Pro Ile Pro Ser Phe Thr Leu Gly Thr Thr Gly
        3065                3070                3075
Thr Leu Pro Glu Gln Thr Thr Thr Pro Met Ala Thr Met Ser Thr
        3080                3085                3090
Ile His Pro Ser Ser Thr Pro Glu Thr Thr His Thr Ser Thr Val
        3095                3100                3105
Leu Thr Thr Lys Ala Thr Thr Thr Arg Ala Thr Ser Ser Met Ser
        3110                3115                3120
Thr Pro Ser Ser Thr Pro Gly Thr Thr Trp Ile Leu Thr Glu Leu
        3125                3130                3135
Thr Thr Ala Ala Thr Thr Thr Ala Ala Thr Gly Pro Thr Ala Thr
        3140                3145                3150
```

```
Pro Ser Ser Thr Pro Gly Thr Thr Trp Ile Leu Thr Glu Pro Ser
3155                3160                3165

Thr Thr Ala Thr Val Thr Val Pro Thr Gly Ser Thr Ala Thr Ala
3170                3175                3180

Ser Ser Thr Arg Ala Thr Ala Gly Thr Leu Lys Val Leu Thr Ser
3185                3190                3195

Thr Ala Thr Thr Pro Thr Val Ile Ser Ser Arg Ala Thr Pro Ser
3200                3205                3210

Ser Ser Pro Gly Thr Ala Thr Ala Leu Pro Ala Leu Arg Ser Thr
3215                3220                3225

Ala Thr Thr Pro Thr Ala Thr Ser Val Thr Ala Ile Pro Ser Ser
3230                3235                3240

Ser Leu Gly Thr Ala Trp Thr Arg Leu Ser Gln Thr Thr Thr Pro
3245                3250                3255

Thr Ala Thr Met Ser Thr Ala Thr Pro Ser Ser Thr Pro Glu Thr
3260                3265                3270

Val His Thr Ser Thr Val Leu Thr Thr Thr Thr Thr Thr Thr Arg
3275                3280                3285

Ala Thr Gly Ser Val Ala Thr Pro Ser Ser Thr Pro Gly Thr Ala
3290                3295                3300

His Thr Thr Lys Val Pro Thr Thr Thr Thr Thr Gly Phe Thr Ala
3305                3310                3315

Thr Pro Ser Ser Ser Pro Gly Thr Ala Leu Thr Pro Pro Val Trp
3320                3325                3330

Ile Ser Thr Thr Thr Thr Pro Thr Thr Arg Gly Ser Thr Val Thr
3335                3340                3345

Pro Ser Ser Ile Pro Gly Thr Thr His Thr Ala Thr Val Leu Thr
3350                3355                3360

Thr Thr Thr Thr Thr Val Ala Thr Gly Ser Met Ala Thr Pro Ser
3365                3370                3375

Ser Ser Thr Gln Thr Ser Gly Thr Pro Pro Ser Leu Thr Thr Thr
3380                3385                3390

Ala Thr Thr Ile Thr Ala Thr Gly Ser Thr Thr Asn Pro Ser Ser
3395                3400                3405

Thr Pro Gly Thr Thr Pro Ile Pro Pro Val Leu Thr Thr Thr Ala
3410                3415                3420

Thr Thr Pro Ala Ala Thr Ser Ser Thr Val Thr Pro Ser Ser Ala
3425                3430                3435

Leu Gly Thr Thr His Thr Pro Pro Val Pro Asn Thr Thr Ala Thr
3440                3445                3450

Thr His Gly Arg Ser Leu Pro Pro Ser Ser Pro His Thr Val Arg
3455                3460                3465

Thr Ala Trp Thr Ser Ala Thr Ser Gly Ile Leu Gly Thr Thr His
3470                3475                3480

Ile Thr Glu Pro Ser Thr Val Thr Ser His Thr Pro Ala Ala Thr
3485                3490                3495

Thr Ser Thr Thr Gln His Ser Thr Pro Ala Leu Ser Ser Pro His
3500                3505                3510

Pro Ser Ser Arg Thr Thr Glu Ser Pro Pro Ser Pro Gly Thr Thr
3515                3520                3525

Thr Pro Gly His Thr Arg Gly Thr Ser Arg Thr Thr Ala Thr Ala
3530                3535                3540
```

-continued

```
Thr Pro Ser Lys Thr Arg Thr Ser Thr Leu Leu Pro Ser Ser Pro
3545                3550                3555

Thr Ser Ala Pro Ile Thr Val Val Thr Thr Gly Cys Glu Pro
3560                3565                3570

Gln Cys Ala Trp Ser Glu Trp Leu Asp Tyr Ser Tyr Pro Met Pro
3575                3580                3585

Gly Pro Ser Gly Gly Asp Phe Asp Thr Tyr Ser Asn Ile Arg Ala
3590                3595                3600

Ala Gly Gly Ala Val Cys Glu Gln Pro Leu Gly Leu Glu Cys Arg
3605                3610                3615

Ala Gln Ala Gln Pro Gly Val Pro Leu Arg Glu Leu Gly Gln Val
3620                3625                3630

Val Glu Cys Ser Leu Asp Phe Gly Leu Val Cys Arg Asn Arg Glu
3635                3640                3645

Gln Val Gly Lys Phe Lys Met Cys Phe Asn Tyr Glu Ile Arg Val
3650                3655                3660

Phe Cys Cys Asn Tyr Gly His Cys Pro Ser Thr Pro Ala Thr Ser
3665                3670                3675

Ser Thr Ala Thr Pro Ser Ser Thr Pro Gly Thr Thr Trp Ile Leu
3680                3685                3690

Thr Lys Leu Thr Thr Thr Ala Thr Thr Thr Glu Ser Thr Gly Ser
3695                3700                3705

Thr Ala Thr Pro Ser Ser Thr Pro Gly Thr Thr Trp Ile Leu Thr
3710                3715                3720

Glu Pro Ser Thr Thr Ala Thr Val Thr Val Pro Thr Gly Ser Thr
3725                3730                3735

Ala Thr Ala Ser Ser Thr Gln Ala Thr Ala Gly Thr Pro His Val
3740                3745                3750

Ser Thr Thr Ala Thr Thr Pro Thr Val Thr Ser Ser Lys Ala Thr
3755                3760                3765

Pro Phe Ser Ser Pro Gly Thr Ala Thr Ala Leu Pro Ala Leu Arg
3770                3775                3780

Ser Thr Ala Thr Thr Pro Thr Ala Thr Ser Phe Thr Ala Ile Pro
3785                3790                3795

Ser Ser Ser Leu Gly Thr Thr Trp Thr Arg Leu Ser Gln Thr Thr
3800                3805                3810

Thr Pro Thr Ala Thr Met Ser Thr Ala Thr Pro Ser Ser Thr Pro
3815                3820                3825

Glu Thr Ala His Thr Ser Thr Val Leu Thr Thr Thr Ala Thr Thr
3830                3835                3840

Thr Arg Ala Thr Gly Ser Val Ala Thr Pro Ser Ser Thr Pro Gly
3845                3850                3855

Thr Ala His Thr Thr Lys Val Pro Thr Thr Thr Thr Gly Phe
3860                3865                3870

Thr Val Thr Pro Ser Ser Ser Pro Gly Thr Ala Arg Thr Pro Pro
3875                3880                3885

Val Trp Ile Ser Thr Thr Thr Pro Thr Thr Ser Gly Ser Thr
3890                3895                3900

Val Thr Pro Ser Ser Val Pro Gly Thr Thr His Thr Pro Thr Val
3905                3910                3915

Leu Thr Thr Thr Thr Thr Val Ala Thr Gly Ser Met Ala Thr
3920                3925                3930

Pro Ser Ser Ser Thr Gln Thr Ser Gly Thr Pro Pro Ser Leu Ile
```

```
              3935                3940                3945
Thr  Thr  Ala  Thr  Thr  Ile  Thr  Ala  Thr  Gly  Ser  Thr  Thr  Asn  Pro
              3950                3955                3960
Ser  Ser  Thr  Pro  Gly  Thr  Thr  Pro  Ile  Pro  Pro  Val  Leu  Thr  Thr
              3965                3970                3975
Thr  Ala  Thr  Thr  Pro  Ala  Ala  Thr  Ser  Ser  Thr  Val  Thr  Pro  Ser
              3980                3985                3990
Ser  Ala  Leu  Gly  Thr  Thr  His  Thr  Pro  Pro  Val  Pro  Asn  Thr  Thr
              3995                4000                4005
Ala  Thr  Thr  His  Gly  Arg  Ser  Leu  Ser  Pro  Ser  Ser  Pro  His  Thr
              4010                4015                4020
Val  Arg  Thr  Ala  Trp  Thr  Ser  Ala  Thr  Ser  Gly  Thr  Leu  Gly  Thr
              4025                4030                4035
Thr  His  Ile  Thr  Glu  Pro  Ser  Thr  Gly  Thr  Ser  His  Thr  Pro  Ala
              4040                4045                4050
Ala  Thr  Thr  Gly  Thr  Thr  Gln  His  Ser  Thr  Pro  Ala  Leu  Ser  Ser
              4055                4060                4065
Pro  His  Pro  Ser  Ser  Arg  Thr  Thr  Glu  Ser  Pro  Pro  Ser  Pro  Gly
              4070                4075                4080
Thr  Thr  Thr  Pro  Gly  His  Thr  Thr  Ala  Thr  Ser  Arg  Thr  Thr  Ala
              4085                4090                4095
Thr  Ala  Thr  Pro  Ser  Lys  Thr  Arg  Thr  Ser  Thr  Leu  Leu  Pro  Ser
              4100                4105                4110
Ser  Pro  Thr  Ser  Ala  Pro  Ile  Thr  Thr  Val  Val  Thr  Thr  Gly  Cys
              4115                4120                4125
Glu  Pro  Gln  Cys  Ala  Trp  Ser  Glu  Trp  Leu  Asp  Tyr  Ser  Tyr  Pro
              4130                4135                4140
Met  Pro  Gly  Pro  Ser  Gly  Gly  Asp  Phe  Asp  Thr  Tyr  Ser  Asn  Ile
              4145                4150                4155
Arg  Ala  Ala  Gly  Gly  Ala  Val  Cys  Glu  Gln  Pro  Leu  Gly  Leu  Glu
              4160                4165                4170
Cys  Arg  Ala  Gln  Ala  Gln  Pro  Gly  Val  Pro  Leu  Gly  Glu  Leu  Gly
              4175                4180                4185
Gln  Val  Val  Glu  Cys  Ser  Leu  Asp  Phe  Gly  Leu  Val  Cys  Arg  Asn
              4190                4195                4200
Arg  Glu  Gln  Val  Gly  Lys  Phe  Lys  Met  Cys  Phe  Asn  Tyr  Glu  Ile
              4205                4210                4215
Arg  Val  Phe  Cys  Cys  Asn  Tyr  Gly  His  Cys  Pro  Ser  Thr  Pro  Ala
              4220                4225                4230
Thr  Ser  Ser  Thr  Ala  Met  Pro  Ser  Ser  Thr  Pro  Gly  Thr  Thr  Trp
              4235                4240                4245
Ile  Leu  Thr  Glu  Leu  Thr  Thr  Thr  Ala  Thr  Thr  Thr  Ala  Ser  Thr
              4250                4255                4260
Gly  Ser  Thr  Ala  Thr  Pro  Ser  Ser  Thr  Pro  Gly  Thr  Ala  Pro  Pro
              4265                4270                4275
Pro  Lys  Val  Leu  Thr  Ser  Pro  Ala  Thr  Thr  Pro  Thr  Ala  Thr  Ser
              4280                4285                4290
Ser  Lys  Ala  Thr  Ser  Ser  Ser  Pro  Arg  Thr  Ala  Thr  Thr  Leu
              4295                4300                4305
Pro  Val  Leu  Thr  Ser  Thr  Ala  Thr  Lys  Ser  Thr  Ala  Thr  Ser  Val
              4310                4315                4320
Thr  Pro  Ile  Pro  Ser  Ser  Thr  Leu  Gly  Thr  Thr  Gly  Thr  Leu  Pro
              4325                4330                4335
```

-continued

```
Glu Gln Thr Thr Thr Pro Val Ala Thr Met Ser Thr Ile His Pro
    4340                4345                4350

Ser Ser Thr Pro Glu Thr Thr His Thr Ser Thr Val Leu Thr Thr
    4355                4360                4365

Lys Ala Thr Thr Thr Arg Ala Thr Ser Ser Thr Ser Thr Pro Ser
    4370                4375                4380

Ser Thr Pro Gly Thr Thr Trp Ile Leu Thr Glu Leu Thr Thr Ala
    4385                4390                4395

Ala Thr Thr Thr Ala Ala Thr Gly Pro Thr Ala Thr Pro Ser Ser
    4400                4405                4410

Thr Pro Gly Thr Thr Trp Ile Leu Thr Glu Leu Thr Thr Thr Ala
    4415                4420                4425

Thr Thr Thr Ala Ser Thr Gly Ser Thr Ala Thr Pro Ser Ser Thr
    4430                4435                4440

Pro Gly Thr Thr Trp Ile Leu Thr Glu Pro Ser Thr Thr Ala Thr
    4445                4450                4455

Val Thr Val Pro Thr Gly Ser Thr Ala Thr Ala Ser Ser Thr Gln
    4460                4465                4470

Ala Thr Ala Gly Thr Pro His Val Ser Thr Thr Ala Thr Thr Pro
    4475                4480                4485

Thr Val Thr Ser Ser Lys Ala Thr Pro Ser Ser Ser Pro Gly Thr
    4490                4495                4500

Ala Thr Ala Leu Pro Ala Leu Arg Ser Thr Ala Thr Thr Pro Thr
    4505                4510                4515

Ala Thr Ser Phe Thr Ala Ile Pro Ser Ser Ser Leu Gly Thr Thr
    4520                4525                4530

Trp Thr Arg Leu Ser Gln Thr Thr Thr Pro Thr Ala Thr Met Ser
    4535                4540                4545

Thr Ala Thr Pro Ser Ser Thr Pro Glu Thr Val His Thr Ser Thr
    4550                4555                4560

Val Leu Thr Ala Thr Ala Thr Thr Thr Gly Ala Thr Gly Ser Val
    4565                4570                4575

Ala Thr Pro Ser Ser Thr Pro Gly Thr Ala His Thr Thr Lys Val
    4580                4585                4590

Pro Thr Thr Thr Thr Gly Phe Thr Ala Thr Pro Ser Ser Ser
    4595                4600                4605

Pro Gly Thr Ala Leu Thr Pro Pro Val Trp Ile Ser Thr Thr Thr
    4610                4615                4620

Thr Pro Thr Thr Thr Thr Pro Thr Thr Ser Gly Ser Thr Val Thr
    4625                4630                4635

Pro Ser Ser Ile Pro Gly Thr Thr His Thr Ala Arg Val Leu Thr
    4640                4645                4650

Thr Thr Thr Thr Thr Val Ala Thr Gly Ser Met Ala Thr Pro Ser
    4655                4660                4665

Ser Ser Thr Gln Thr Ser Gly Thr Pro Pro Ser Leu Thr Thr Thr
    4670                4675                4680

Ala Thr Thr Ile Thr Ala Thr Gly Ser Thr Thr Asn Pro Ser Ser
    4685                4690                4695

Thr Pro Gly Thr Thr Pro Ile Thr Pro Val Leu Thr Ser Thr Ala
    4700                4705                4710

Thr Thr Pro Ala Ala Thr Ser Ser Lys Ala Thr Ser Ser Ser Ser
    4715                4720                4725
```

-continued

```
Pro Arg Thr Ala Thr Thr Leu Pro Val Leu Thr Ser Thr Ala Thr
    4730                4735                4740

Lys Ser Thr Ala Thr Ser Phe Thr Pro Ile Pro Ser Ser Thr Leu
    4745                4750                4755

Trp Thr Thr Trp Thr Val Pro Ala Gln Thr Thr Thr Pro Met Ser
    4760                4765                4770

Thr Met Ser Thr Ile His Thr Ser Ser Thr Pro Glu Thr Thr His
    4775                4780                4785

Thr Ser Thr Val Leu Thr Thr Thr Ala Thr Met Thr Arg Ala Thr
    4790                4795                4800

Asn Ser Thr Ala Thr Pro Ser Ser Thr Leu Gly Thr Thr Arg Ile
    4805                4810                4815

Leu Thr Glu Leu Thr Thr Thr Ala Thr Thr Ala Ala Thr Gly
    4820                4825                4830

Ser Thr Ala Thr Leu Ser Ser Thr Pro Gly Thr Thr Trp Ile Leu
    4835                4840                4845

Thr Glu Pro Ser Thr Ile Ala Thr Val Met Val Pro Thr Gly Ser
    4850                4855                4860

Thr Ala Thr Ala Ser Ser Thr Leu Gly Thr Ala His Thr Pro Lys
    4865                4870                4875

Val Val Thr Thr Met Ala Thr Met Pro Thr Ala Thr Ala Ser Thr
    4880                4885                4890

Val Pro Ser Ser Ser Thr Val Gly Thr Thr Arg Thr Pro Ala Val
    4895                4900                4905

Leu Pro Ser Ser Leu Pro Thr Phe Ser Val Ser Thr Val Ser Ser
    4910                4915                4920

Ser Val Leu Thr Thr Leu Arg Pro Thr Gly Phe Pro Ser Ser His
    4925                4930                4935

Phe Ser Thr Pro Cys Phe Cys Arg Ala Phe Gly Gln Phe Phe Ser
    4940                4945                4950

Pro Gly Glu Val Ile Tyr Asn Lys Thr Asp Arg Ala Gly Cys His
    4955                4960                4965

Phe Tyr Ala Val Cys Asn Gln His Cys Asp Ile Asp Arg Phe Gln
    4970                4975                4980

Gly Ala Cys Pro Thr Ser Pro Pro Val Ser Ser Ala Pro Leu
    4985                4990                4995

Ser Ser Pro Ser Pro Ala Pro Gly Cys Asp Asn Ala Ile Pro Leu
    5000                5005                5010

Arg Gln Val Asn Glu Thr Trp Thr Leu Glu Asn Cys Thr Val Ala
    5015                5020                5025

Arg Cys Val Gly Asp Asn Arg Val Val Leu Leu Asp Pro Lys Pro
    5030                5035                5040

Val Ala Asn Val Thr Cys Val Asn Lys His Leu Pro Ile Lys Val
    5045                5050                5055

Ser Asp Pro Ser Gln Pro Cys Asp Phe His Tyr Glu Cys Glu Cys
    5060                5065                5070

Ile Cys Ser Met Trp Gly Gly Ser His Tyr Ser Thr Phe Asp Gly
    5075                5080                5085

Thr Ser Tyr Thr Phe Arg Gly Asn Cys Thr Tyr Val Leu Met Arg
    5090                5095                5100

Glu Ile His Ala Arg Phe Gly Asn Leu Ser Leu Tyr Leu Asp Asn
    5105                5110                5115

His Tyr Cys Thr Ala Ser Ala Thr Ala Ala Ala Ala Arg Cys Pro
```

```
            5120                5125                5130
Arg Ala Leu Ser Ile His Tyr Lys Ser Met Asp Ile Val Leu Thr
   5135                5140                5145
Val Thr Met Val His Gly Lys Glu Gly Leu Ile Leu Phe Asp
   5150                5155                5160
Gln Ile Pro Val Ser Ser Gly Phe Ser Lys Asn Gly Val Leu Val
   5165                5170                5175
Ser Val Leu Gly Thr Thr Thr Met Arg Val Asp Ile Pro Ala Leu
   5180                5185                5190
Gly Val Ser Val Thr Phe Asn Gly Gln Val Phe Gln Ala Arg Leu
   5195                5200                5205
Pro Tyr Ser Leu Phe His Asn Asn Thr Glu Gly Gln Cys Gly Thr
   5210                5215                5220
Cys Thr Asn Asn Gln Arg Asp Asp Cys Leu Gln Arg Asp Gly Thr
   5225                5230                5235
Thr Ala Ala Ser Cys Lys Asp Met Ala Lys Thr Trp Leu Val Pro
   5240                5245                5250
Asp Ser Arg Lys Asp Gly Cys Trp Ala Pro Thr Gly Thr Pro Pro
   5255                5260                5265
Thr Ala Ser Pro Ala Ala Pro Val Ser Ser Thr Pro Thr Pro Thr
   5270                5275                5280
Pro Cys Pro Pro Gln Pro Leu Cys Asp Leu Met Leu Ser Gln Val
   5285                5290                5295
Phe Ala Glu Cys His Asn Leu Val Pro Pro Gly Pro Phe Phe Asn
   5300                5305                5310
Ala Cys Ile Ser Asp His Cys Arg Gly Arg Leu Glu Val Pro Cys
   5315                5320                5325
Gln Ser Leu Glu Ala Tyr Ala Glu Leu Cys Arg Ala Arg Gly Val
   5330                5335                5340
Cys Ser Asp Trp Arg Gly Ala Thr Gly Gly Leu Cys Asp Leu Thr
   5345                5350                5355
Cys Pro Pro Thr Lys Val Tyr Lys Pro Cys Gly Pro Ile Gln Pro
   5360                5365                5370
Ala Thr Cys Asn Ser Arg Asn Gln Ser Pro Gln Leu Glu Gly Met
   5375                5380                5385
Ala Glu Gly Cys Phe Cys Pro Glu Asp Gln Ile Leu Phe Asn Ala
   5390                5395                5400
His Met Gly Ile Cys Val Gln Ala Cys Pro Cys Val Gly Pro Asp
   5405                5410                5415
Gly Phe Pro Lys Phe Pro Gly Glu Arg Trp Val Ser Asn Cys Gln
   5420                5425                5430
Ser Cys Val Cys Asp Glu Gly Ser Val Ser Val Gln Cys Lys Pro
   5435                5440                5445
Leu Pro Cys Asp Ala Gln Gln Pro Pro Cys Asn Arg Pro
   5450                5455                5460
Gly Phe Val Thr Val Thr Arg Pro Arg Ala Glu Asn Pro Cys Cys
   5465                5470                5475
Pro Glu Thr Val Cys Val Cys Asn Thr Thr Thr Cys Pro Gln Ser
   5480                5485                5490
Leu Pro Val Cys Pro Pro Gly Gln Glu Ser Ile Cys Thr Gln Glu
   5495                5500                5505
Glu Gly Asp Cys Cys Pro Thr Phe Arg Cys Arg Pro Gln Leu Cys
   5510                5515                5520
```

```
Ser Tyr Asn Gly Thr Phe Tyr Gly Val Gly Ala Thr Phe Pro Gly
5525                5530                5535

Ala Leu Pro Cys His Met Cys Thr Cys Leu Ser Gly Asp Thr Gln
5540                5545                5550

Asp Pro Thr Val Gln Cys Gln Glu Asp Ala Cys Asn Asn Thr Thr
5555                5560                5565

Cys Pro Gln Gly Phe Glu Tyr Lys Arg Val Ala Gly Gln Cys Cys
5570                5575                5580

Gly Glu Cys Val Gln Thr Ala Cys Leu Thr Pro Asp Gly Gln Pro
5585                5590                5595

Val Gln Leu Asn Glu Thr Trp Val Asn Ser His Val Asp Asn Cys
5600                5605                5610

Thr Val Tyr Leu Cys Glu Ala Glu Gly Gly Val His Leu Leu Thr
5615                5620                5625

Pro Gln Pro Ala Ser Cys Pro Asp Val Ser Ser Cys Arg Gly Ser
5630                5635                5640

Leu Arg Lys Thr Gly Cys Cys Tyr Ser Cys Glu Glu Asp Ser Cys
5645                5650                5655

Gln Val Arg Ile Asn Thr Thr Ile Leu Trp His Gln Gly Cys Glu
5660                5665                5670

Thr Glu Val Asn Ile Thr Phe Cys Glu Gly Ser Cys Pro Gly Ala
5675                5680                5685

Ser Lys Tyr Ser Ala Glu Ala Gln Ala Met Gln His Gln Cys Thr
5690                5695                5700

Cys Cys Gln Glu Arg Arg Val His Glu Glu Thr Val Pro Leu His
5705                5710                5715

Cys Pro Asn Gly Ser Ala Ile Leu His Thr Tyr Thr His Val Asp
5720                5725                5730

Glu Cys Gly Cys Thr Pro Phe Cys Val Pro Ala Pro Met Ala Pro
5735                5740                5745

Pro His Thr Arg Gly Phe Pro Ala Gln Glu Ala Thr Ala Val
5750                5755                5760
```

HIGH MOLECULAR WEIGHT, POST-TRANSLATIONALLY MODIFIED PROTEIN BRUSHES

RELATED APPLICATION

This application claims the benefit of priority to U.S. Provisional Patent Application Ser. No. 62/161,334, filed May 14, 2015.

GOVERNMENT SUPPORT

This invention was made with Government support under Contract No. HDTRA1-13-1-0038 awarded by the Defense Threat Reduction Agency. The Government has certain rights in the invention.

SEQUENCE LISTING

The instant application contains a Sequence Listing which has been submitted electronically in ASCII format and is hereby incorporated by reference in its entirety. Said ASCII copy, created on Oct. 3, 2017, is named MTV-164_01_SL.txt and is 210,186 bytes in size.

BACKGROUND

Mucus is one of the human body's primary defenses against pathogens. Mucus is built from proteins with hydrophobic and hydrophilic domains, where the hydrophobic domains associate together to form physical gels. Size exclusion and ionic repulsion restrict most molecules such as viruses from penetrating the gel, see FIG. 1. In many cases, mucus provides a selective filter that can allows nutrients and information to pass while keeping pathogens and toxins out. Mucus can significantly decrease the bioavailability of medicinal drugs for example. Mucins are a class of glycoproteins that are categorized by their amino acid backbone composition, glycosylation pattern, and typical location within the body. Their multiple functions are shown in FIGS. 2A and 2B. Mucins, the main gel-forming constituents of the mucus, additionally demonstrate the effect of specific binding to glycosyl sequences as a mechanism to regulate the passage of pathogens. Therefore, pharmaceutical companies are very interested in testing drug candidates to determine mucus permeability. The defense industry views mucins as a possible method for combating exogenous biological threat.

However, acquiring large quantities of mucus, such as mucins, can be challenging. A common source of mucins is obtaining them by scraping pig stomachs; however, this process typically yields mucins on the order of micrograms. Further, mucins are high molecular weight polymers that range from several hundred thousand to several million Daltons. The high molecular weight and glycosylation of mucins make them very challenging to synthesize via molecular biology. In nature, mucins are synthesized as a lightly glycosylated, thiol-reduction-resistant precursor in the golgi apparatus. This precursor is subsequently glycosylated in the endoplasmic reticulum and golgi apparatus and then further modified after secretion outside of the cell. Known mucin mimics are typically synthesized either as short glycosylated oligomers that are polymerized resulting in low-molecular weight mimics or expressed as proteins that are glycosylated with expensive enzymes resulting in a low degree of glycosylation.

Provided herein is a series of brush proteins that mimics the variable number of tandem repeats (VNTR) of respiratory mucins that have the capability to be chain-extended through disulfide coupling and the use of a bioconjugation technique to post-translationally mass functionalize proteins. In nature, enzymes functionalize threonines and serines via glycosylation. As reproducing this process in vitro is both expensive and challenging, we used diazonium coupling based tyrosine modification chemistry that is orthogonal to cysteine based chain extension functionalization. Diazonium coupling is typically used to bioconjugate proteins on a single location. Here, we describe the use of this chemistry to mass functionalize a protein. This method of economically mimicking post-translational modification enables the production of high molecular weight and densely functionalized mucin mimetic materials.

There exists a need for mimics of mucins that retain their physical and functional characteristics. The proteins described herein provide a series of mucin mimics that are useful in developing and testing, for example, pharmaceutical drug metabolic properties.

SUMMARY

Disclosed herein are polypeptides comprising a plurality of tandem repeats of a sequence comprised by a mucin selected from the group consisting of MUC1 (SEQ ID NO: 12), MUC2 (SEQ ID NO: 13), MUC4 (SEQ ID NO: 14), MUC7 (SEQ ID NO: 15), MUC5AC (SEQ ID NO: 16) and MUC5B (SEQ ID NO: 17), wherein about 20% to about 50% of the serine and threonine amino acids in the tandem repeats have been replaced by tyrosine residues. In one embodiment, the mucin is MUC5AC (SEQ ID NO: 16) or MUC5B (SEQ ID NO: 17). In another embodiment, about 33% to about 50% of the serine and threonine amino acids have been replaced by tyrosine residues. In some embodiments, the N-terminal and C-terminal amino acids are cysteine.

The polypeptide can be selected from the group consisting of MUC5ACL (SEQ ID NO: 2), MUC5ACH (SEQ ID NO: 3), MUC5BL (SEQ ID NO: 4), MUC5BH (SEQ ID NO: 5), MUC5ACL-S(SEQ ID NO: 6), MUC5ACL-LT (SEQ ID NO: 7), MUC5ACL+D (SEQ ID NO: 8), MUC5ACLS-15 (SEQ ID NO: 6), pCoil-MUC5ACL-S(SEQ ID NO: 6), pCoil-MUC5ACL-LT (SEQ ID NO: 7), pCoil-MUC5ACL+D (SEQ ID NO: 8), MUC5ACL-S-Cold (SEQ ID NO: 6), GST-MUC5ACL-S(SEQ ID NO: 6), MBP-MUC5ACL-S(SEQ ID NO: 6), ELP 1:1 Y:S 10k (SEQ ID NO: 9), ELP 3:1 Y:S 10k (SEQ ID NO: 10), and MUC5ACLSS (SEQ ID NO: 11). In some embodiments, the polypeptide is selected from the group consisting of MUC5ACL (SEQ ID NO: 2), MUC5ACH (SEQ ID NO: 3), MUC5BL (SEQ ID NO: 4), MUC5BH (SEQ ID NO: 5), MUC5ACL-S(SEQ ID NO: 6), MUC5ACL-LT (SEQ ID NO: 7), and MUC5ACL+D (SEQ ID NO: 8). In some embodiments, the polypeptide is selected from the group consisting of MUC5ACLS-15 (SEQ ID NO: 6), pCoil-MUC5ACL-S(SEQ ID NO: 6), pCoil-MUC5ACL-LT (SEQ ID NO: 7), and pCoil-MUC5ACL+D (SEQ ID NO: 8). In some embodiments, the polypeptide is selected from the group consisting of MUC5ACL-S-Cold (SEQ ID NO: 6), GST-MUC5ACL-S(SEQ ID NO: 6), and MBP-MUC5ACL-S(SEQ ID NO: 6). In some embodiments, the polypeptide is selected from the group consisting of ELP 1:1 Y:S 10k (SEQ ID NO: 9), ELP 3:1 Y:S 10k (SEQ ID NO: 10), and MUC5ACLSS (SEQ ID NO: 11). In one embodiment, the polypeptide is MUC5ACL (SEQ ID NO: 2).

In some embodiments, the number of tandem repeat sequences ranges from about 15 to about 70. The length of the repeat sequence can range from about 700 Da to about 2 kDa. In some embodiments, a plurality of the tyrosine residues have been modified to include a substituent selected from the group consisting of alkyl, alkynyl, aryl, amino, carboxyl, heteroaryl, nitro, sulfate, and polyethylene oxide polymer. In one embodiment, the plurality is at least 20% of the tyrosine residues. In another embodiment, the plurality is at least 50% of the tyrosine residues. Also provided are pharmaceutical compositions comprising a polypeptide as described herein and a pharmaceutically acceptable carrier.

Disclosed herein are protein oligomers comprising at least two polypeptide units, wherein the polypeptide units comprise a plurality of tandem repeats of a sequence comprised by a mucin selected from the group consisting of MUC1 (SEQ ID NO: 12), MUC2 (SEQ ID NO: 13), MUC4 (SEQ ID NO: 14), MUC7 (SEQ ID NO: 15), MUC5AC (SEQ ID NO: 16) and MUC5B (SEQ ID NO: 17); and about 20% to about 50% of the serine and threonine amino acids in the protein oligomer have been replaced by tyrosine residues. All of the polypeptide embodiments disclosed above also describe the polypeptide units in the protein oligomers. Also provided are pharmaceutical compositions comprising a protein oligomer as described herein and a pharmaceutically acceptable carrier.

Disclosed herein are processes for preparing a polypeptide comprising a plurality of tandem repeats of a sequence comprised by a mucin selected from the group consisting of MUC1 (SEQ ID NO: 12), MUC2 (SEQ ID NO: 13), MUC4 (SEQ ID NO: 14), MUC7 (SEQ ID NO: 15), MUC5AC (SEQ ID NO: 16) and MUC5B (SEQ ID NO: 17), wherein about 20% to about 50% of the serine and threonine amino acids in the tandem repeats have been replaced by tyrosine residues, comprising a. expressing the polypeptide through use of a plasmid in a host cell; and b. isolating the polypeptide from the cell.

All of the polypeptide embodiments disclosed above also describe the polypeptide prepared by this process.

Disclosed herein are processes for preparing a polypeptide comprising a plurality of tandem repeats of a sequence comprised by a mucin selected from the group consisting of MUC1 (SEQ ID NO: 12), MUC2 (SEQ ID NO: 13), MUC4 (SEQ ID NO: 14), MUC7 (SEQ ID NO: 15), MUC5AC (SEQ ID NO: 16) and MUC5B (SEQ ID NO: 17), wherein about 20% to about 50% of the serine and threonine amino acids in the tandem repeats have been replaced by tyrosine residues, comprising modifying a plurality of the tyrosine residues by

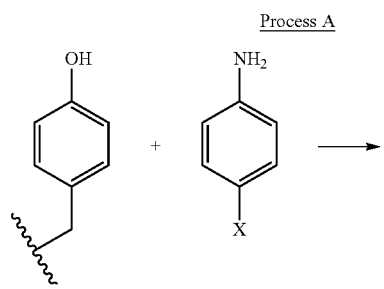

Process A

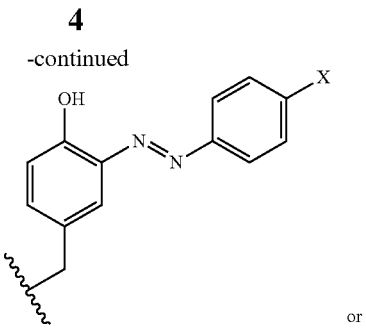

or

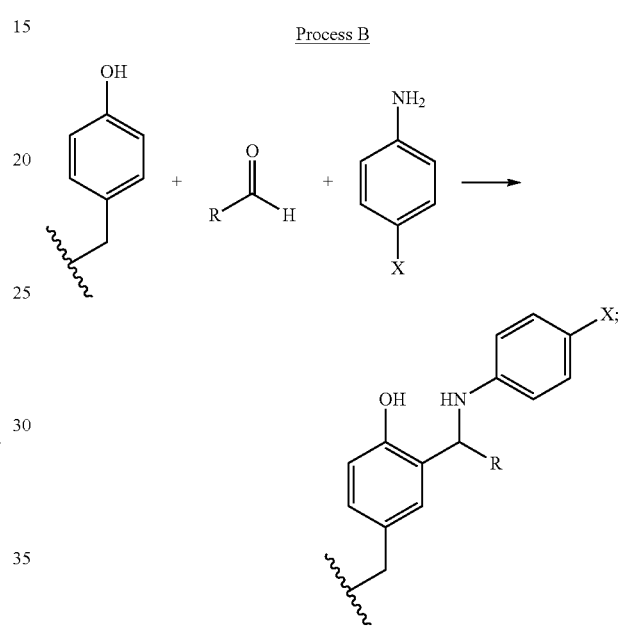

Process B wherein X is selected from the group consisting of alkyl, alkynyl, aryl, amino, carboxyl, heteroaryl, nitro, sulfate, and polyethylene oxide polymer; and
R is selected from the group consisting of H or alkyl;
or a pharmaceutically acceptable salt thereof.

In one embodiment, the mucin is MUC5AC (SEQ ID NO: 16) or MUC5B (SEQ ID NO: 17). In another embodiment, X is selected from the group consisting of ethynyl, phenyl, carboxyl, triazolyl, nitro, sulfate and polyethylene oxide. In some embodiments, X is triazolyl, and the triazolyl is linked to a galactosyl group via a polyol linker. In other embodiments, X is phenyl, and the phenyl is substituted with an amido group. In some embodiments, R is H. In some embodiments, the plurality is at least 20% of the tyrosine residues, while in other embodiments, the plurality is at least 50% of the tyrosine residues.

Disclosed herein are processes for preparing a protein oligomer comprising at least two polypeptide units, wherein the polypeptide units comprise a plurality of tandem repeats of a sequence comprised by a mucin selected from the group consisting of MUC1 (SEQ ID NO: 12), MUC2 (SEQ ID NO: 13), MUC4 (SEQ ID NO: 14), MUC7 (SEQ ID NO: 15), MUC5AC (SEQ ID NO: 16) and MUC5B (SEQ ID NO: 17); and about 20% to about 50% of the serine and threonine amino acids in the protein oligomer have been replaced by tyrosine residues, comprising linking at least two polypeptide units together through a disulfide bond between the N-terminus of one protein and the C-terminus of the other protein.

All of the polypeptide embodiments disclosed above also describe the polypeptide units used in this process for preparing a protein oligomer.

Disclosed herein are processes for a protein oligomer comprising at least two polypeptide units, wherein the polypeptide units comprise a plurality of tandem repeats of a sequence comprised by a mucin selected from the group consisting of MUC1 (SEQ ID NO: 12), MUC2 (SEQ ID NO: 13), MUC4 (SEQ ID NO: 14), MUC7 (SEQ ID NO: 15), MUC5AC (SEQ ID NO: 16) and MUC5B (SEQ ID NO: 17); and about 20% to about 50% of the serine and threonine amino acids in the protein oligomer have been replaced by tyrosine residues,
comprising modifying a plurality of the tyrosine residues by

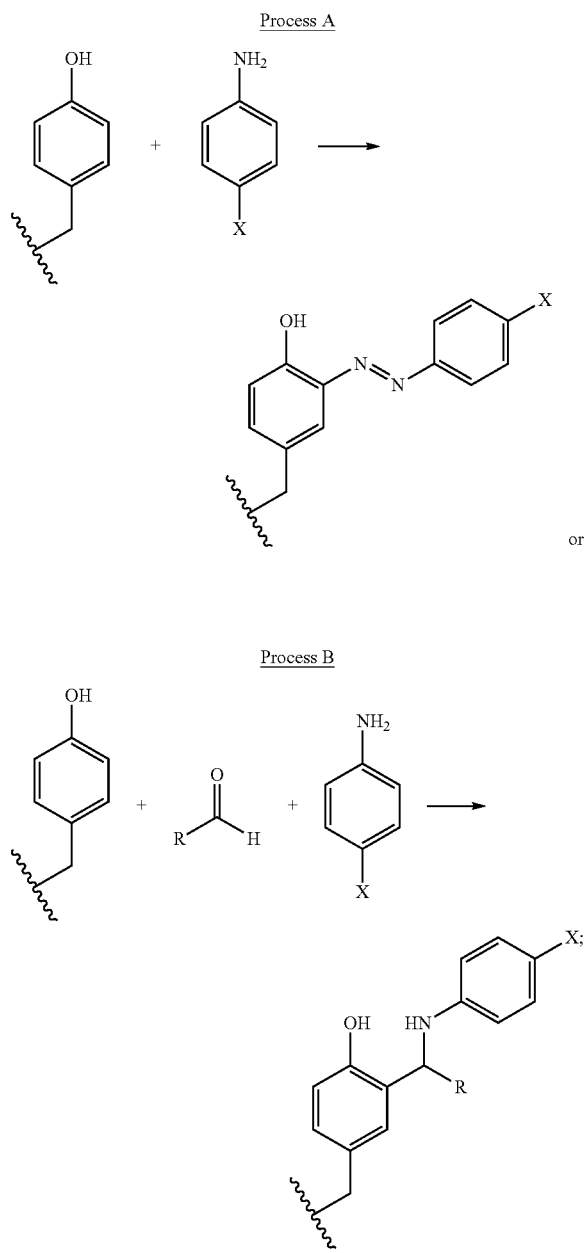

wherein X is selected from the group consisting of alkyl, alkynyl, aryl, amino, carboxyl, heteroaryl, nitro, sulfate, and polyethylene oxide polymer; and R is selected from the group consisting of H or alkyl;
or a pharmaceutically acceptable salt thereof.

All of the embodiments described above for processes for preparing a polypeptide comprising modifying a plurality of the tyrosine residues by Process A or Process B also describe the above processes for preparing a protein oligomer comprising modifying a plurality of the tyrosine residues by Process A or Process B.

BRIEF DESCRIPTION OF THE FIGURES

FIG. 1 depicts a wall of epithelial cells that are coated with mucin biopolymers. Viruses shown as stars are blocked from interaction with the epithelial cells.

FIG. 2B depicts a schematic of a cell coated with mucins that provide pathogen inhibition and clearance and lubrication. Mucin properties include their size and structure, functionality, and charge.

FIG. 3A depicts membrane-tethered mucins MUC1 (SEQ ID NO: 12) having, among other features, a section of tandem repeats.

FIG. 3B depicts secreted MUC7 (SEQ ID NO: 15) mucins that are non-cysteine rich having, among other features, as PTS-region.

FIG. 3C depicts secreted mucins MUC2 (SEQ ID NO: 13), MUC5B (SEQ ID NO: 17) and MUC5AC (SEQ ID NO: 16) that are cysteine rich having, among other features, sections of tandem repeats.

FIG. 4 depicts a number of artificially created mucin mimetic proteins having 12, 30 or 46 sequence repeats and the vectors used to express them. In order of appearance, FIG. 4 discloses SEQ ID NOS: 2-8.

FIG. 5A depicts the VNTR consensus sequence of MUC5AC (SEQ ID NO: 16) brush protein.

FIG. 5B depicts the VNTR consensus sequence of MUC5B (SEQ ID NO: 17) brush protein.

FIG. 15 depicts pcoilcoil-mini intein proteins with their sequences and vectors used to express them in E. coli. In order of appearance, FIG. 15 discloses SEQ ID NOS: 6, 6, 7, and 8.

FIG. 20 depicts an SDS-PAGE image (top) and Western Blot (bottom) of purified GST-MUC5ACL-S(SEQ ID NO: 6)

FIG. 22 depicts the sequences of the ELP 1:1 Y:S 10k (SEQ ID NO: 9), ELP 3:1 Y:S 10k (SEQ ID NO: 10), and MUC5ACLSS (SEQ ID NO: 11) proteins and vectors used to express them in E. coli. In order of appearance, FIG. 22 discloses SEQ ID NOS: 9-11.

DETAILED DESCRIPTION

Definitions

Figure 2A:
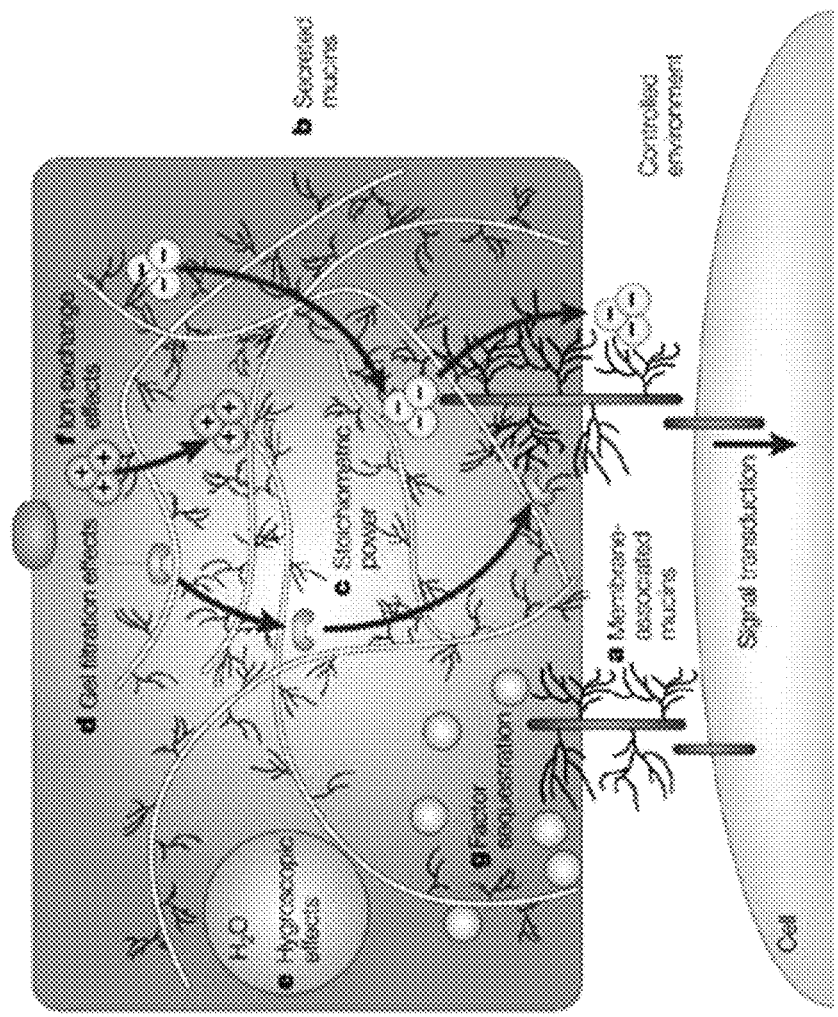
FIG. 2A depicts a cell with secreted mucins above it. The various functions of the mucins, such as gel filtration effects and ion-exchange effects, are shown next to an image of mucin polymers.

Unless defined otherwise, all technical and scientific terms used herein have the meaning commonly understood by a person skilled in the art of the present disclosure. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments. Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used herein, the term "alkyl", by itself or as part of another substituent means, unless otherwise stated, a branched or unbranched saturated hydrocarbon group. The term "n-alkyl" refers to an unbranched alkyl group. The term "$C_x$-$C_y$ alkyl" refers to an alkyl group having between x and y carbon atoms, inclusively, in the branched or unbranched hydrocarbon group. By way of illustration, but without limitation, the term "$C_1$-$C_8$ alkyl" refers to a straight chain or branched hydrocarbon moiety having from 1, 2, 3, 4, 5, 6, 7, or 8 carbon atoms. "$C_1$-$C_6$" refers to a straight chain or branched hydrocarbon moiety having from 1, 2, 3, 4, 5, or 6 carbon atoms. "$C_1$-$C_4$ alkyl" refers to a straight chain or branched hydrocarbon moiety having from 1, 2, 3, or 4 carbon atoms, including methyl, ethyl, n-propyl, iso-propyl, n-butyl, iso-butyl, sec-butyl, and tert-butyl. The term "$C_1$-$C_4$ n-alkyl" refers to straight chain hydrocarbon moieties that have 1, 2, 3, or 4 carbon atoms including methyl, ethyl, n-propyl, and n-butyl.

As used herein, the term "alkenyl" by itself or as part of another substituent means, unless otherwise stated, a straight or branched hydrocarbon chain radical group consisting solely of carbon and hydrogen atoms, containing at least one double bond, and having from two to ten carbon atoms (i.e., $C_{2-10}$ alkenyl). Whenever it appears herein, a numerical range such as "2 to 10" refers to each integer in the given range; e.g., "2 to 10 carbon atoms" means that the alkenyl group can consist of 2 carbon atoms, 3 carbon atoms, etc., up to and including 10 carbon atoms. In certain embodiments, an alkenyl comprises two to eight carbon atoms. In other embodiments, an alkenyl comprises two to six carbon atoms (e.g., $C_{2-6}$ alkenyl). The alkenyl is attached to the parent molecular structure by a single bond, for example, ethenyl (i.e., vinyl), prop-1-enyl (i.e., allyl), but-1-enyl, pent-1-enyl, penta-1,4-dienyl, and the like. The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), 2-methyl-prop-2-enyl ($C_4$), butadienyl ($C_4$) and the like. Examples of $C_{2-6}$ alkenyl groups include the aforementioned $C_{2-4}$ alkenyl groups as well as pentenyl ($C_5$), pentadienyl ($C_5$), hexenyl ($C_6$), 2,3-dimethyl-2-butenyl ($C_6$) and the like, and the higher homologs and isomers. A non-limiting functional group representing an alkene is exemplified by —$CH_2$—CH=$CH_2$.

As used herein, the term "alkynyl" employed alone or in combination with other terms means, unless otherwise stated, a stable straight chain or branched chain hydrocarbon group with a triple carbon-carbon bond, having the stated number of carbon atoms (i.e., $C_2$-$C_{10}$ means two to ten carbon atoms, $C_2$-$C_6$ means two to six carbon atoms). Non-limiting examples include ethynyl and propynyl, and the higher homologs and isomers. The term "propargylic" refers to a group exemplified by —$CH_2$—C≡CH. The term "homopropargylic" refers to a group exemplified by —$CH_2CH_2$—C≡CH. The term "substituted propargylic" refers to a group exemplified by —$CR_2$—C≡CR, wherein each occurrence of R is independently H, alkyl, substituted alkyl, alkenyl or substituted alkenyl, with the proviso that at least one R group is not hydrogen. The term "substituted homopropargylic" refers to a group exemplified by —$CR_2CR_2$—C≡CR, wherein each occurrence of R is independently H, alkyl, substituted alkyl, alkenyl or substituted alkenyl, with the proviso that at least one R group is not hydrogen.

As used herein, the term "amino acid" refers to a molecule $H_2N$—CHR—COOH, where R is known as the side-chain and can be selected from hydrogen, unsubstituted alkyl or alkyl substituted with alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, and urea. In some embodiments, the amino acid is a naturally occurring proteogenic amino acid in the L- or S-configuration (with the exception of cysteine which is R). These amino acids are as follows with the full name, abbreviation and letter code:

alanine—ala—A, arginine—arg—R, asparagine—asn—N, aspartic acid—asp—D, cysteine—cys—C, glutamine—gln—Q, glutamic acid—glu—E, glycine—gly—G, histidine—his—H, isoleucine—ile—I, leucine—leu—L, lysine—lys—K, methionine—met—M, phenylalanine—phe—F, proline—pro—P, serine—ser—S, threonine—thr—T, tryptophan—trp—W, tyrosine—tyr—Y, and valine—val—V.

The term "amino acid" also refers to unnatural or man-made amino acids. In some cases, the unnatural amino acid is the D- or R-configuration of a naturally occurring amino acid (with the exception of cysteine which is S). In other embodiments, the unnatural amino acid is a non-coded or non-proteogenic amino acid, such as selenocysteine, pyrrolysine, and N-formylmethionine. In other embodiments, an amino acid contains a synthetically derived side-chain optionally substituted as described above. An amino acid can be in neutral form or as a zwitterion: $H3N+$—CHR—COO—. The ratio of neutral to zwitterionic forms can be altered by changes in pH of the medium in which they are dissolved.

As used herein, the term "aryl" or "arene" employed alone or in combination with other terms means, unless otherwise stated, a radical with 6 to 14 ring atoms (e.g., C6-14 aromatic or C6-14 aryl) which has at least one ring having a conjugated pi electron system which is carbocyclic (e.g., phenyl, fluorenyl, and naphthyl). In some embodiments, the aryl is a C6-10 aryl group. Whenever it appears herein, a numerical range such as "6 to 14 aryl" refers to each integer in the given range; e.g., "6 to 14 ring atoms" means that the aryl group can consist of 6 ring atoms, 7 ring atoms, etc., up to and including 14 ring atoms. The term includes monocyclic or fused-ring polycyclic (i.e., rings which share adjacent pairs of ring atoms) groups. In a multi-ring group, only one ring is required to be aromatic, so groups such as indanyl are encompassed by the aryl definition. Non-limiting examples of aryl groups include phenyl, phenalenyl, naphthalenyl, tetrahydronaphthyl, phenanthrenyl, anthracenyl, fluorenyl, indolyl, indanyl, and the like.

"Carboxyl" refers to a —(C=O)OH radical.

"Galactose" is a monosaccharide of the formula below:

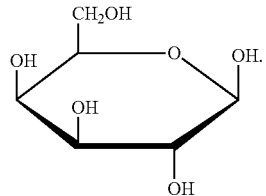

In its cyclic form, galactose can exist as a 6-membered pyranose as shown above, or as a 5-membered furanose, each having an anomer in the α or β configuration.

As used herein, the term "heterocycle", by itself or as part of another substituent means, unless otherwise stated, an unsubstituted or substituted, stable, mono- or multi-cyclic heterocyclic ring system that consists of carbon atoms and at least one heteroatom. A heterocycle refers to any 3- to 18-membered non-aromatic radical monocyclic or polycyclic moiety comprising at least one heteroatom selected from nitrogen, oxygen, phosphorous and sulfur. In some aspects, the heteroatom(s) are chosen from N, O, and S. A heterocyclyl group can be a monocyclic, bicyclic, tricyclic or tetracyclic ring system, wherein the polycyclic ring systems can be a fused, bridged or spiro ring system. Heterocyclyl polycyclic ring systems can include one or more heteroatoms in one or both rings. A heterocyclyl group can be saturated or partially unsaturated. Partially unsaturated heterocycloalkyl groups can be termed "heterocycloalkenyl" if the heterocyclyl contains at least one double bond, or "heterocycloalkynyl" if the heterocyclyl contains at least one triple bond. Whenever it appears herein, a numerical range such as "5 to 18" refers to each integer in the given range; e.g., "5 to 18 ring atoms" means that the heterocyclyl group can consist of 5 ring atoms, 6 ring atoms, etc., up to and including 18 ring atoms.

An N-containing heterocyclyl moiety refers to an nonaromatic group in which at least one of the ring atoms is a nitrogen atom. The heteroatom(s) in the heterocyclyl radical can be optionally oxidized. One or more nitrogen atoms, if present, can be optionally quaternized. Heterocyclyl also includes ring systems substituted with one or more nitrogen oxide (—O—) substituents, such as piperidinyl N-oxides. The heterocyclyl is attached to the parent molecular structure through any atom of any of the ring(s).

"Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment to the parent molecular structure is on the heterocyclyl ring. In some embodiments, a heterocyclyl group is a 5-14 membered non-aromatic ring system having ring carbon atoms and 1-4 ring heteroatoms, wherein each heteroatom is independently selected from nitrogen, oxygen, phosphorous and sulfur ("5-14 membered heterocyclyl"). In some embodiments, a heterocyclyl group is a 3-10 membered non-aromatic ring system having ring carbon atoms and 1-4 ring heteroatoms, wherein each heteroatom is independently selected from nitrogen, oxygen, phosphorous and sulfur ("3-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, phosphorous and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, phosphorous and sulfur ("5-6 membered heterocyclyl"). In some embodiments, the 5-6 membered heterocyclyl has 1-3 ring heteroatoms selected from nitrogen, oxygen phosphorous and sulfur. In some embodiments, the 5-6 membered heterocyclyl has 1-2 ring heteroatoms selected from nitrogen, oxygen, phosphorous and sulfur. In some embodiments, the 5-6 membered heterocyclyl has 1 ring heteroatom selected from nitrogen, oxygen, phosphorous and sulfur.

Exemplary 3-membered heterocyclyls containing 1 heteroatom include, without limitation, azirdinyl, oxiranyl, and thiorenyl. Exemplary 4-membered heterocyclyls containing 1 heteroatom include, without limitation, azetidinyl, oxetanyl and thietanyl. Exemplary 5-membered heterocyclyls containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyls containing 2 heteroatoms include, without limitation, dioxolanyl, oxathiolanyl, thiazolidinyl, and dithiolanyl. Exemplary 5-membered heterocyclyls containing 3 heteroatoms include, without limitation, triazolinyl, diazolonyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6 membered heterocyclyl groups containing 2 heteroatoms include, without limitation, piperazinyl, morpholinyl, thiomorpholinyl, dithianyl, dioxanyl, and triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, benzoxanyl, benzopyrrolidinyl, benzopiperidinyl, benzoxolanyl, benzothiolanyl, benzothianyl, tetrahydroindolyl, tetrahydroquinolinyl, tetrahydroisoquinolinyl, decahydroquinolinyl, decahydroisoquinolinyl, 3-1H-benzimidazol-2-one, (1-substituted)-2-oxo-benzimidazol-3-yl, octahydrochromenyl, octahydroisochromenyl, decahydronaphthyridinyl, decahydro-1,8-naphthyridinyl, octahydropyrrolo[3,2-b]pyrrole, phenanthridinyl, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo [3,2-b]pyranyl, 5,7-dihydro-4H-thieno [2,3-c]pyranyl, 2,3-dihydro-1H-pyrrolo[2,3-b]pyridinyl, hydrofuro[2,3-b]pyridinyl, 4,5,6,7 tetrahydro-1H-pyrrolo[2,3-b]pyridinyl, 4,5,6,7-tetrahydrofuro [3,2-c]pyridinyl, 4,5,6,7-tetrahydrothieno[3,2-b]pyridinyl, 1,2,3,4-tetrahydro-1,6-naphthyridinyl, and the like.

Examples of polycyclic heterocycles include indolyl (such as, but not limited to, 3-, 4-, 5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

As used herein, the term "heteroaryl" or "heteroaromatic", by itself or as part of another substituent means, unless otherwise stated, a 5-18 membered monocyclic or polycyclic (e.g., bicyclic or tricyclic) aromatic ring system (e.g., having 6, 10 or 14 π electrons shared in a cyclic array) having ring carbon atoms and 1-6 ring heteroatoms provided in the aromatic ring system, wherein each heteroatom is independently selected from nitrogen, oxygen, phosphorous and sulfur ("5-18 membered heteroaryl"). Heteroaryl polycyclic ring systems can include one or more heteroatoms in one or both rings. Whenever it appears herein, a numerical range such as "5 to 18" refers to each integer in the given range; e.g., "5 to 18 ring atoms" means that the heteroaryl group can consist of 5 ring atoms, 6 ring atoms, etc., up to and including 18 ring atoms. In some instances, a heteroaryl can have 5 to 14 ring atoms.

For example, an N-containing "heteroaryl" or "heteroaromatic" moiety refers to an aromatic group in which at least one of the skeletal atoms of the ring is a nitrogen atom. One or more heteroatom(s) in the heteroaryl radical can be optionally oxidized. One or more nitrogen atoms, if present, can also be optionally quaternized. Heteroaryl also includes ring systems substituted with one or more nitrogen oxide (—O—) substituents, such as pyridinyl N-oxides. The heteroaryl is attached to the parent molecular structure through any atom of the ring(s).

"Heteroaryl" also includes ring systems wherein the heteroaryl ring, as defined above, is fused with one or more aryl groups wherein the point of attachment to the parent molecular structure is either on the aryl or on the heteroaryl ring, or wherein the heteroaryl ring, as defined above, is fused with one or more cycloalkyl or heterocyclyl groups wherein the point of attachment to the parent molecular structure is on the heteroaryl ring. For polycyclic heteroaryl groups wherein one ring does not contain a heteroatom (e.g., indolyl, quinolinyl, carbazolyl and the like), the point of attachment to the parent molecular structure can be on either ring, i.e., either the ring bearing a heteroatom (e.g., 2-indolyl) or the ring that does not contain a heteroatom (e.g., 5-indolyl). In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, phosphorous, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, phosphorous, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, phosphorous, and sulfur ("5-6 membered heteroaryl"). In some embodiments, the 5-6 membered heteroaryl has 1-3 ring heteroatoms selected from nitrogen, oxygen, phosphorous, and sulfur. In some embodiments, the 5-6 membered heteroaryl has 1-2 ring heteroatoms selected from nitrogen, oxygen, phosphorous, and sulfur. In some embodiments, the 5-6 membered heteroaryl has 1 ring heteroatom selected from nitrogen, oxygen, phosphorous, and sulfur.

Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4] oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzopyranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno [2,3-d]pyrimidinyl, 5,6-dihydrobenzo[h]quinazolinyl, 5,6-dihydrobenzo[h]cinnolinyl, 6,7-dihydro-5H benzo[6,7]cyclohepta[1,2-c]pyridazinyl, dibenzofuranyl, dibenzothiophenyl, furanyl, furazanyl, furanonyl, furo [3,2-c]pyridinyl, 5,6,7,8,9,10-hexahydrocycloocta[d] pyrimidinyl, 5,6,7,8,9,10-hexahydrocycloocta[d]pyridazinyl, 5,6,7,8,9,10 hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d] pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo [4,5] thieno [2,3-d]pyrimidinyl, 6,7,8,9-tetrahydro-5H-cyclohepta[4,5]thieno [2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno [2,3-c]pridinyl, and thiophenyl (i.e., thienyl).

Further examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl. The aforementioned listings of heterocyclyl and heteroaryl moieties are intended to be representative and not limiting.

"Nitro" refers to the —NO$_2$ radical.

As used herein, the term "PEO2000" refers to polyethylene oxide polymer with an average weight of 2,000 kDa. PEO2000 is also known as PEG2000 (polyethylene glycol 2000).

As used herein, the term "peptide" refers to two or more amino acids that are linked together in an amide bond between the carbonyl of 1 amino acid and the amine of another amino acid: H$_2$C—(CHR)—[CONH—(CHR')]$_n$—COOH where R and R' can be individually selected from any side-chain as described above and n can range from 1 to 50, such as 3-40, such as 5-30, such as 3-20, such as 5-15, such as 3-10, and further such as 3-6. In some embodiments, a peptide can vary in length between 2 and 100 amino acid monomers or 2 to 200 amino acid monomers. A peptide can also be described by its average molecular weight, such as ranging from about 500 Da to about 10 kDa, such as about 700 Da to about 7 kDa, such as about 700 Da to about 2 kDa, such as about 1 kDa to about 10 kDa, such as about 2 kDa to about 7 kDa, further such as about 5 kDa to about 10 kDa.

In some cases, an amino acid side-chain can be referred to as a "residue". In some embodiments, the peptide is unbranched, while in others, an R or R' group contains a side-chain that is a peptide itself giving rise to a branched peptide. A peptide can be in neutral form, zwitterionic form, or positively or negatively charged form. Peptides are referred to by the number of amino acids they contain, such as dipeptide, tripeptide, tetrapeptide, etc. These smaller length peptides are known as oligopeptides. In some instances, eptides having more than about 100 amino acids are termed polypeptides. They can be endogenously created within an organism or synthetically made ex vivo using amide bond forming reactions. In some embodiments, an amino acid side-chain can be chemically modified after incorporation into a peptide. Peptides have a wide variety of applications in biological and chemical fields that are described, for example, in Kastin, A. Ed. Handbook of Biologically Active Peptides, 2$^{nd}$ Ed. Academic Press 2013; and Jakubke, H.-D. et al. Peptides from A to Z: A Concise Encyclopedia, 1$^{st}$ Ed. Wiley 2008.

As used herein, the term "protein" refers to a peptide H$_2$C—(CHR)—[CONH—(CHR')]$_n$—COOH where n is greater than 50, such as greater than 1000, such as greater than 200, such as greater than 500 and higher. Some proteins can contain over 1000 amino acids. A protein can contain any of the amino acids described above or have sections that correspond to peptides as described above. A peptide can also be described by its average molecular weight, such as ranging from about 10 kDa to about 100 kDa, such as about 20 kDa to about 80 kDa, such as about 10 kDa to about 50 kDa, such as 30 kDa to about 50 kDa.

Some proteins contain sections of repeating sequences, usually at least 5-10 residues, while others do not repeat such sections. Proteins can be synthesized as described for peptides or through linking two or more peptides together. Proteins have a wide variety of functions in vivo and ex vivo that are described, for example, in Whitford, Proteins: Structure and Function 1$^{st}$ Ed. Wiley 2005 and Buxbaum, Fundamentals of Protein Structure and Function, 2$^{nd}$ Ed. Springer 2015.

The terms "substituted" or "substitution" mean that at least one hydrogen present on a group atom (e.g., a carbon or nitrogen atom) is replaced with a permissible substituent, e.g., a substituent which upon substitution for the hydrogen results in a stable compound, e.g., a compound which does not spontaneously undergo transformation such as by rearrangement, cyclization, elimination, or other reaction. Unless otherwise indicated, a "substituted" group can have a substituent at one or more substitutable positions of the group, and when more than one position in any given structure is substituted, the substituent is either the same or different at each position. Exemplary substituents include, but are not limited to, acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, and urea.

"Sulfanyl", "sulfide", and "thio" each refer to the radical —S—R$^b$, wherein R$^b$ is selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. For instance, an "alkylthio" refers to the "alkyl-S-" radical, and "arylthio" refers to the "aryl-S-" radical, each of which are bound to the parent molecular group through the S atom. The terms "sulfide", "thiol", "mercapto", and "mercaptan" can also each refer to the group —R$^b$SH. The term "disulfide" refers to an —S—S— single bond between two sulfur atoms.

As used herein, the term "sulfonate" refers to a —S(=O)$_2$—OR$^b$ radical, wherein R$^b$ is selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Overview

Figure 2C:
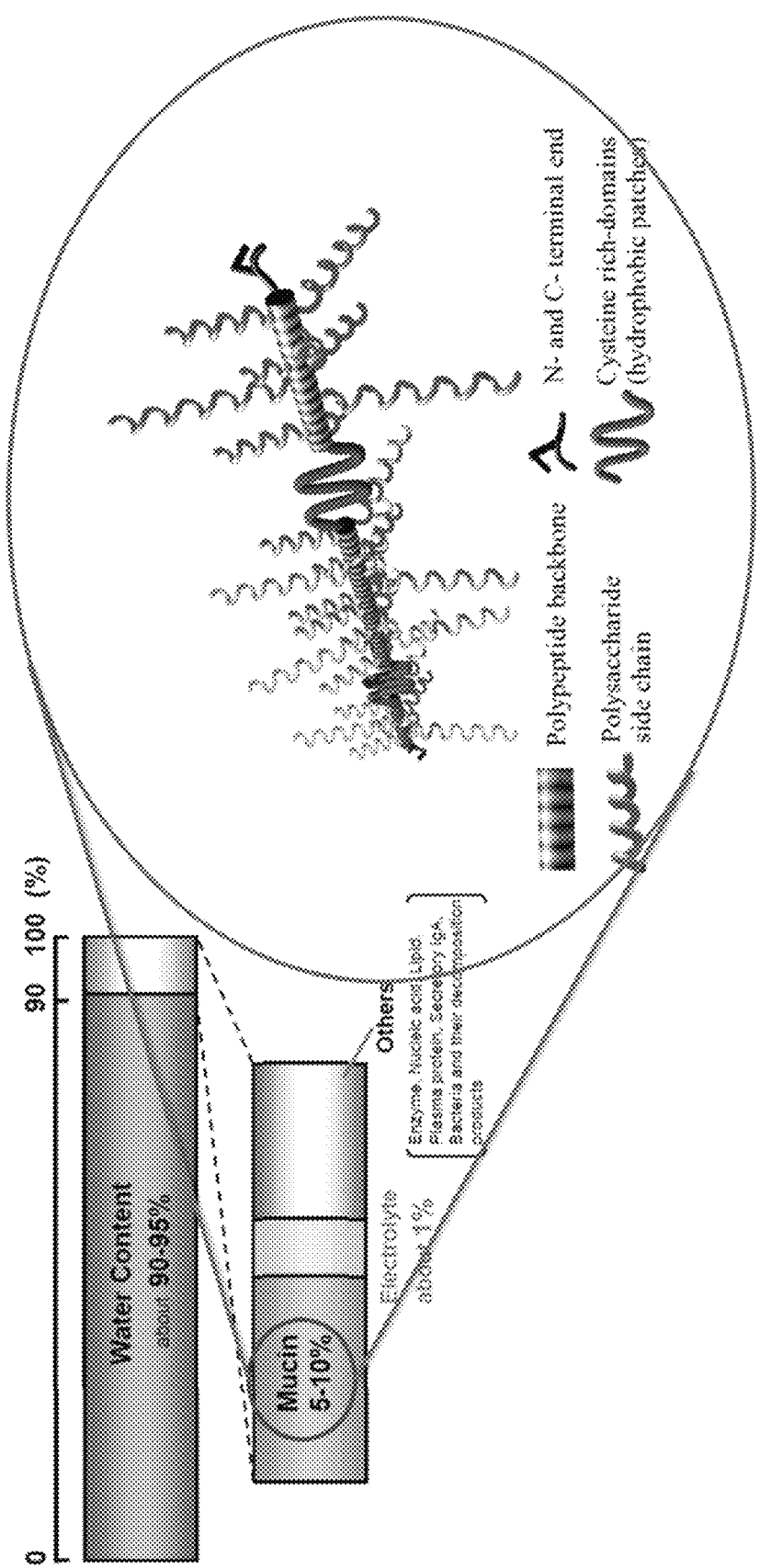
FIG. 2C depicts the 10% of bodily fluids that are not water. Of this 10%, 5-10% are mucin proteins, whose structure includes a polypeptide backbone with cysteine-rich domains and polysaccharide side chains.
Figure 2D:
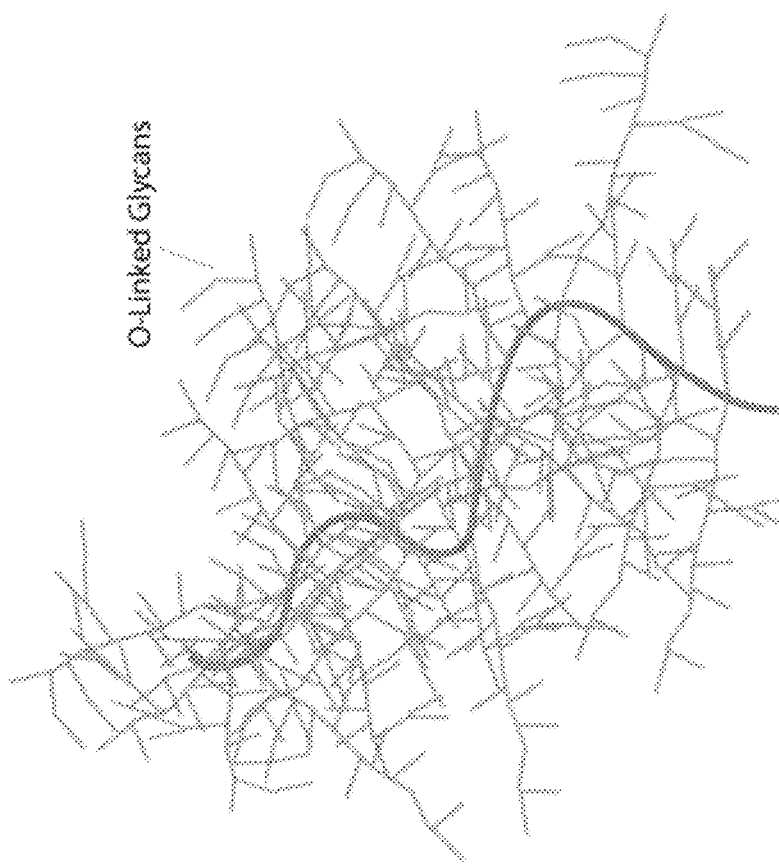
FIG. 2D depicts a mucin backbone having O-linked glycans to serine and threonine residues.

Provided herein are high molecular weight, post-translationally modified protein brushes that mimic the structure and function of mucin. Mucins are a class of glycoproteins that are categorized by their amino acid backbone composition, glycosylation pattern, and typical location within the body. Mucins compose about 0.5 to 1% of the non-water component of bodily tissues as shown in FIG. 2C. Their peptide backbone contains cysteine-rich hydrophobic sections. The glycosylation occurs post-translationally at serine and threonine residues through specific enzymatic processes to form O-linked glycans as shown in FIG. 2D. Mucins are high molecular weight polymers that range from several hundred thousand to several million daltons, and have a variable number of tandem repeat (VNTR) sequences as shown in FIGS. 3A-3C. The present protein brushes include VNTRs and are synthesized by first expressing proteins in vectors that range, for example, from about 30 kDa to about 50 kDa. Use of E. coli expression systems have provided high yields of the protein backbone. These proteins can have about 10 to about 50 sequence repeats, such as about 12 to about 46, further such as about 15 to about 30 sequence repeats. Proteins have been synthesized with 12, 30 or 46 sequence repeats as shown in FIG. 4. The VNTR consensus sequence of MUC5AC (SEQ ID NO: 16) brush protein is shown in FIG. 5A, while that of MUC5B (SEQ ID NO: 17) brush protein is shown in FIG. 5B.

Figure 6A:
FIG. 6A depicts the formation of a oligopeptide from peptide monomers.
Figure 6B:
FIG. 6B depicts that the peptide monomer having cysteine residues at the N- and C-terminal amino acids are joined to form the oligopeptide using disulfide bonds.

To reach the lengths of mucin, the proteins have terminal cysteine residues that are reacted to form disulfide bonds, shown in FIG. 6A as monomers synthesized into proteins and in FIG. 6B as disulfide-bonded oligomers. For example, oligomers of about 2 to about 30 protein units can be prepared to give protein brush backbones of about 150 kDa to about 1500 kDa. The process of disulfide bond formation can be extended to reach even higher weight protein oligomers.

Figure 7:
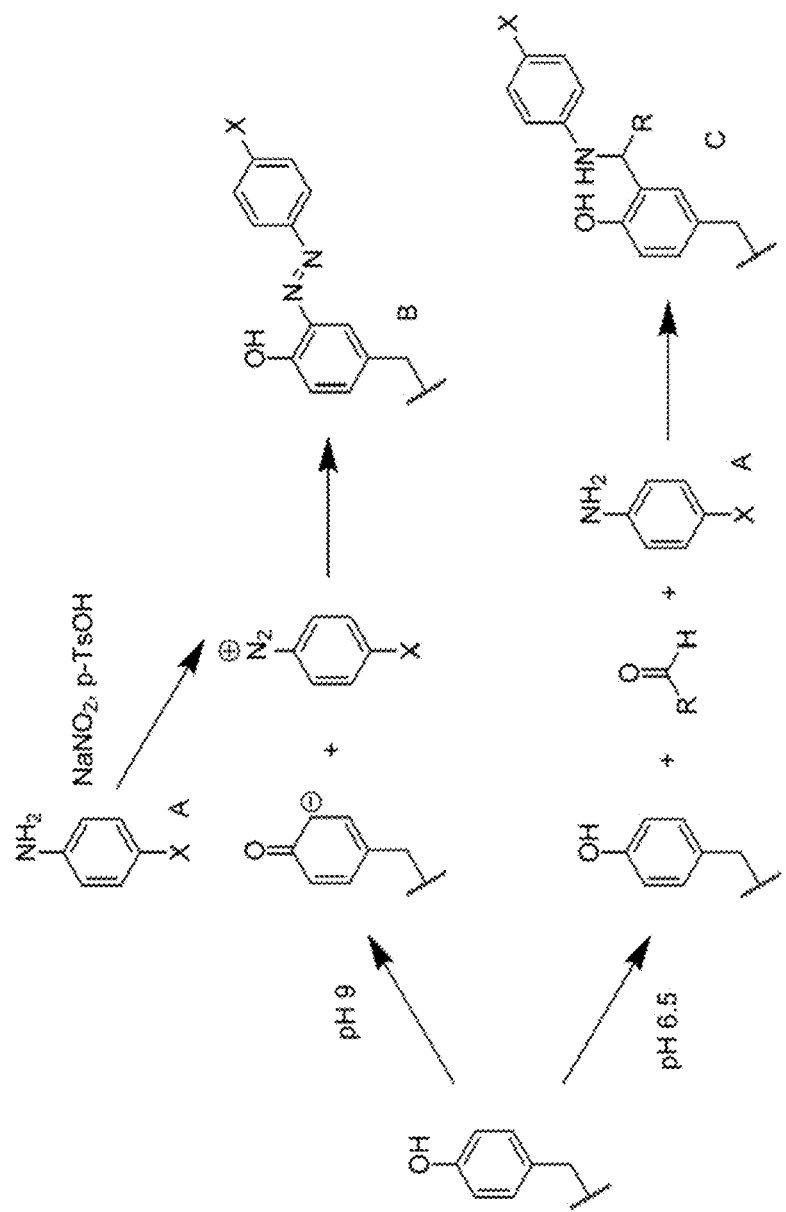
FIG. 7 depicts functionalization of tyrosine residues with ortho-diazonium linkers using a coupling procedure or with ortho methylene-amino linkers using a Mannich coupling procedure.
Figure 8:
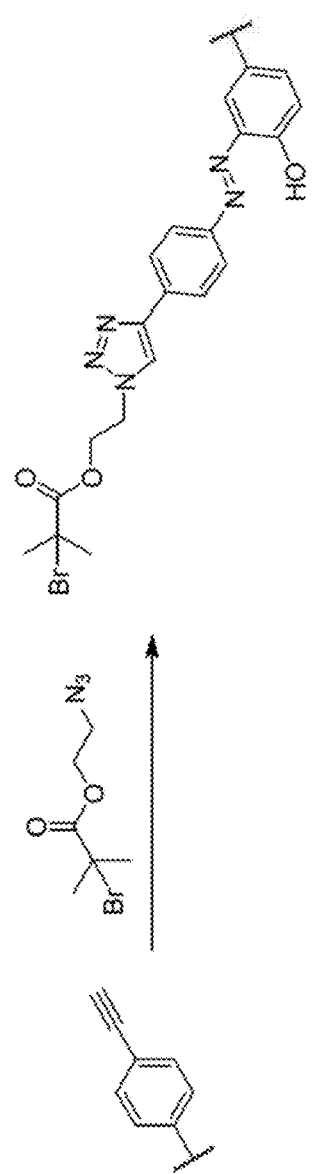
FIG. 8 depicts further functionalization of the protein backbone of FIG. 5, when X is alkyne. Click chemistry can react an azide-substituted glycosylated polymer with the alkyne to give a triazole linker. In this case, the product is suitable for atom transfer radical polymerization (ATRP) reaction
Figure 9:
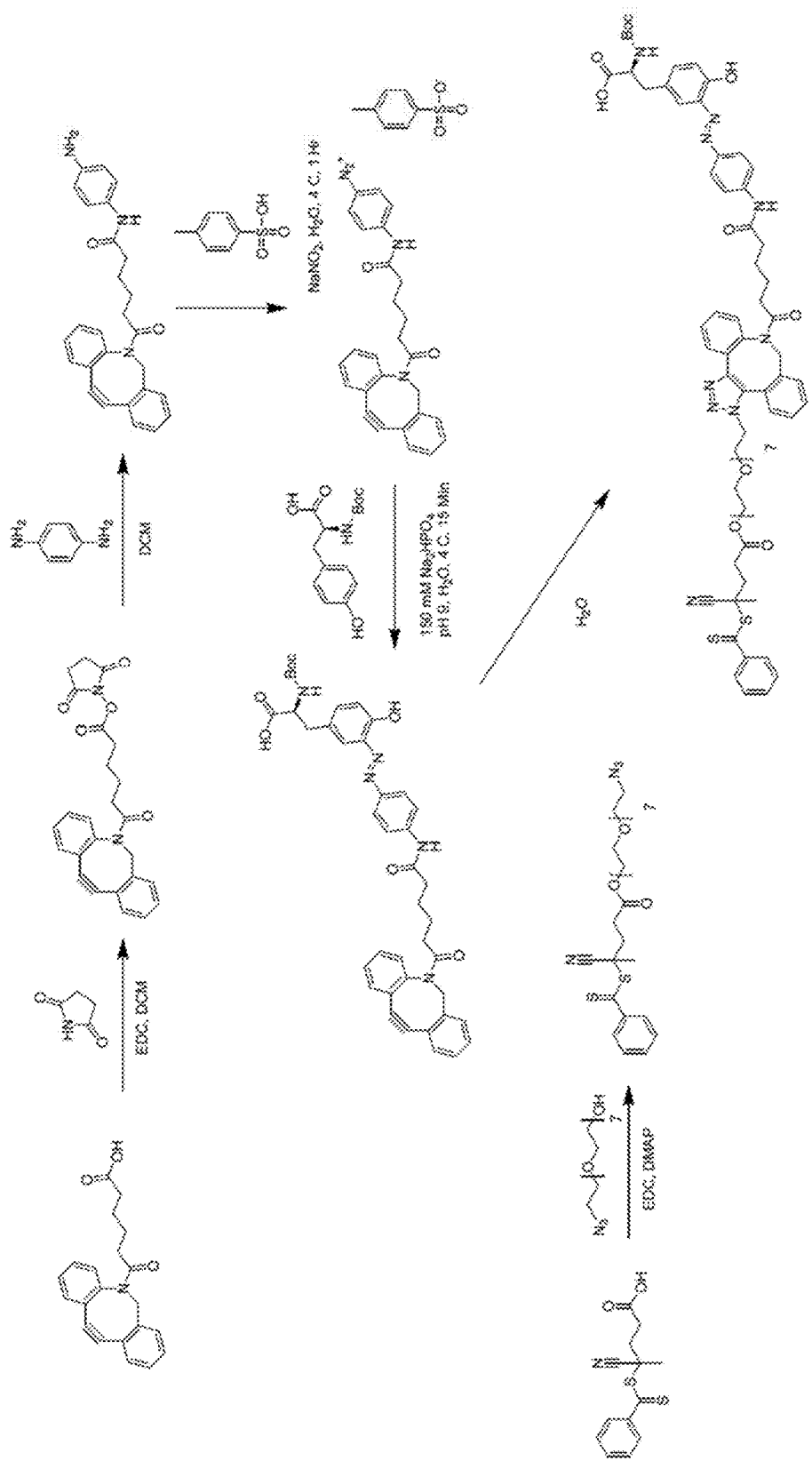
FIG. 9 depicts functionalization of tyrosine residues with a dibenzocyclooctyl reversible addition fragmentation chain transfer (DBCO/RAFT) group using a click chemistry triazole linker.

The disclosed protein brushes are based on artificially engineered respiratory mucin mimetics, where about 25% to about 50%, such as about 33% to about 50%, of their serine and thereonie residues have been replaced by tyrosine residues. Mucin is about 25% glycosylated so adding this level of tyrosine substitution allows for close resemblance to the natural level of functionalization. The tyrosine 4-hydroxybenzyl side chain enables mass modification of the protein backbone to create the brush-like feature around the core protein backbone. Thus, the natural process of mucin glycosylation is replaced by post-translational use of several synthetic reactions to form the disclosed protein brushes. One transformation occurs using diazonium coupling of substituents to the tyrosine residues, as shown in FIG. 7. Atom transfer radical polymerization (ATRP) reactions as shown in FIG. 8 can also yield diazonium coupled polymer precursors for further derivatization. A dibenzocyclooctyl reversible addition fragmentation chain transfer (DBCO/RAFT) reaction as shown in FIG. 9 can attach heterocyclyl groups that are further modified with polymeric substituents. A ring opening metathesis polymerization (ROMP) grafting-through method can attach different polymer substituents to the protein backbone. Such polymerization reactions can integrate random and block copolymers to the mucin backbone. Mannich reactions can install amine groups on the tyrosine phenyl group as shown in FIG. 7. One of ordinary skill would readily recognize that reactions known in the art that functionalize hydroxy-substituted phenyl rings can be used to install functionality to the protein brush backbone.

Disclosed herein are polypeptides comprising a plurality of tandem repeats of a sequence comprised by a mucin selected from the group consisting of MUC1 (SEQ ID NO: 12), MUC2 (SEQ ID NO: 13), MUC4 (SEQ ID NO: 14), MUC7 (SEQ ID NO: 15), MUC5AC (SEQ ID NO: 16) and MUC5B (SEQ ID NO: 17), wherein about 20% to about 50% of the serine and threonine amino acids in the tandem repeats have been replaced by tyrosine residues. In one embodiment, the mucin is MUC5AC (SEQ ID NO: 16) or MUC5B (SEQ ID NO: 17). In another embodiment, about 33% to about 50% of the serine and threonine amino acids have been replaced by tyrosine residues. In some embodiments, the N-terminal and C-terminal amino acids are cysteine.

The polypeptide can be selected from the group consisting of MUC5ACL (SEQ ID NO: 2), MUC5ACH (SEQ ID NO: 3), MUC5BL (SEQ ID NO: 4), MUC5BH (SEQ ID NO: 5), MUC5ACL-S(SEQ ID NO: 6), MUC5ACL-LT (SEQ ID NO: 7), MUC5ACL+D (SEQ ID NO: 8), MUC5ACLS-15 (SEQ ID NO: 6), pCoil-MUC5ACL-S(SEQ ID NO: 6), pCoil-MUC5ACL-LT (SEQ ID NO: 7), pCoil-MUC5ACL+D (SEQ ID NO: 8), MUC5ACL-S-Cold (SEQ ID NO: 6), GST-MUC5ACL-S(SEQ ID NO: 6), MBP-MUC5ACL-S(SEQ ID NO: 6), ELP 1:1 Y:S 10k (SEQ ID NO: 9), ELP 3:1 Y:S 10k (SEQ ID NO: 10), and MUC5ACLSS (SEQ ID NO: 11). In some embodiments, the polypeptide is selected from the group consisting of MUC5ACL (SEQ ID NO: 2), MUC5ACH (SEQ ID NO: 3), MUC5BL (SEQ ID NO: 4), MUC5BH (SEQ ID NO: 5), MUC5ACL-S(SEQ ID NO: 6), MUC5ACL-LT (SEQ ID NO: 7), and MUC5ACL+D (SEQ ID NO: 8). In some embodiments, the polypeptide is selected from the group consisting of MUC5ACLS-15 (SEQ ID NO: 6), pCoil-MUC5ACL-S(SEQ ID NO: 6), pCoil-MUC5ACL-LT (SEQ ID NO: 7), and pCoil-MUC5ACL+D (SEQ ID NO: 8). In some embodiments, the polypeptide is selected from the group consisting of MUC5ACL-S-Cold (SEQ ID NO: 6), GST-MUC5ACL-S(SEQ ID NO: 6), and MBP-MUC5ACL-S(SEQ ID NO: 6). In some embodiments, the polypeptide is selected from the group consisting of ELP 1:1 Y:S 10k (SEQ ID NO: 9), ELP 3:1 Y:S 10k (SEQ ID NO: 10), and MUC5ACLSS (SEQ ID NO: 11). In one embodiment, the polypeptide is MUC5ACL (SEQ ID NO: 2).

In some embodiments, the number of tandem repeat sequences ranges from about 15 to about 70. The length of the repeat sequence can range from about 700 Da to about 2 kDa. In some embodiments, a plurality of the tyrosine residues have been modified to include a substituent selected from the group consisting of alkyl, alkynyl, aryl, amino, carboxyl, heteroaryl, nitro, sulfate, and polyethylene oxide polymer. In one embodiment, the plurality is at least 20% of the tyrosine residues. In another embodiment, the plurality is at least 50% of the tyrosine residues. Also provided are pharmaceutical compositions comprising a polypeptide as described herein and a pharmaceutically acceptable carrier.

Disclosed herein are protein oligomers comprising at least two polypeptide units, wherein the polypeptide units comprise a plurality of tandem repeats of a sequence comprised by a mucin selected from the group consisting of MUC1 (SEQ ID NO: 12), MUC2 (SEQ ID NO: 13), MUC4 (SEQ ID NO: 14), MUC7 (SEQ ID NO: 15), MUC5AC (SEQ ID NO: 16) and MUC5B (SEQ ID NO: 17); and about 20% to about 50% of the serine and threonine amino acids in the protein oligomer have been replaced by tyrosine residues. All of the polypeptide embodiments disclosed above also describe the polypeptide units in the protein oligomers. Also provided are pharmaceutical compositions comprising a protein oligomer as described herein and a pharmaceutically acceptable carrier.

Preparation of Polypeptides and Protein Brushes

Figure 10:
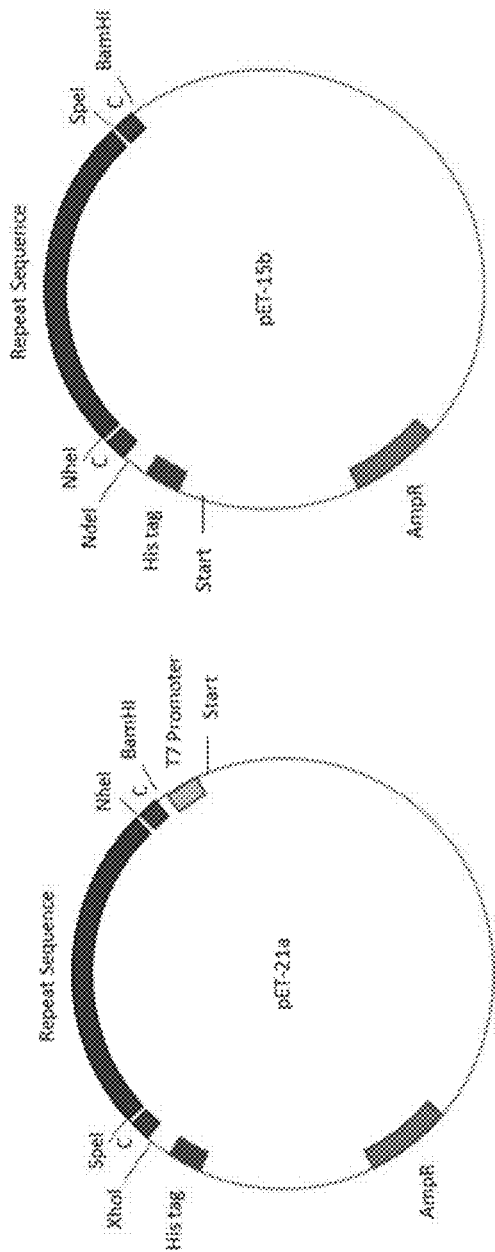
FIG. 10 depicts the pET-21a and pET-15b plasmid vectors for protein expression in E. coli.
Figure 11A:
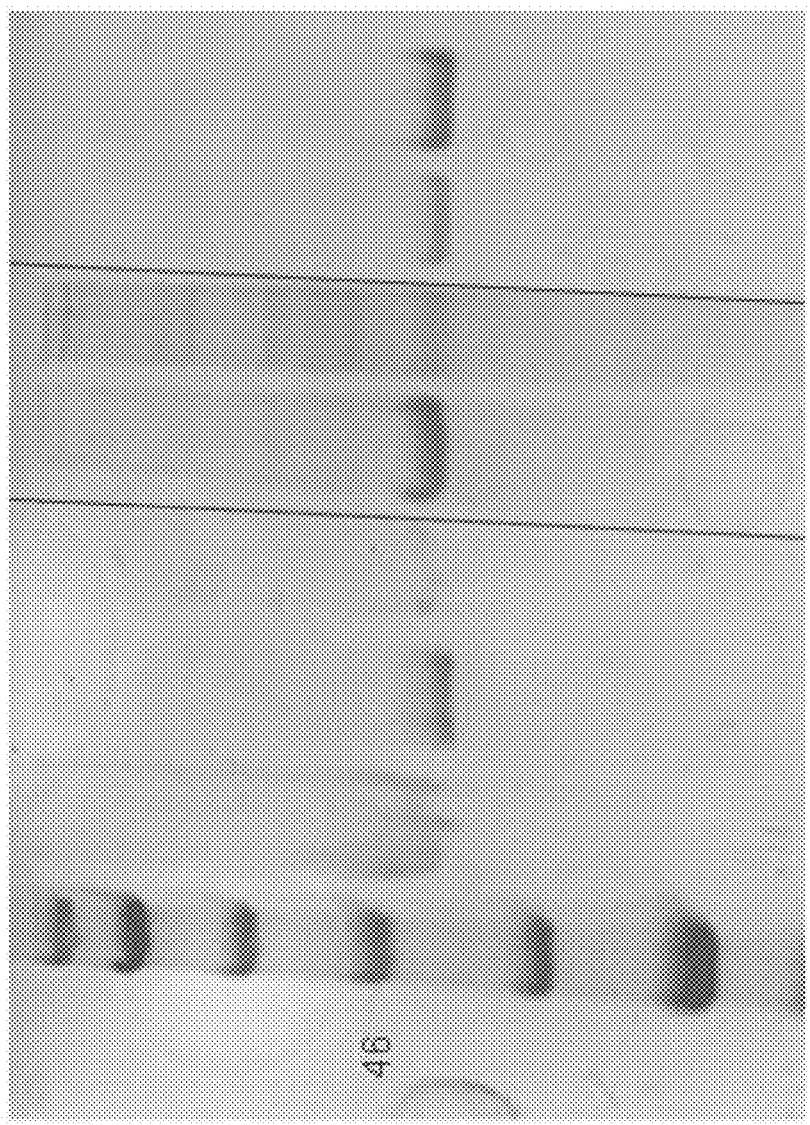
FIG. 11A depicts an SDS-PAGE image of the purified MUC5ACL (SEQ ID NO: 2) protein as a single band in the middle lanes.
Figure 11B:
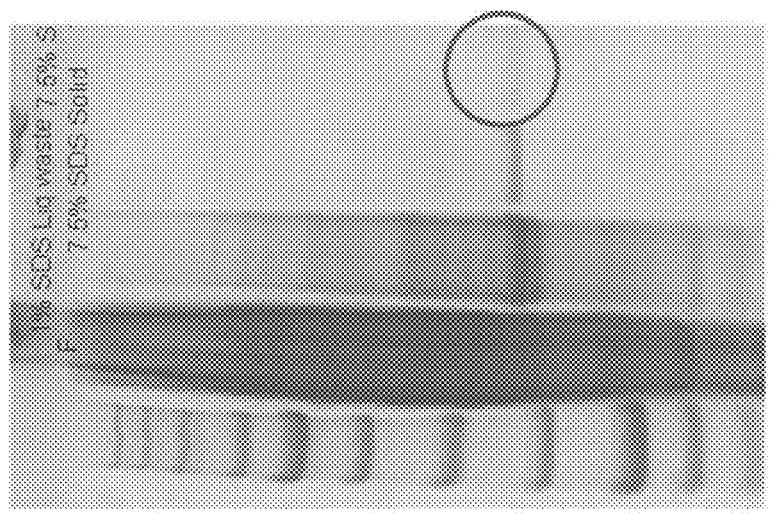
FIG. 11B depicts an SDS-PAGE image of the MUC5ACL (SEQ ID NO: 2) protein further treated with surfactant as a single band in the right lane.
Figure 12:
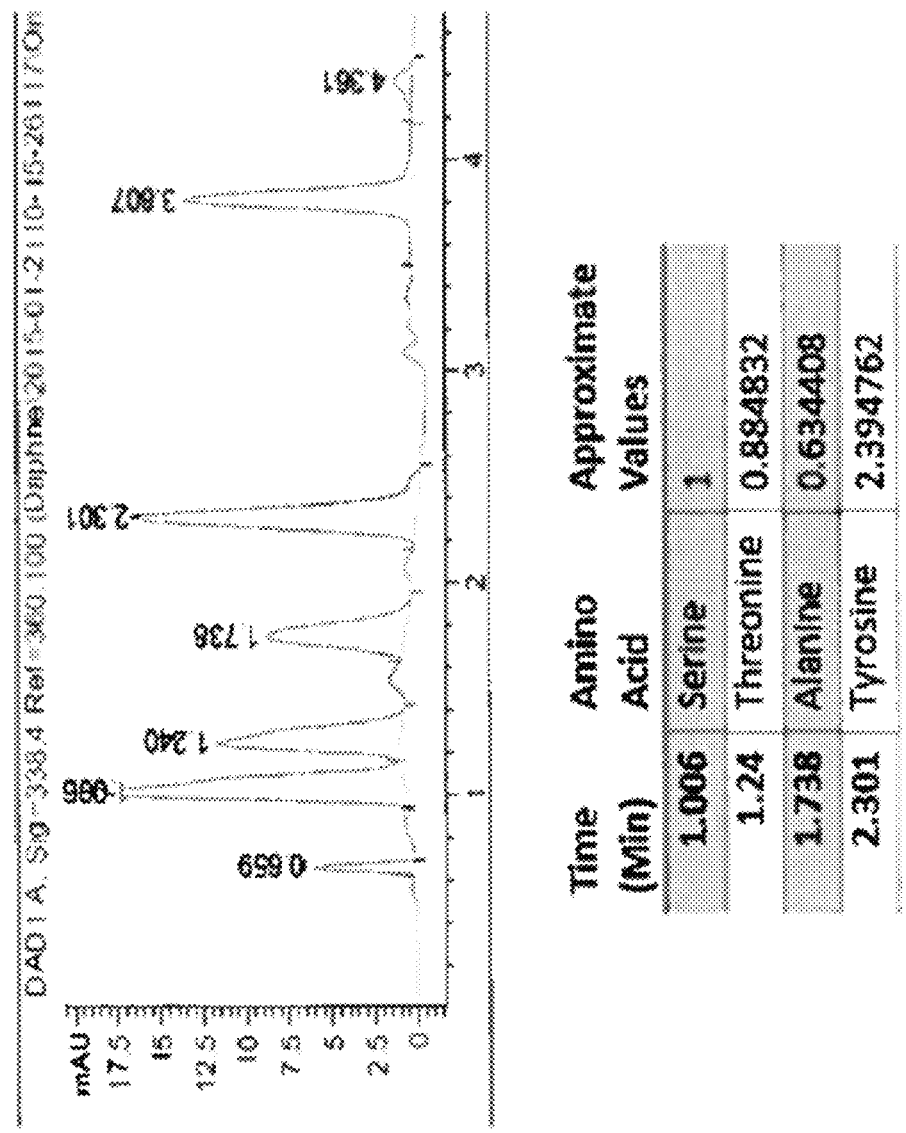
FIG. 12 depicts an amino acid analysis of the purified MUC5ACL (SEQ ID NO: 2) protein.
Figure 13:
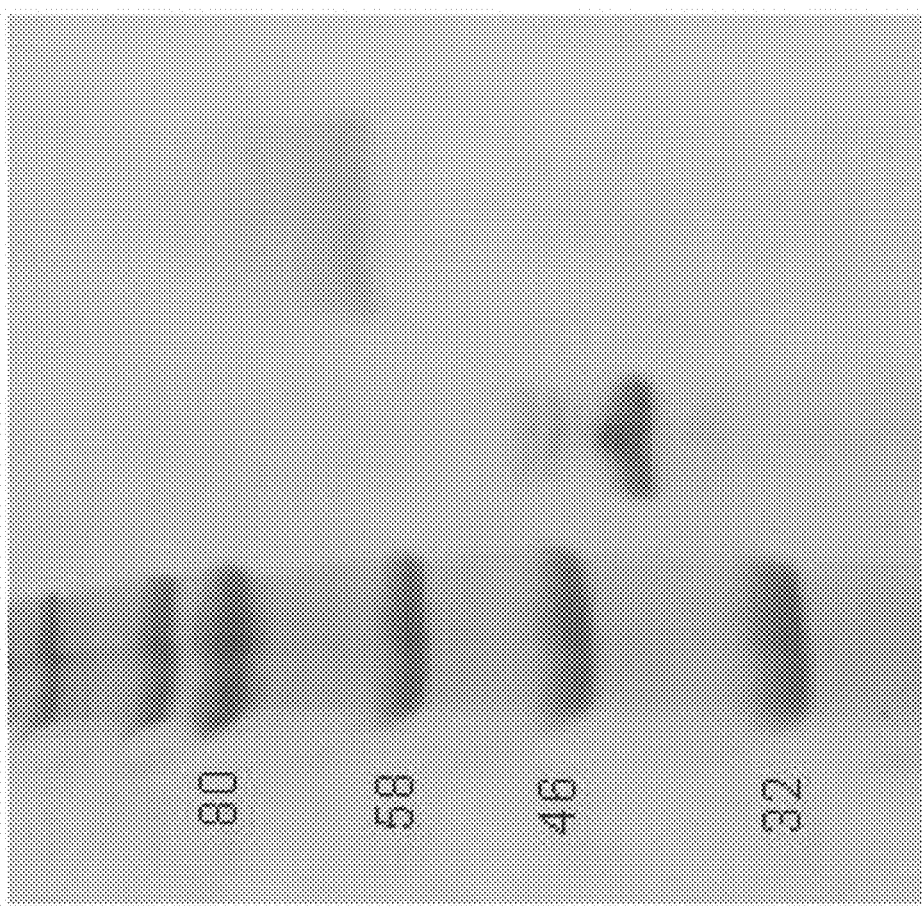
FIG. 13 depicts an SDS-PAGE image of the protein dimer that resulted from the oxidative disulfide coupling of two MUC5ACL (SEQ ID NO: 2) proteins as a single band in the right lane.

In preparing the disclosed protein brushes, the protein backbone mimics the VNTR of MUC5AC (SEQ ID NO: 16) and MUC5B (SEQ ID NO: 17), well-studied respiratory mucins. The most frequent sequence of the VNTR was extracted through the consensus sequence approach. From the consensus sequence, e.g., about 33% to about 50% of the hydroxylated amino acids (serine and threonine) were replaced with tyrosine in preparation for diazonium-coupling. Replacing those percentages of the amino acids in the consensus sequence mimics natural mucins where about 25% of the amino acids are glycosylated. The consensus sequence was repeated in a modular fashion and flanked with cysteine residues on both termini of the protein. The protein sequences are presented in FIG. 4 showing the tandem repeats and FIG. 10 illustrates the plasmid vectors used. The proteins were expressed in *E. coli* using standard vector-based techniques as described in Examples 1A-1D.

Disclosed herein are processes for preparing a polypeptide comprising a plurality of tandem repeats of a sequence comprised by a mucin selected from the group consisting of MUC1 (SEQ ID NO: 12), MUC2 (SEQ ID NO: 13), MUC4 (SEQ ID NO: 14), MUC7 (SEQ ID NO: 15), MUC5AC (SEQ ID NO: 16) and MUC5B (SEQ ID NO: 17), wherein about 20% to about 50% of the serine and threonine amino acids in the tandem repeats have been replaced by tyrosine residues, comprising a. expressing the polypeptide through use of a plasmid in a host cell; and b. isolating the polypeptide from the cell.

All of the polypeptide embodiments disclosed above also describe the polypeptide prepared by this process.

Disclosed herein are processes for preparing a protein oligomer comprising at least two polypeptide units, wherein the polypeptide units comprise a plurality of tandem repeats of a sequence comprised by a mucin selected from the group consisting of MUC1 (SEQ ID NO: 12), MUC2 (SEQ ID NO: 13), MUC4 (SEQ ID NO: 14), MUC7 (SEQ ID NO: 15), MUC5AC (SEQ ID NO: 16) and MUC5B (SEQ ID NO: 17); and about 20% to about 50% of the serine and threonine amino acids in the protein oligomer have been replaced by tyrosine residues, comprising linking at least two polypeptide units together through a disulfide bond between the N-terminus of one protein and the C-terminus of the other protein.

All of the polypeptide embodiments disclosed above also describe the polypeptide units used in this process for preparing a protein oligomer.

Post-Translational Modification of Tyrosine Residues

Diazonium coupling of an anionic azido-substituted compound to an aryl ring at the position ortho to a hydroxyl group affords a diazine linker as shown in FIG. 7. This reaction is very tolerant of substituents at the X position of the aniline and proceeds under mild conditions as described in Example 2. Thus, diazonium couplings are well suited to mass functionalization of up to about 60% to about 70% of tyrosine residues on a protein that can range from 150 kDa to about 1500 kDa. The disclosed reactions and results indicate that proteins can be post-translationally modified at protein length scale, rather than at single or discrete residues. The reagents are inexpensive and readily obtained, providing an economic method of mimicking the high molecular weight and densely functionalized mucins.

Disclosed herein are processes for preparing a polypeptide comprising a plurality of tandem repeats of a sequence comprised by a mucin selected from the group consisting of MUC1 (SEQ ID NO: 12), MUC2 (SEQ ID NO: 13), MUC4

(SEQ ID NO: 14), MUC7 (SEQ ID NO: 15), MUC5AC (SEQ ID NO: 16) and MUC5B (SEQ ID NO: 17), wherein about 20% to about 50% of the serine and threonine amino acids in the tandem repeats have been replaced by tyrosine residues, comprising modifying a plurality of the tyrosine residues by to a galactosyl group via a polyol linker. In other embodiments, X is phenyl, and the phenyl is substituted with an amido group. In some embodiments, R is H. In some embodiments, the plurality is at least 20% of the tyrosine residues, while in other embodiments, the plurality is at least 50% of the tyrosine residues.

Disclosed herein are processes for a protein oligomer comprising at least two polypeptide units, wherein the polypeptide units comprise a plurality of tandem repeats of a sequence comprised by a mucin selected from the group consisting of MUC1 (SEQ ID NO: 12), MUC2 (SEQ ID NO: 13), MUC4 (SEQ ID NO: 14), MUC7 (SEQ ID NO: 15), MUC5AC (SEQ ID NO: 16) and MUC5B (SEQ ID NO: 17); and about 20% to about 50% of the serine and threonine amino acids in the protein oligomer have been replaced by tyrosine residues, comprising modifying a plurality of the tyrosine residues by

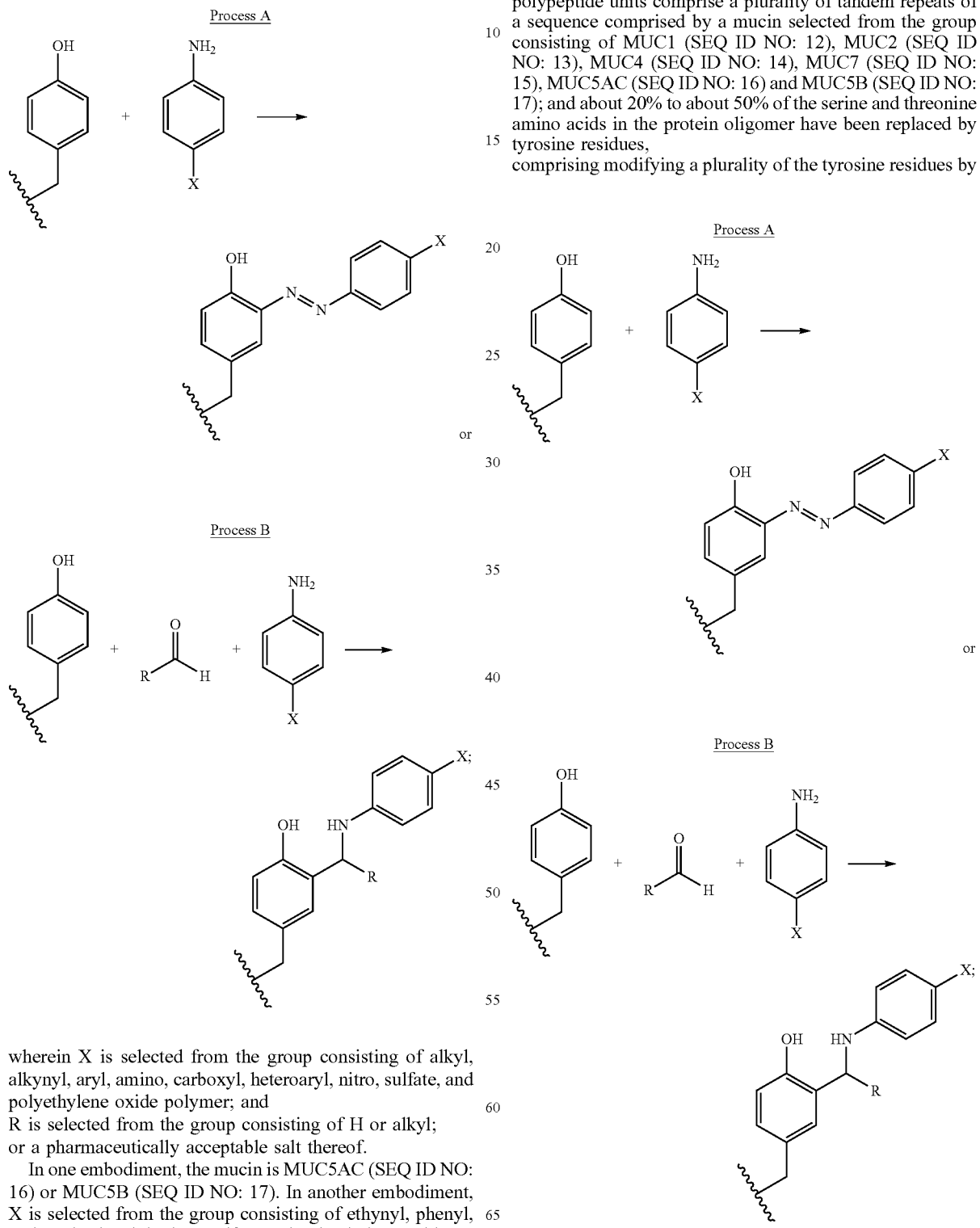

wherein X is selected from the group consisting of alkyl, alkynyl, aryl, amino, carboxyl, heteroaryl, nitro, sulfate, and polyethylene oxide polymer; and R is selected from the group consisting of H or alkyl;

or a pharmaceutically acceptable salt thereof.

In one embodiment, the mucin is MUC5AC (SEQ ID NO: 16) or MUC5B (SEQ ID NO: 17). In another embodiment, X is selected from the group consisting of ethynyl, phenyl, carboxyl, triazolyl, nitro, sulfate and polyethylene oxide. In some embodiments, X is triazolyl, and the triazolyl is linked wherein X is selected from the group consisting of alkyl, alkynyl, aryl, amino, carboxyl, heteroaryl, nitro, sulfate, and polyethylene oxide polymer; and R is selected from the group consisting of H or alkyl;

or a pharmaceutically acceptable salt thereof.

All of the embodiments described above for processes for preparing a polypeptide comprising modifying a plurality of the tyrosine residues by Process A or Process B also describe the above processes for preparing a protein oligomer comprising modifying a plurality of the tyrosine residues by Process A or Process B.

Compositions and Salts

In some embodiments, disclosed proteins can be in the form of a pharmaceutically acceptable composition. Disclosed herein are pharmaceutical compositions comprising a polypeptide as described herein and a pharmaceutically acceptable carrier. Also disclosed herein are pharmaceutical compositions comprising a protein oligomer as described herein and a pharmaceutically acceptable carrier.

Pharmaceutically acceptable carriers and excipients include inert solid diluents and fillers, diluents, including sterile aqueous solution and various organic solvents, permeation enhancers, solubilizers and adjuvants. Other components of a pharmaceutical composition as described herein include dispersion or suspension aids, surface active agents, isotonic agents, thickening or emulsifying agents, preservatives, solid binders, lubricants and the like.

Examples of suitable aqueous and nonaqueous carriers which can be employed in pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain adjuvants such as preservatives, wetting agents, emulsifying agents, dispersing agents, lubricants, and/or antioxidants. Prevention of the action of microorganisms upon the compounds described herein can be ensured by the inclusion of various antibacterial and antifungal agents, for example, paraben, chlorobutanol, phenol sorbic acid, and the like. It can also be desirable to include isotonic agents, such as sugars, sodium chloride, and the like into the compositions.

Methods of preparing these formulations or compositions include the step of bringing into association a compound described herein with the carrier and, optionally, one or more accessory ingredients. In general, the formulations are prepared by uniformly and intimately bringing into association a compound as disclosed herein with liquid carriers, or finely divided solid carriers, or both, and then, if necessary, shaping the product.

Preparations for such pharmaceutical compositions are well-known in the art. See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 2003; Goodman and Gilman, eds., The Pharmacological Basis of Therapeutics, Tenth Edition, McGraw Hill, 2001; Remington's Pharmaceutical Sciences, 20th Ed., Lippincott Williams & Wilkins, 2000; Martindale, The Extra Pharmacopoeia, Thirty-Second Edition (The Pharmaceutical Press, London, 1999); all of which are incorporated by reference herein in their entirety. Except insofar as any conventional excipient medium is incompatible with the compounds provided herein, such as by producing any undesirable biological effect or otherwise interacting in a deleterious manner with any other component(s) of the pharmaceutically acceptable composition, the excipient's use is contemplated to be within the scope of this disclosure.

Provided herein are pharmaceutically acceptable salts which refer to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in J. Pharmaceutical Sciences (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, organic acids from which salts can be derived include, for example, acetic acid, propionic acid, glycolic acid, pyruvic acid, oxalic acid, lactic acid, trifluoracetic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The salts can be prepared in situ during the isolation and purification of the disclosed compounds, or separately, such as by reacting the free base or free acid of the compound with a suitable base or acid, respectively. Pharmaceutically acceptable salts derived from appropriate bases include alkali metal, alkaline earth metal, ammonium and $N^+ (C_{1-4}alkyl)_4$ salts. Representative alkali or alkaline earth metal salts include sodium, lithium, potassium, calcium, magnesium, iron, zinc, copper, manganese, aluminum, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Organic bases from which salts can be derived include, for example, primary, secondary, and tertiary amines, substituted amines, including naturally occurring substituted amines, cyclic amines, basic ion exchange resins, and the like, such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

Commercial Applications

Naturally occurring mucin in the body acts as one of the primary barriers to pathogens reaching cells. Any toxin or pathogen that reaches the lungs, the gut, the reproductive tract or the eye is immersed in mucus, and its performance will be defined by this interaction. Mucins provide a physical barrier around cells that serve as a trap for microbes and a matrix for antimicrobial molecules. Given the difficulty of isolating natural mucins from cellular tissues, inexpensive and effective mucin mimetics as described herein are of interest to the defense industry in developing new protection methods against deleterious biological agents, such as those used in biological warfare. These types of barrier systems would easily form air and vapor-permeable membranes that could be used for protection of personnel and other critical assets during a biological threat. Such selective tents, suits, or air barriers would allow personnel to maintain functional capability during a biological incident for extended periods of time.

In another application, mucin mimetics as described herein are of interest to the pharmaceutical industry, such as in pharmacokinetic and pharmacodynamics testing of drug candidates. Mucin coatings on cells can identify a drug as a potential toxin, rather than a nutrient, and prevent drugs from reaching their intended cellular targets. To assess a drug candidate's ability to permeate mucin, testing on the disclosed mucin mimetics provide important insights into how that drug would interact in vivo. The process of mass functionalization of proteins, rather than step-wise or individual residue approaches, as described herein will find many applications in producing mucin mimetics and other functionalized proteins for creating new protein-based materials.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

Incorporation by Reference

All U.S. patents and U.S. and PCT published patent applications mentioned in this specification are herein incorporated by reference to the same extent as if each independent patent and publication was specifically and individually indicated to be incorporated by reference.

EXAMPLES

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

The following examples are put forth so as to provide those of ordinary skill in the art with a complete disclosure and description of how to make and use the compounds and methods of the invention, and are not intended to limit the scope of what the inventor(s) regard(s) as the invention.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

Unless noted otherwise, the starting materials for the synthesis described herein were obtained from commercial sources or known synthetic procedures and were used without further purification.

Example 1A: Protein Synthesis of MUC5ACL (SEQ ID NO: 2), MUC5ACH (SEQ ID NO: 3), MUC5BL (SEQ ID NO: 4) and MUC5BH (SEQ ID NO: 5)

The protein backbones were cloned in the pET-15b vector as shown in FIG. 10, which features ampicillin resistance, a T7 promoter system and an N-terminal histag for aid in purification. Plasmids for the genes of the protein series were synthesized by Genscript with the restriction site patterns of BamHI-MUC5X-Hindlll for pET-15b and BamHI-MUC5X-Xhol for pET-21a. The proteins were expressed in C43 cells at 37° C. in TB media for 16-20 hours with protein expression induced through adding 0.5 mM IPTG once the 00600 was equal to 1. The cells were harvested by centrifugation, lysed and sonicated in denaturing buffer solution (8 M Urea, 1 wt % SDS, 100 mM $Na_2HPO_4$, 20 mM Tris, pH 10). The insoluble fraction was collected and then washed with a denaturing buffer solution containing 2 M NaCl, 8M Urea, 1 wt % SDS, 100 mM $Na_2HPO_4$, 20 mM Tris, pH 10. The liquid fraction is collected and dialyzed against MilliQ water and then lyophilized.

The MUC5ACL (SEQ ID NO: 2) protein was prepared as described above in 25 mg protein/L of culture media. This artificially created protein based on MUC5 had about 33% of its serine and threonine residue replaced by tyrosine. The protein repeating sequence was $(YTSTYSAP)_{46}$ (SEQ ID NO: 1) and flanked by cysteine residues giving CAS$(YTSTYSAP)_{46}$TSC (SEQ ID NO: 2) with a total of 374 amino acids. The protein product was characterized by SDS-PAGE and amino acid analysis. FIG. 11A shows an SDS-PAGE image where the middle lanes show the lyophilized product as a single band, while FIG. 11B shows a SDS-PAGE image after treatment with surfactant with the right-hand lane having a single band. The amino acid analysis shown in FIG. 12 confirmed the identity of MUC5ACL (SEQ ID NO: 2) and showed the enrichment of the tyrosine residues over the native protein. The SDS-PAGE image in FIG. 13 also shows the result of coupling two MUC5ACL (SEQ ID NO: 2)

proteins using oxidative conditions to form a disulfide bond evident in the higher band in the right lane. The right lane shows the higher molecular weight product as a single band.

Figure 14:
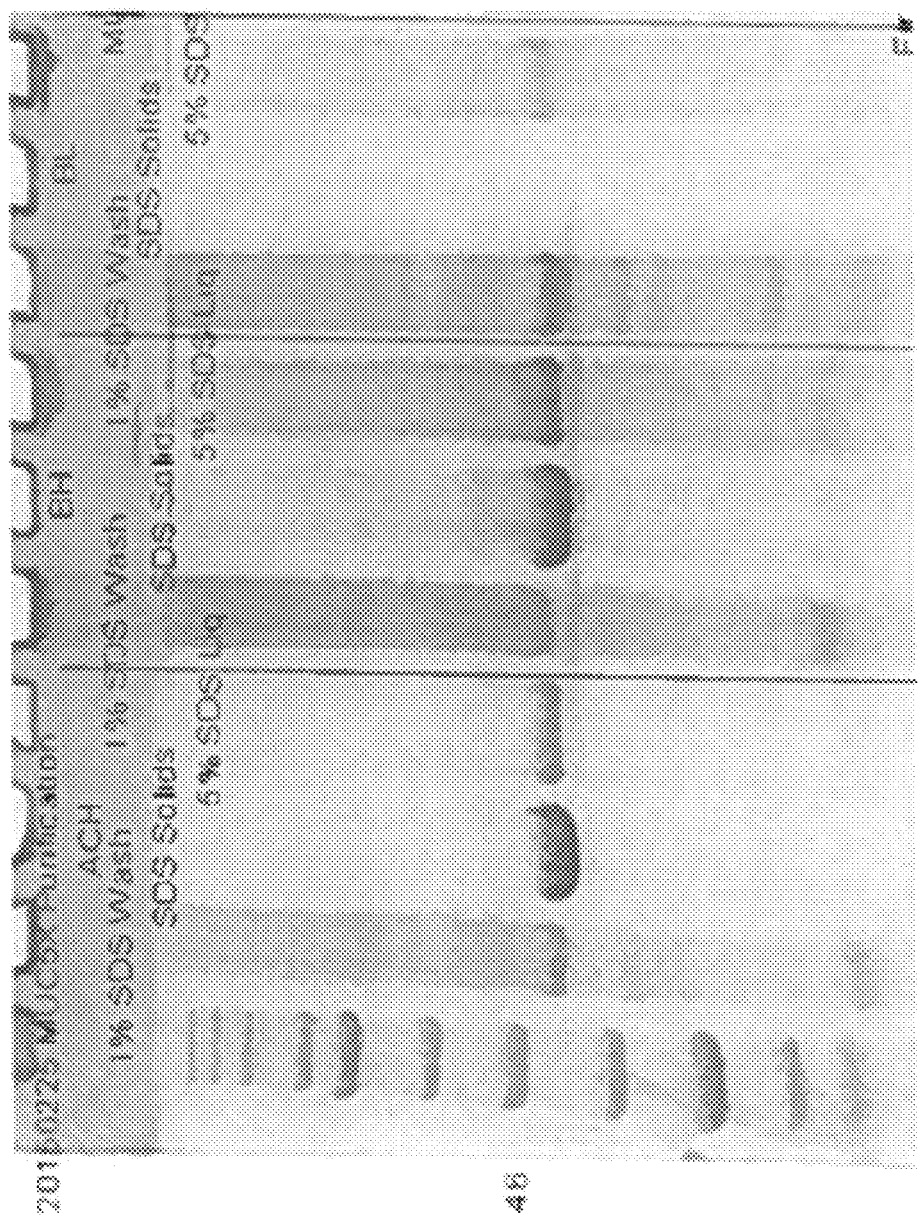
FIG. 14 depicts an SDS-PAGE image of purified MUC5ACH (SEQ ID NO: 3), MUC5BL (SEQ ID NO: 4) and MUC5BH (SEQ ID NO: 5) proteins.

As shown in FIG. 14, the MUC5ACH (SEQ ID NO: 3), MUC5BL (SEQ ID NO: 4) and MUC5BH (SEQ ID NO: 5) proteins were synthesized in a similar manner with significant levels of expression.

Example 1B: Protein Synthesis of MUC5ACL-S(SEQ ID NO: 6), MUC5ACL-LT (SEQ ID NO: 7) and MUC5ACL+D (SEQ ID NO: 8)

The procedure for synthesizing pcoilcoil-mini intein proteins MUC5ACL-S(SEQ ID NO: 6), MUC5ACL-LT (SEQ ID NO: 7) and MUC5ACL+D (SEQ ID NO: 8) was similar to that of MUC5ACL (SEQ ID NO: 2) described in Example 1A, except the pET-21A vector was used and the isolation procedure was as follows. Their sequences are detailed in FIG. 15. The solids were precipitated using sonication using 10 wt % ammonium sulfate. The solids were purified using an Ni-NTA column with the solvent phase as 8M urea in pH8 buffer. After collecting product-containing fractions and isolation, the protein was further purified using FPLC in a pH 10 buffer solvent phase. Finally, the liquid fractions were collected and dialyzed against MilliQ water and then lyophilized.

Figure 16:
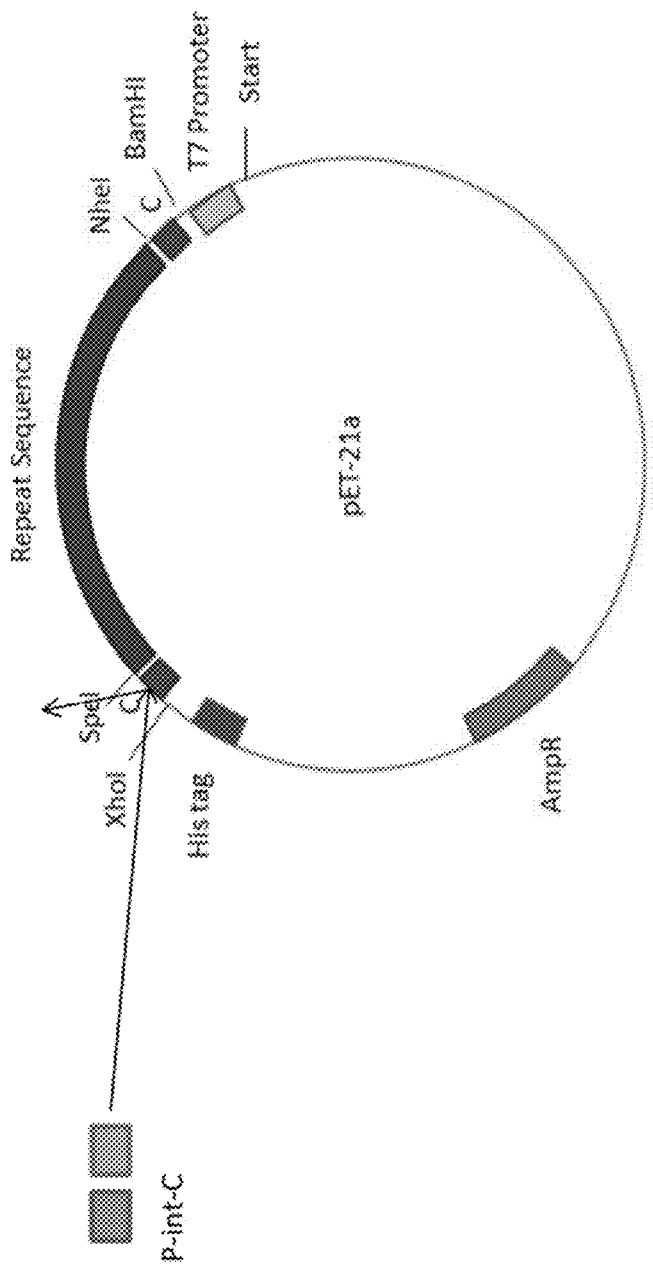
FIG. 16 depicts the pEt-21a vector containing the P-int-C insertion to create the pcoilcoil-mini intein proteins.
Figure 17:
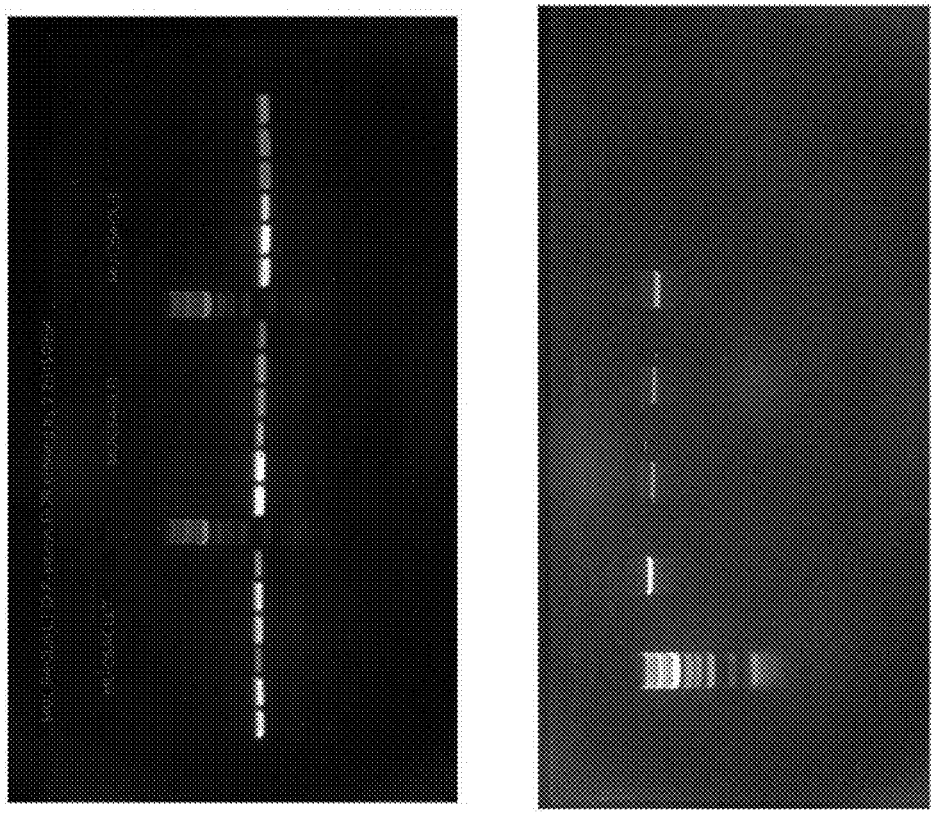
FIG. 17 depicts the PCR process to clone the coexpression genes to create the proteins of FIG. 15.
Figure 18:
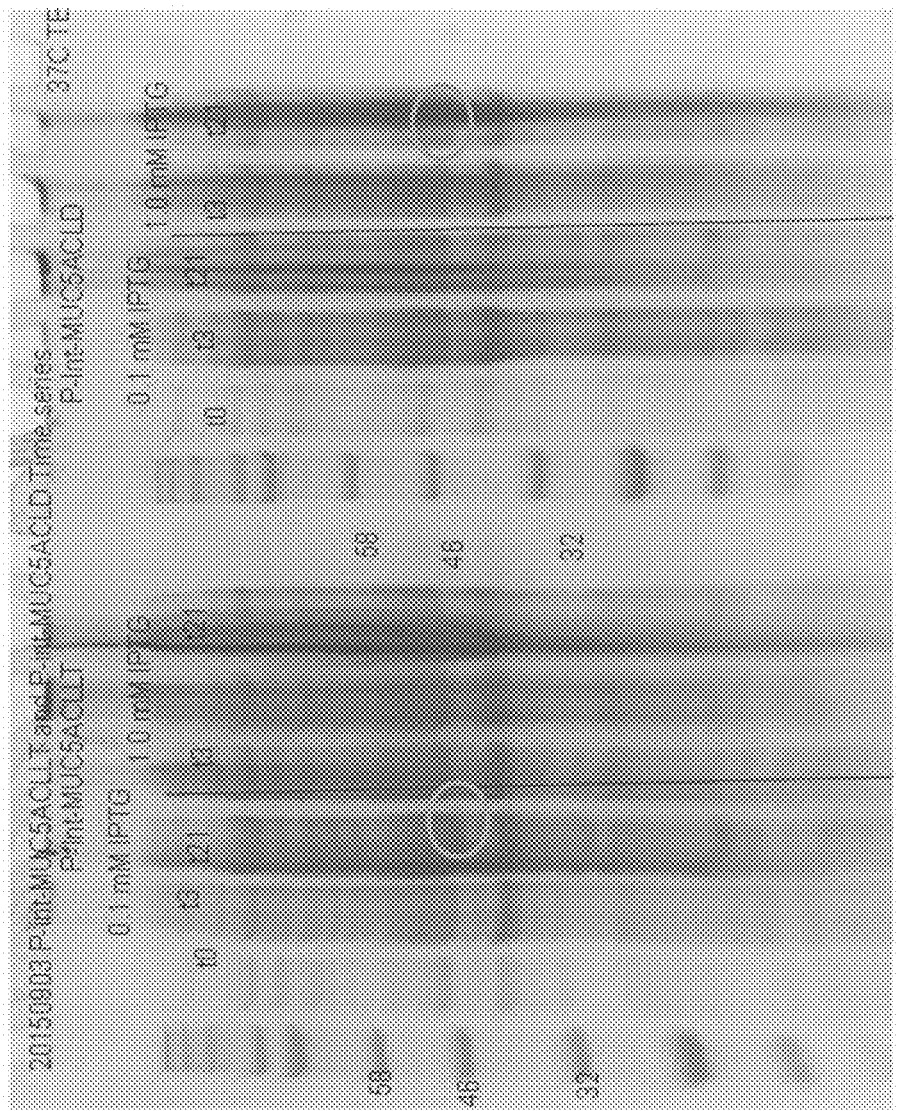
FIG. 18 depicts an SDS-PAGE image of three purified pcoilcoil-mini intein proteins indicating significant expression of each one.

The expression results were determined by SDS-PAGE. Low levels of protein expression led to co-expressing these proteins with P-coiled-coil-mini-Intenin that was expressed using a pET-21a vector as shown in FIG. 16. The PCR cloning of the coexpression genes is shown in FIG. 17. All three mucin-mimetic proteins were significantly expressed as shown by SDS-PAGE in FIG. 18.

Example 1C: Protein Synthesis of MUC5ACL-S-Cold (SEQ ID NO: 6), GST-MUC5ACL-S (SEQ ID NO: 6), and MBP-MUC5ACL-S (SEQ ID NO: 6)

Figures 19A, 19B:
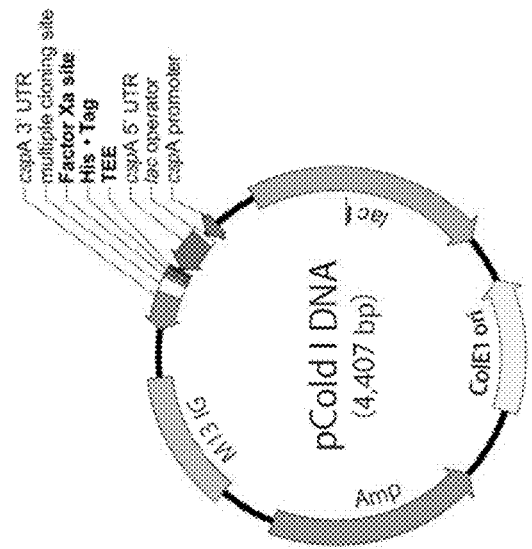
FIG. 19A depicts the sequences of the MUC5ACL-S-Cold (SEQ ID NO: 6), GST-MUC5ACL-S(SEQ ID NO: 6), and MBP-MUC5ACL-S(SEQ ID NO: 6) proteins and vectors used to express them in E. coli. In order of appearance, FIG. 19A discloses SEQ ID NOS: 6, 6 and 6.
FIG. 19B depicts the plasmid vector of pColdI.
Figure 21:
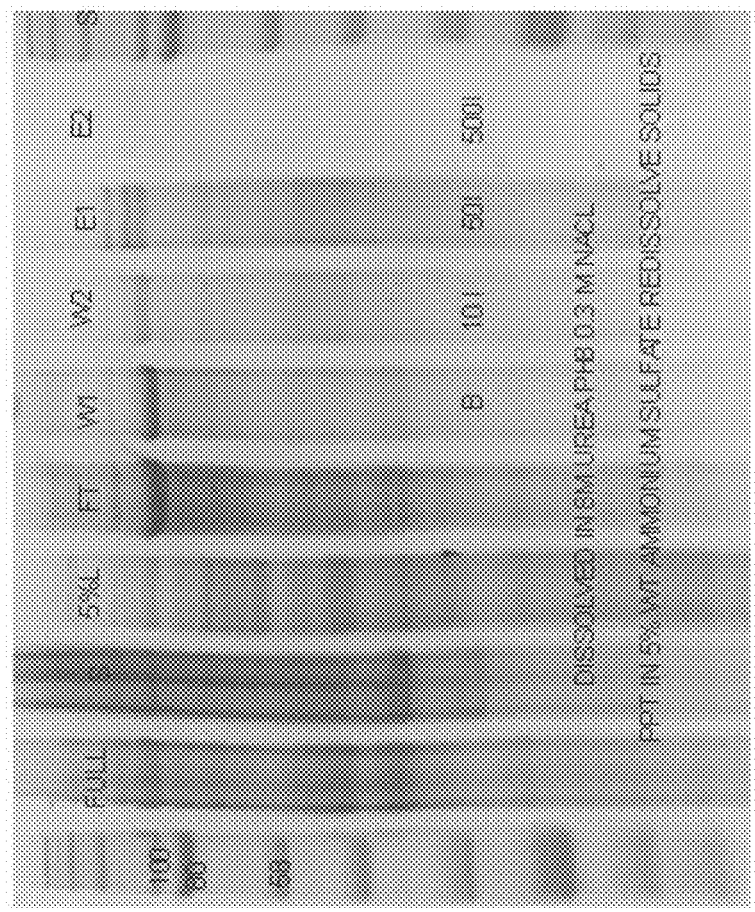
FIG. 21 depicts an SDS-PAGE image of purified MBP-MUC5ACL-S(SEQ ID NO: 6).

The sequences of the MUC5ACL-S-Cold (SEQ ID NO: 6), GST-MUC5ACL-S(SEQ ID NO: 6), and MBP-MUC5ACL-S(SEQ ID NO: 6) proteins are given in FIG. 19A. The procedure for synthesizing MUC5ACL-S-Cold (SEQ ID NO: 6) was similar to that of MUC5ACL (SEQ ID NO: 2) described in Example 1A, except that a pCOLDI vector was used as shown in FIG. 19B instead of the pET-21a vector. However, a Western blot revealed that the pCOLDI vector did not express. The GST-MUC5ACL-S (SEQ ID NO: 6), and MBP-MUC5ACL-S(SEQ ID NO: 6) proteins were synthesized in a similar manner to Example 1A, except that a pGEX-4T1 vector was used for GST-MUC5ACL-S(SEQ ID NO: 6) and a p-MAL-c5E vector was used for MBP-MUC5ACL-S(SEQ ID NO: 6). SDS-PAGE and Western blots for GST-MUC5ACL-S(SEQ ID NO: 6) and MBP-MUC5ACL-S(SEQ ID NO: 6) indicated good levels of expression as shown in FIG. 20 and FIG. 21, respectively.

Example 1D: Protein Synthesis of ELP 1:1 Y:S 10k (SEQ ID NO: 9), ELP 3:1 Y:S 10k (SEQ ID NO: 10), and MUC5ACLSS (SEQ ID NO: 11)

Figure 23:
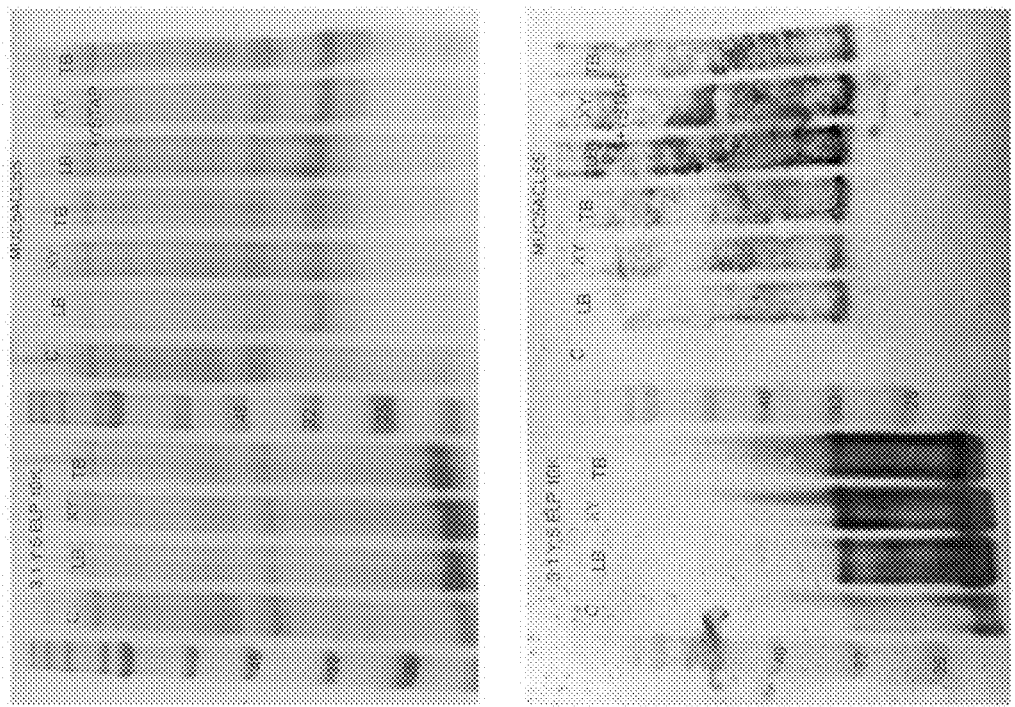
FIG. 23 depicts an SDS-PAGE image (top) and Western Blot (bottom) of purified MUC5ACLSS (SEQ ID NO: 11).

The sequences of the ELP 1:1 Y:S 10k (SEQ ID NO: 9), ELP 3:1 Y:S 10k (SEQ ID NO: 10), and MUC5ACLSS (SEQ ID NO: 11) proteins are given in FIG. 22. The procedure for synthesizing each protein was similar to that of MUC5ACL (SEQ ID NO: 2) described in Example 1A, except that pET-15b was used as the vector. SDS-PAGE and Western blots for ELP 3:1 Y:S 10k (SEQ ID NO: 10), and MUC5ACLSS (SEQ ID NO: 11) indicate full expression of the proteins as shown in FIG. 23.

Example 2: Tyrosine Modification

Figure 24:
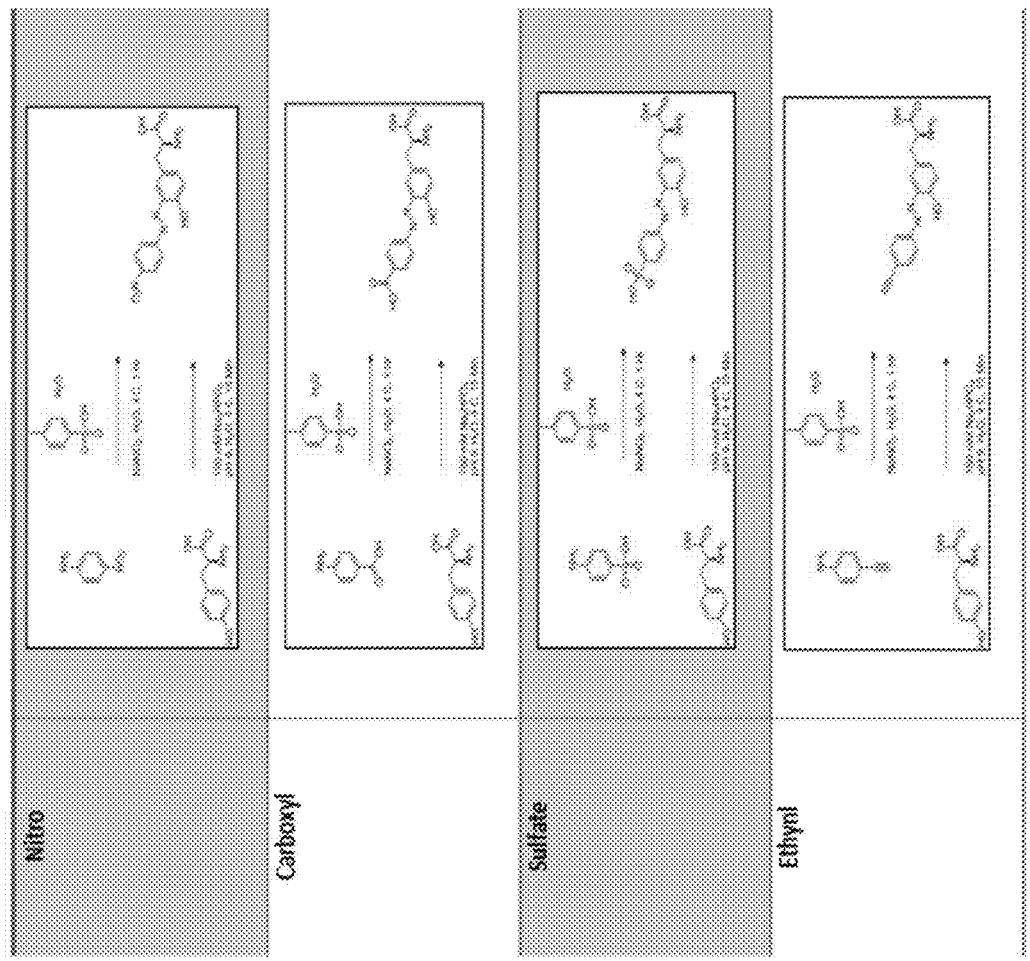
FIG. 24 depicts the diazonium coupling reactions for X-substituted anilines A as shown in FIG. 7. Reaction conditions are shown for X as nitro, carboxyl, sulfate, ethynyl, triazolyl-galactosyl (galactose) and triazolyl-PEO (PEO200).
Figure 24:
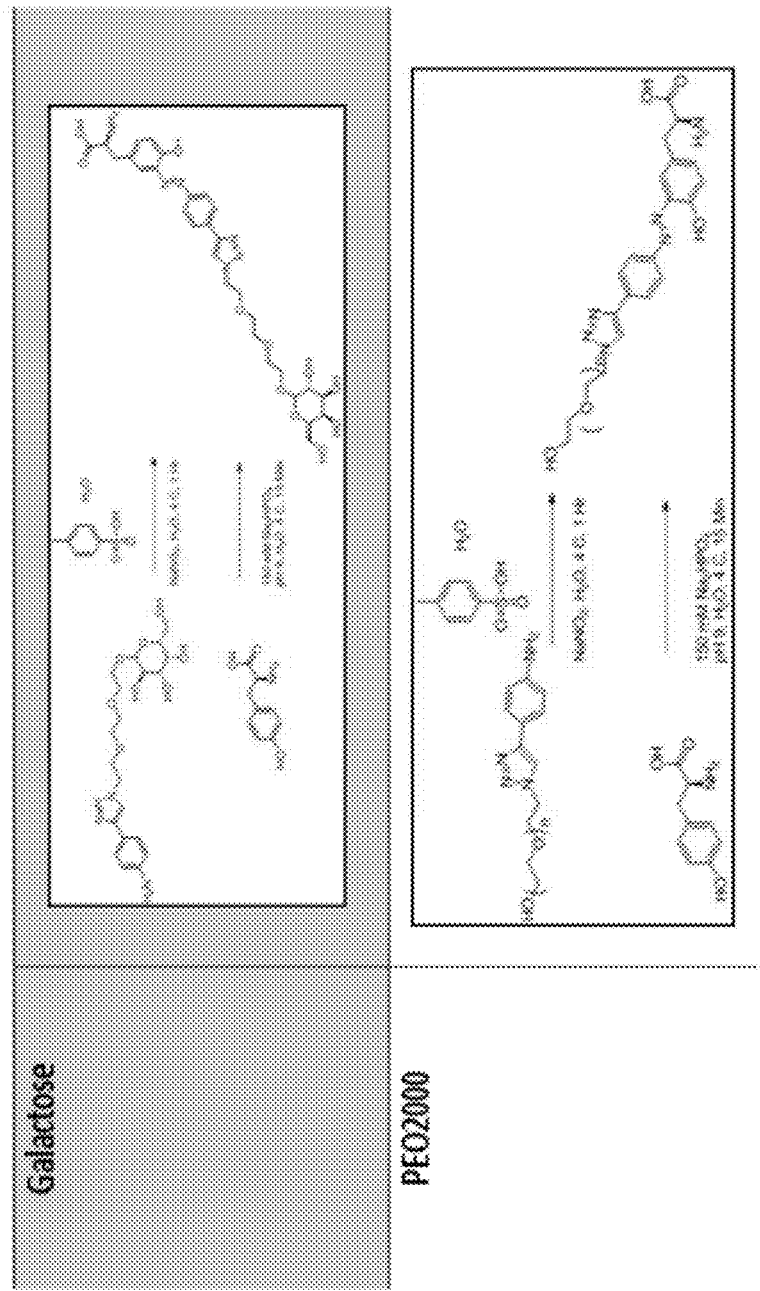
Figure 25:
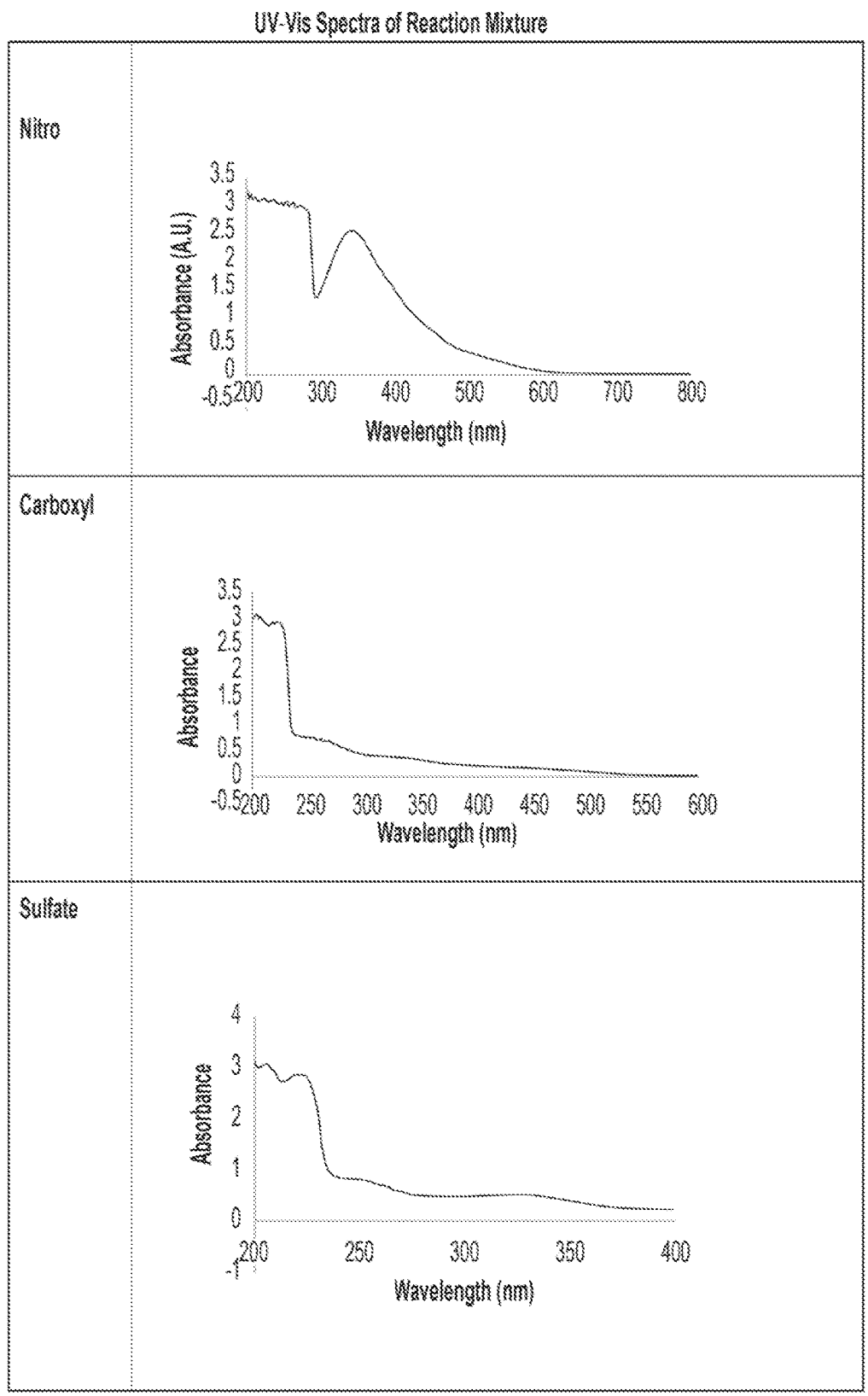
FIG. 25 depicts UV-Vis and MS spectra for each diazonium product shown in FIG. 24.
Figure 25:
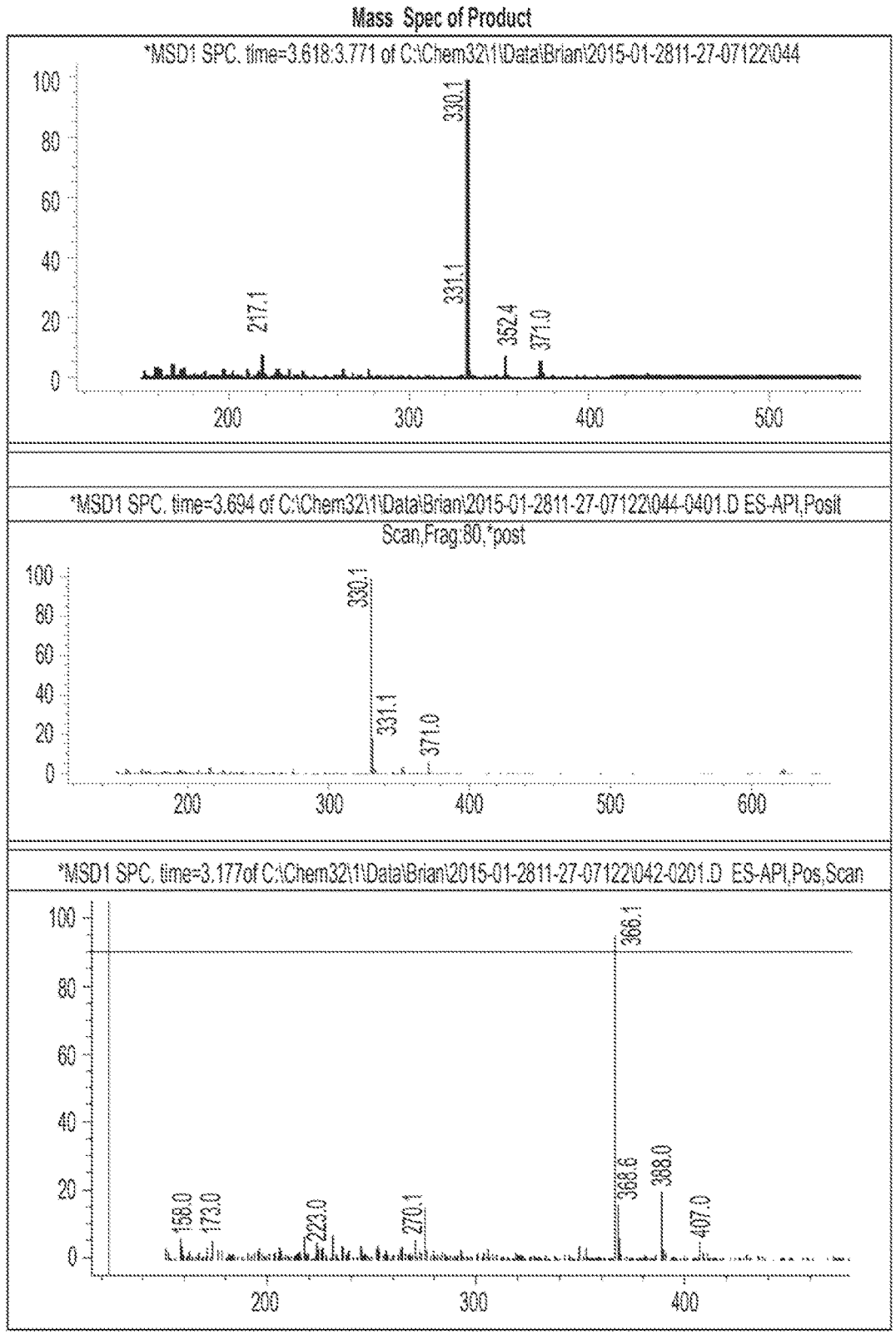
Figure 25:
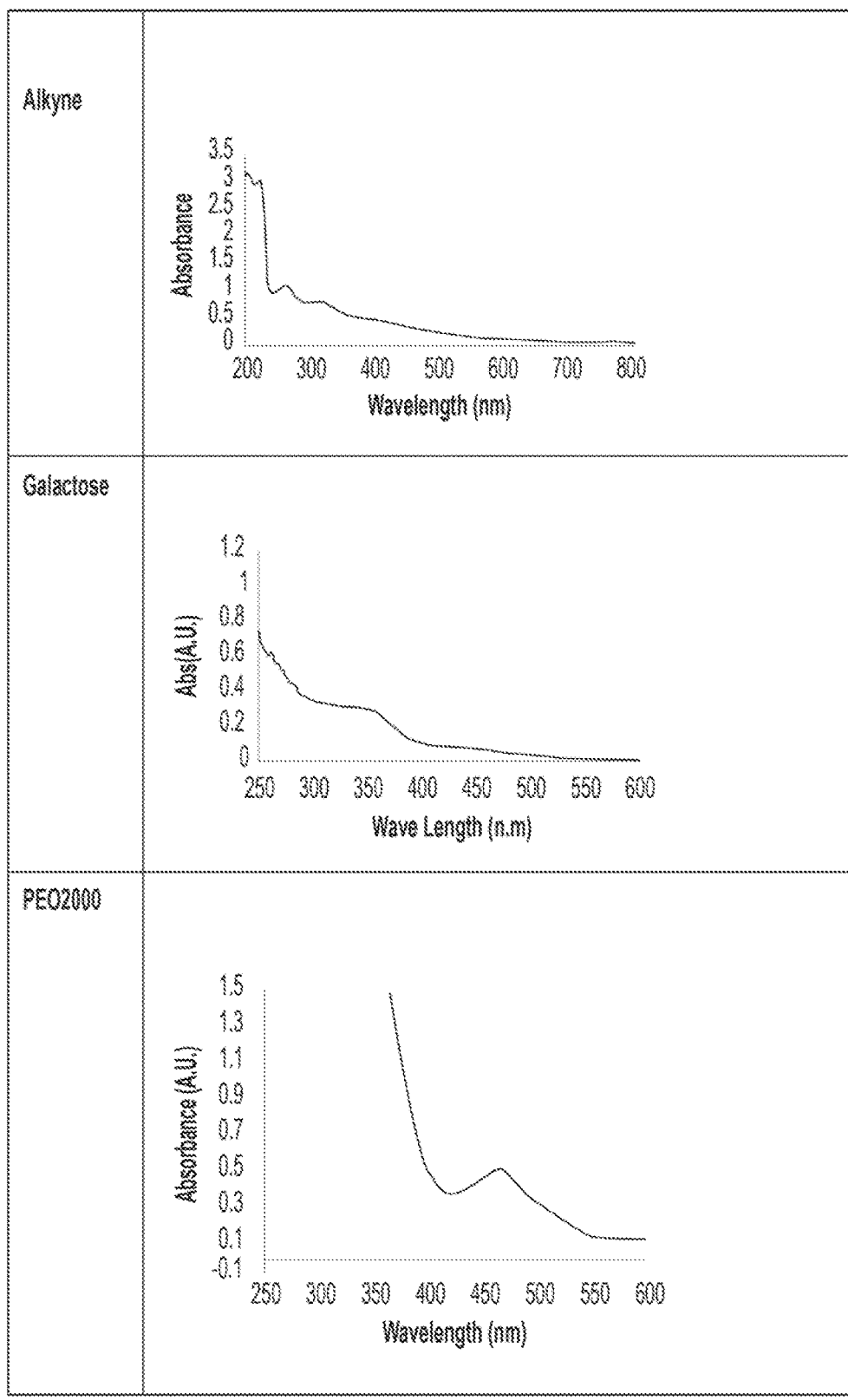
Figure 25:
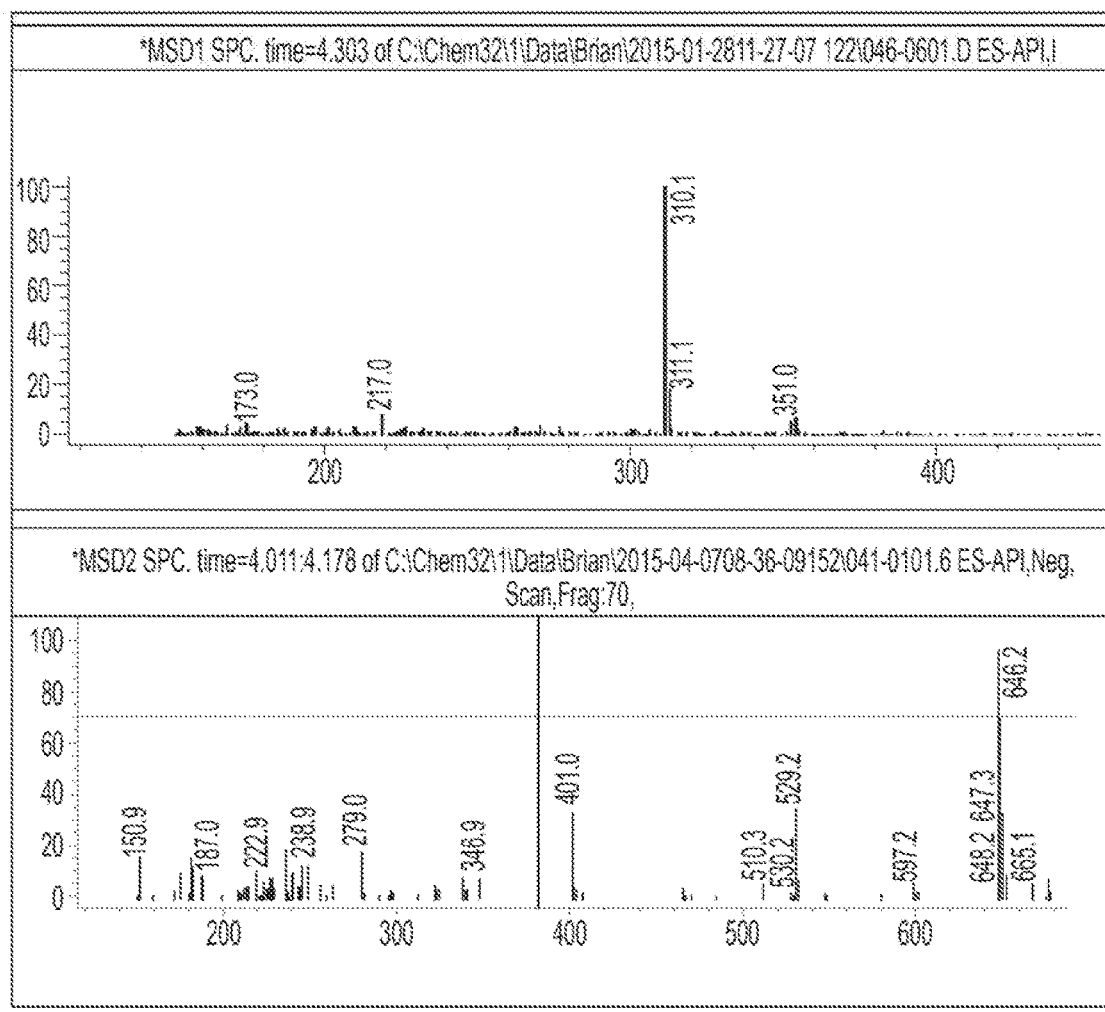
Figure 25:
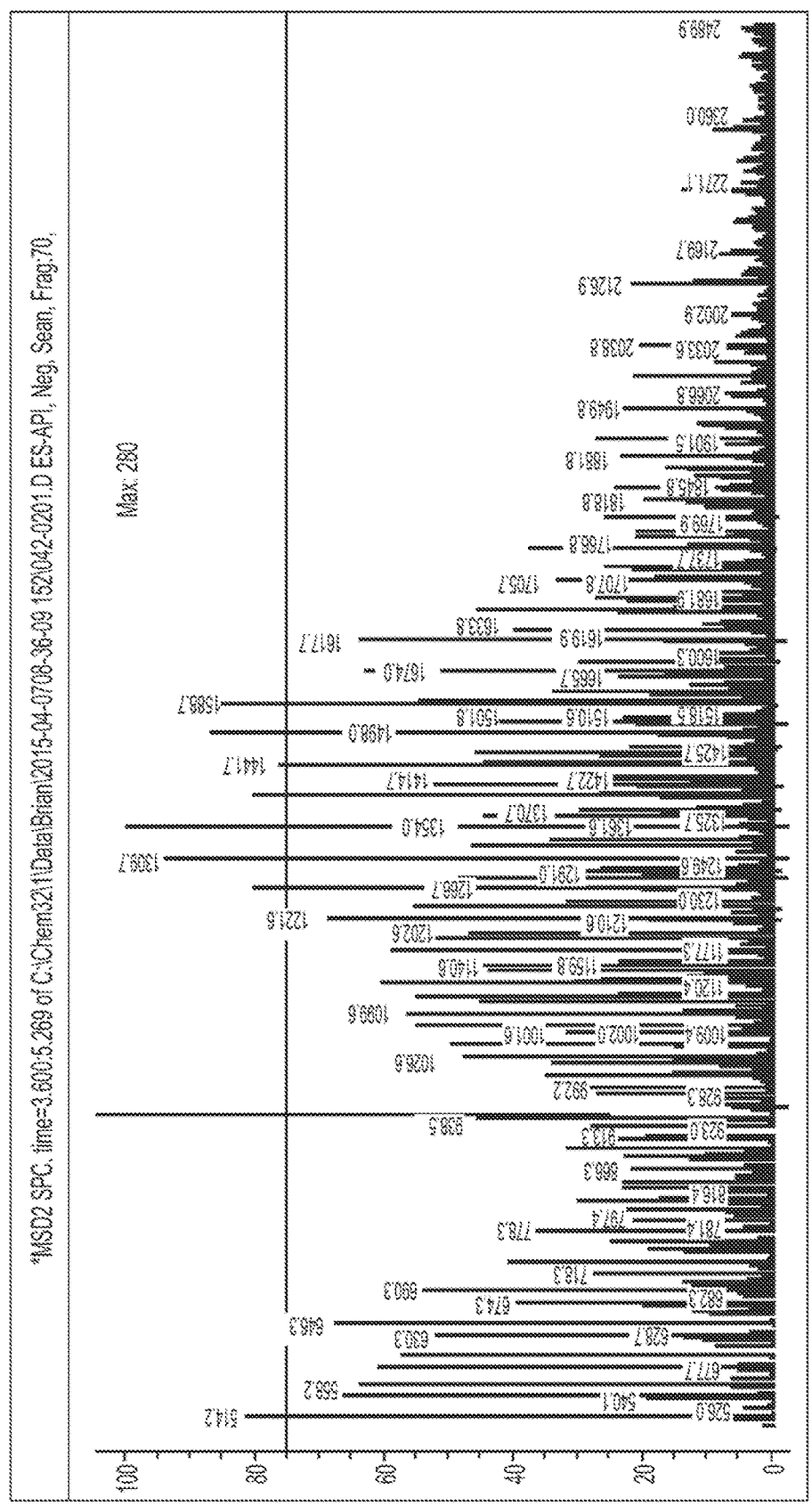

As shown in FIG. 7, anilines of Formula A, where X is selected from ethynyl, carboxyl, triazolyl, nitro, sulfate and polyethylene oxide, were dissolved in a 20 mg/ml of MilliQ water. This solution was mixed in a 2:1:1 volume ratio of functional group solution, p-toluesulfilic acid solution (32 mg/ml in MilliQ water), and sodium nitrite solution (160 mg/ml in MilliQ water). This mixture was rocked for 1 hour at 4° C. to form a diazonium salt solution. L-tyrosine was added to 1.2 mg/ml buffer solution (150 mM $Na_2HPO_4$, pH 9, MilliQ water). The diazonium salt solution was added to the tyrosine solution with a 1.5× molar excess of salt solution. The specific diazonium couplings for each X substituent are detailed in FIG. 24. The diazonium coupling adduct was characterized via UV-vis spectroscopy and LC-MS as shown in FIG. 25. From the UV-Vis spectra, the yield of diazonium functionalization on compound B was determined as given in TABLE 1.

TABLE 1

| Compound B diazine substituent | Yield % |
|---|---|
| nitro | 69 |
| sulfate | 80 |
| carboxyl | 75 |
| ethynyl | 25 |
| triazolyl-PEO | 33 |
| triazolyl-galactosyl | 53 |

Figure 26:
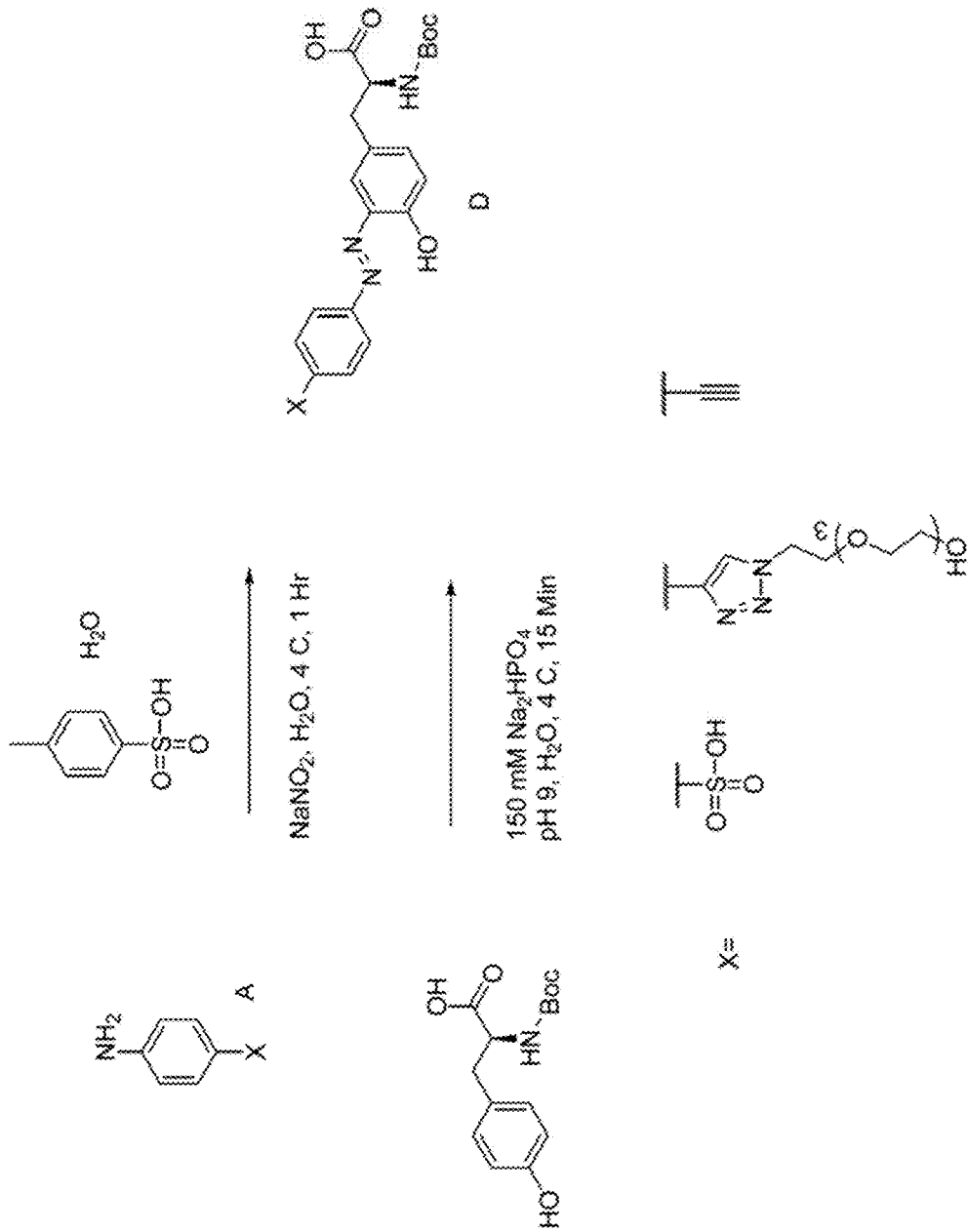
FIG. 26 depicts functionalization of Boc-protected tyrosine with X-substituted aniline A using a diazonium coupling procedure. The X substituents were sulfate, triazolyl-PEO, and ethynyl.

A second method of tyrosine modification involved using Boc-protected tyrosine as a starting material, which gave increased solubility. The reaction conditions were as described above for unprotected tyrosine as shown in FIG. 26. The aniline of Formula A having variable X as sulfate, triazolyl-PEO (PEO), and ethynyl (alkyne) were successfully used to produce Boc-protected compounds of Formula D.

Figure 27:
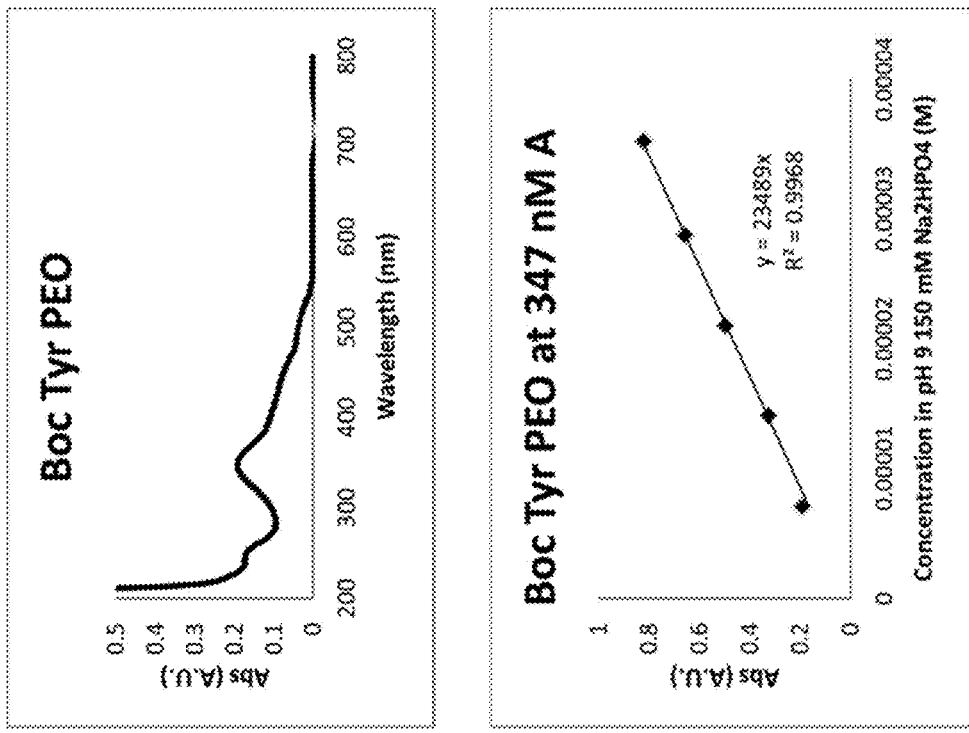
FIG. 27 depicts the UV-Vis spectra of the three Boc-protected diazonium products and their extinction coefficients.

The coupling products were purified by first lyophilizing the reaction mixture. The solids were dissolved in ethyl acetate, filtered, and then passed through a silica gel column (ethyl acetate: methanol). The solvent was removed via reduced pressure. The solids were then dissolved in methanol and purified by HPLC. The products were characterized with $^1H$ NMR and LRMS. The extinction coefficients were determined by UV-Vis spectroscopy of solutions in 150 mM PBS at pH 9 as shown in FIG. 27 and TABLE 2.

TABLE 2

| | ε (L/(mol cm)) | Wavelength (nm) |
|---|---|---|
| PEO | 26000 ± 9200 | 347 |
| Alkyne | 9600 ± 400 | 338 |
| Sulfate | 6700 ± 1400 | 328 |

Example 3: Protein Tyrosine Residue Modification

Figure 28:
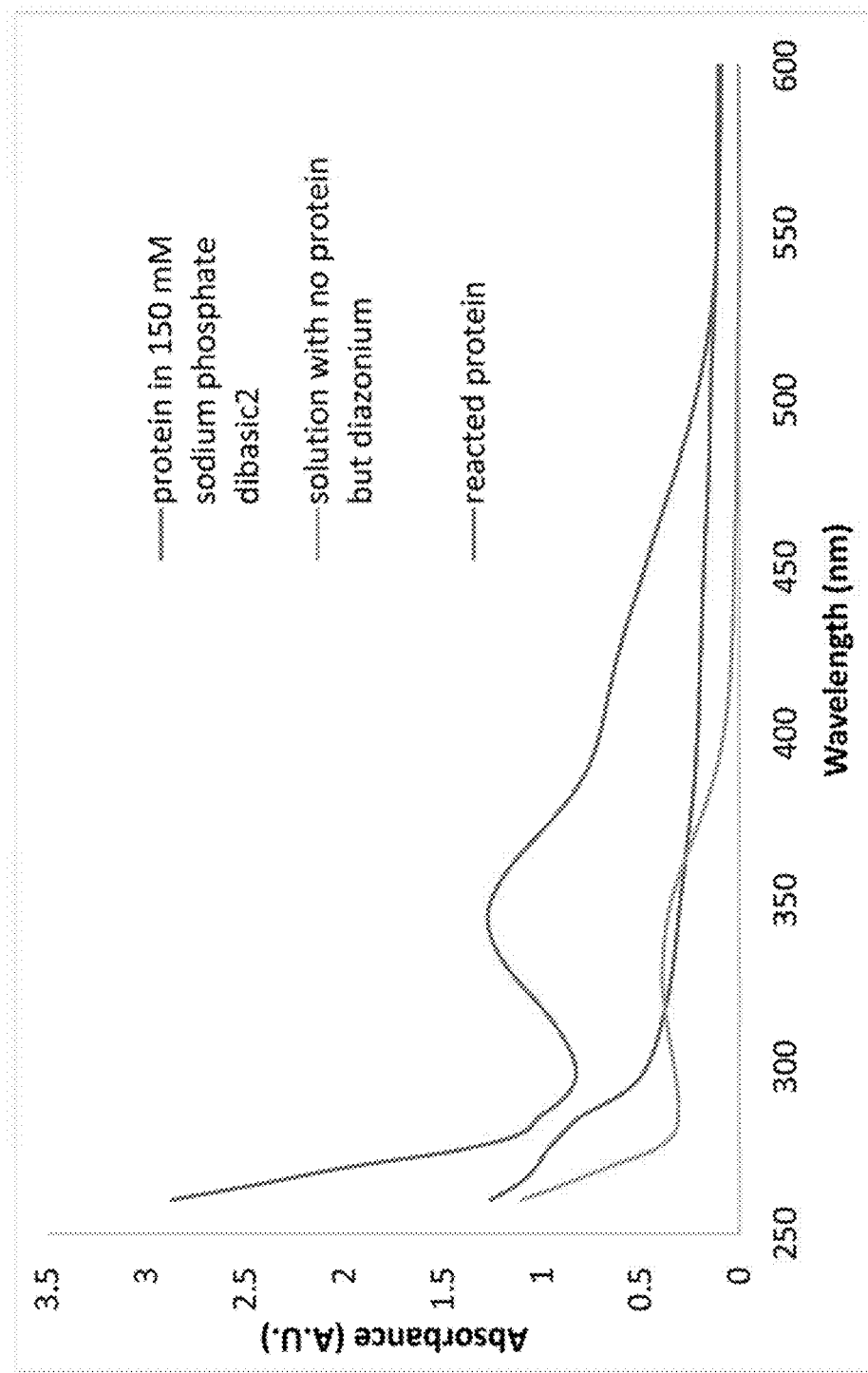
FIG. 28 depicts the diazonium coupling of nitro-substituted anilines on tyrosine residues on MUC5ACL (SEQ ID NO: 2), which occurred at 69% of residues. At 450 nM, the top line is reacted protein, the middle line is protein in 150 mM sodium phosphate dibasic2, and the bottom line is solution with no protein but diazonium.

The effectiveness of diazonium coupling at functionalizing proteins was tested on MUC5ACL (SEQ ID NO: 2). A 1.2 mg/ml sample of protein was dissolved in buffer solution (150 mM Na$_2$HPO$_4$, pH 9, MilliQ water). 100 μL of nitro-diazonium salt solution was added to the protein solution. The mixture was stirred at 4° C. for 15 minutes. The UV-Vis absorbance of the reaction mixture at 344 nm was used to calculate the degree of modification of the proteins. 69% of all of the tyrosines present in solution were successfully modified with nitro groups as shown in FIG. 28.

Figure 29:
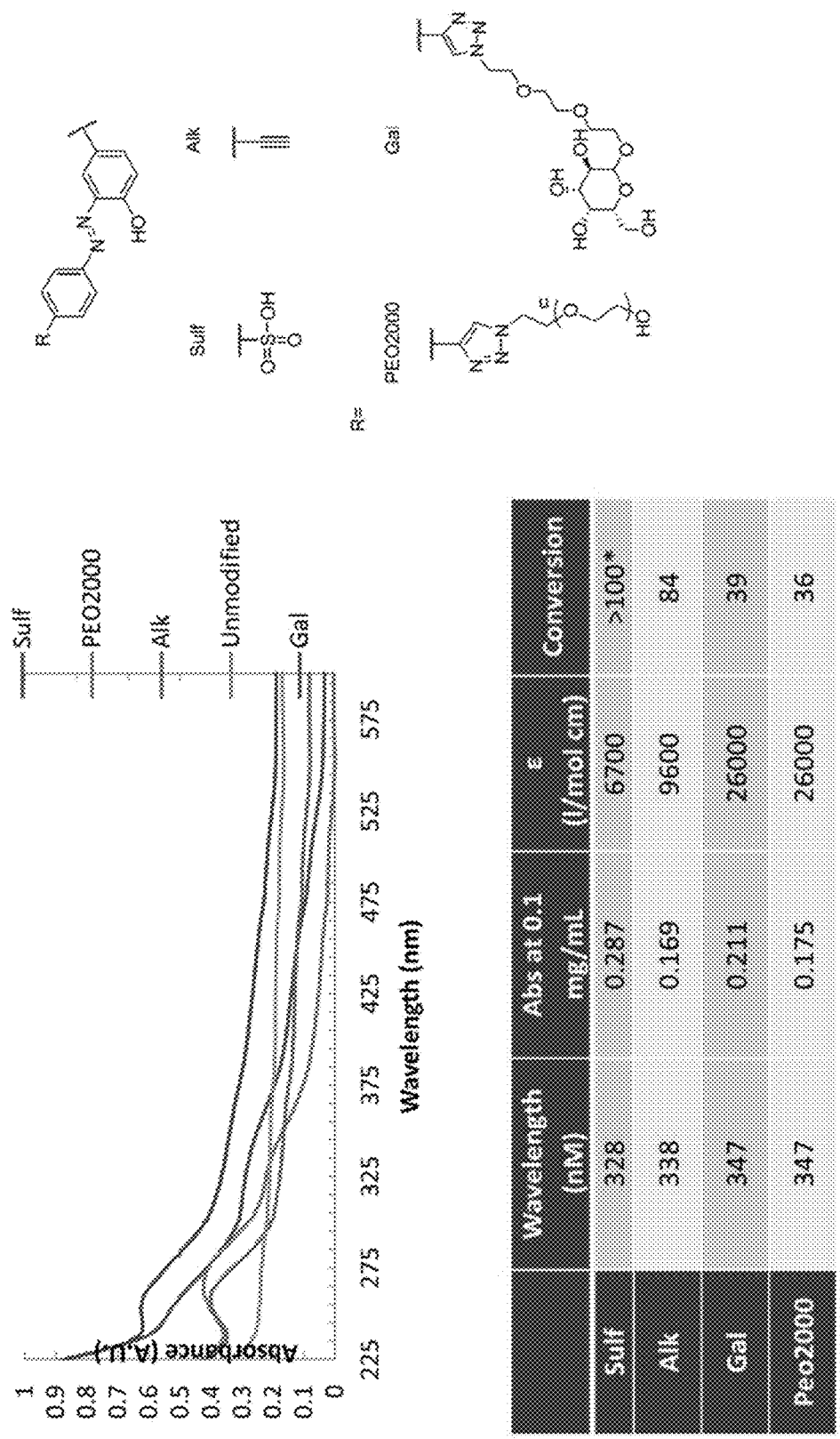
FIG. 29 depicts the diazonium coupling of X-substituted anilines A on tyrosine residues, where X is sulfate (sulf), ethynyl (alk), triazolyl-galactosyl (Gal), and triazolyl-PEO (Peo2000). At 525 nM, the topmost line is Gal, the next lower line is unmodified, the next lower line is Alk, the next lower line is Sulf, and the bottommost line is PEO2000.

In another set of experiments, the following additional substituents were installed on the mucin MUC5ACL (SEQ ID NO: 2) backbone using the above procedure: sulfate (sulf), ethynyl (alk), triazolyl-galactosyl (Gal), and triazolyl-PEO (Peo2000). The degree of modification was determined by UV-VIS spectroscopy and shown in FIG. 29, where a greater than 100% conversion was observed in the sulfate modified MUC5ACL (SEQ ID NO: 2) due to protein aggregation.

Figure 30:
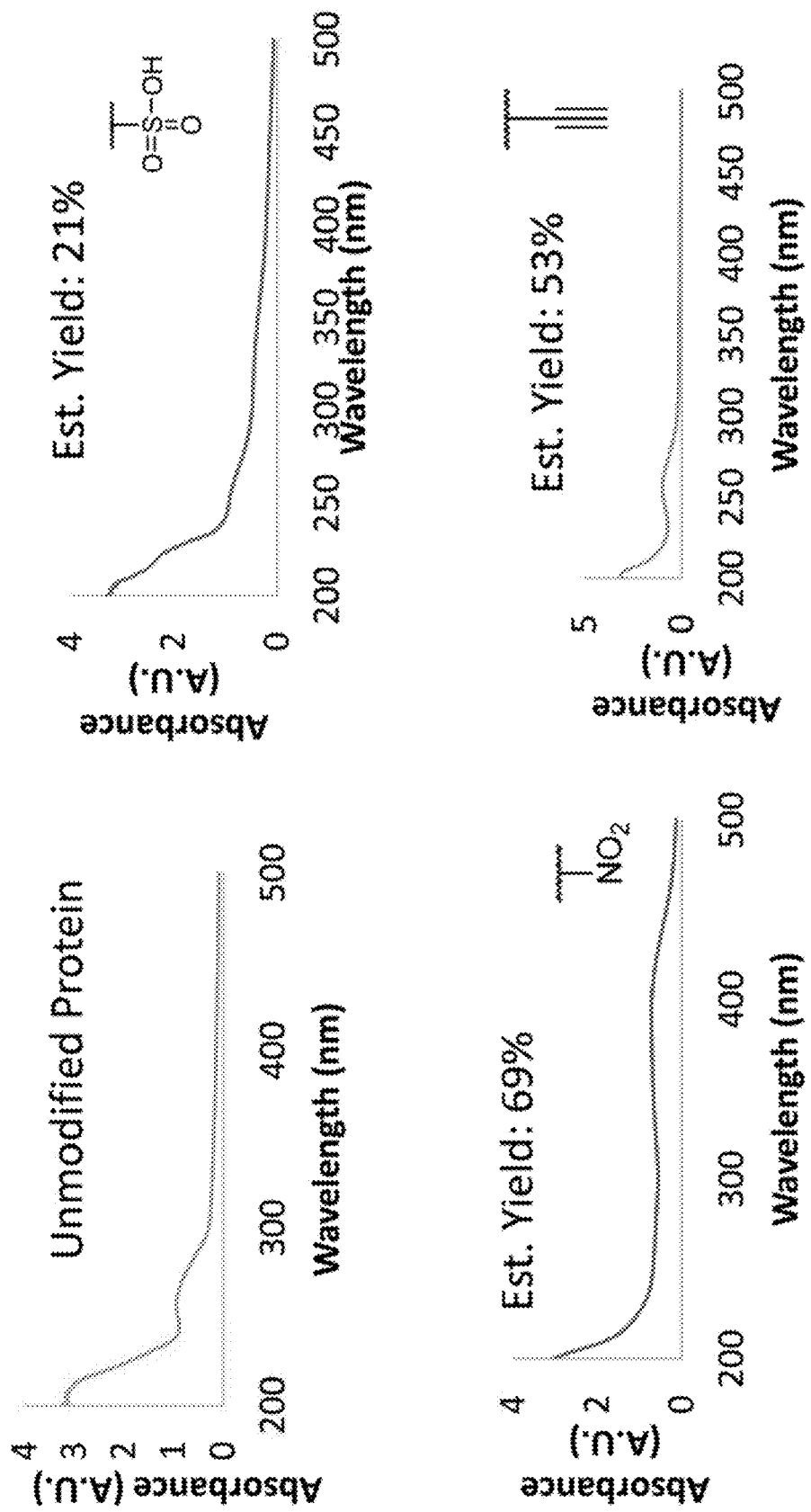
FIG. 30 depicts the UV-Vis spectra of the modified proteins shown in FIG. 29 and their estimated yields
Figure 30:
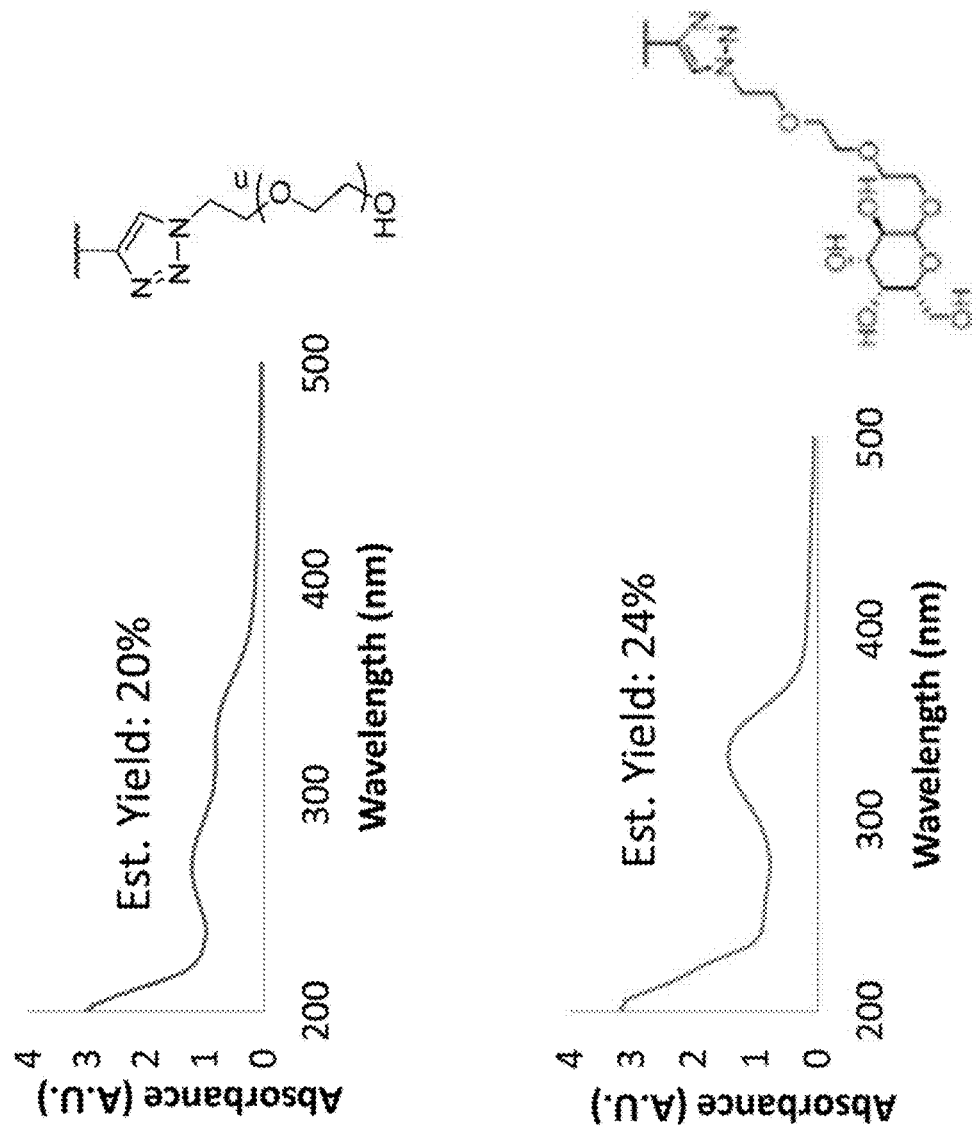

Further modification experiments analyzed by UV-VIS spectroscopy shown in FIG. 30 indicated significant yields of functionalized brush proteins as given in TABLE 3.

TABLE 3

| MUC5ACL Tyrosine substituent | Estimated Yield % |
| --- | --- |
| nitro | 69 |
| sulfate | 21 |
| ethynyl | 53 |
| triazolyl-PEO | 20 |
| triazolyl-galactosyl | 24 |

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

We claim:

1. A polypeptide comprising a plurality of tandem repeats of a sequence comprised by a mucin selected from the group consisting of SEQ ID NO: 12, SEQ ID NO: 13, SEQ ID NO: 14, SEQ ID NO: 15, SEQ ID NO: 16, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 11 and SEQ ID NO: 17, wherein about 20% to about 50% of the serine and threonine amino acids in the tandem repeats have been replaced by tyrosine residues.

2. The polypeptide of claim 1, wherein the mucin is SEQ ID NO: 16 or SEQ ID NO: 17.

3. The polypeptide of claim 1, wherein the N-terminal and C-terminal amino acids are cysteine.

4. The polypeptide of claim 1, wherein the polypeptide is selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8 and SEQ ID NO: 11.

5. The polypeptide of claim 4, wherein the polypeptide is selected from the group consisting of SEQ ID NO: 2, SEQ ID NO: 3, SEQ ID NO: 4, SEQ ID NO: 5, SEQ ID NO: 6, SEQ ID NO: 7, and SEQ ID NO: 8.

6. The polypeptide of claim 4, wherein the polypeptide is SEQ ID NO: 2.

7. The polypeptide of claim 1, wherein the number of tandem repeat sequences ranges from about 15 to about 70.

8. The polypeptide of claim 1, wherein a plurality of the tyrosine residues have been modified to include a substituent selected from the group consisting of alkyl, alkynyl, aryl, amino, carboxyl, heteroaryl, nitro, sulfate, and polyethylene oxide polymer.

9. The polypeptide of claim 8, wherein the plurality is at least 20% of the tyrosine residues.

10. A protein oligomer comprising at least two polypeptide units, wherein the polypeptide units comprise a plurality of tandem repeats of a sequence comprised by a mucin selected from the group consisting of SEQ ID NO: 12, SEQ ID NO: 13, SEQ ID NO: 14, SEQ ID NO: 15, SEQ ID NO: 16, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 11 and SEQ ID NO: 17; and about 20% to about 50% of the serine and threonine amino acids in the protein oligomer have been replaced by tyrosine residues.

11. The protein oligomer of claim 10, wherein the mucin is SEQ ID NO: 16 or SEQ ID NO: 17.

12. The protein oligomer of claim 10, wherein the N-terminal and C-terminal amino acids are cysteine.

13. The protein oligomer of claim 10, wherein the polypeptide is selected from the group consisting of SEQ ID NO:

2, SEQ ID NO: 3, SEQ ID NO: 4, SEQ ID NO: 5, SEQ ID NO: 6, SEQ ID NO: 7, SEQ ID NO: 8 and SEQ ID NO: 11.

14. The protein oligomer of claim 13, wherein the polypeptide is selected from the group consisting of SEQ ID NO: 2, SEQ ID NO: 3, SEQ ID NO: 4, SEQ ID NO: 5, SEQ ID NO: 6, SEQ ID NO: 7, and SEQ ID NO: 8.

15. The protein oligomer of claim 13, wherein the protein is SEQ ID NO: 2.

16. The protein oligomer of claim 10, wherein the number of tandem repeat sequences ranges from about 15 to about 70.

17. The protein oligomer of claim 10, wherein the at least two polypeptide units are linked together through a disulfide bond between the N-terminus of one protein and the C-terminus of the other protein.

18. The protein oligomer of claim 17, wherein 2 to 30 polypeptide units are linked together using disulfide bonds.

19. The protein oligomer of claim 10, wherein a plurality of the tyrosine residues have been modified to include a substituent selected from the group consisting of alkyl, alkynyl, aryl, amino, carboxyl, heteroaryl, nitro, sulfate, and polyethylene oxide polymer.

20. The protein oligomer of claim 19, wherein the plurality is at least 20% of the tyrosine residues.

* * * * *